United States Patent
Chen et al.

(10) Patent No.: US 10,253,029 B2
(45) Date of Patent: Apr. 9, 2019

(54) DUAL-WARHEAD COVALENT INHIBITORS OF FGFR-4

(71) Applicant: Newave Pharmaceutical Inc., Pleasanton, CA (US)

(72) Inventors: Yi Chen, Pleasanton, CA (US); Yan Lou, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 0 days.

(21) Appl. No.: 15/645,067

(22) Filed: Jul. 10, 2017

(65) Prior Publication Data

US 2017/0305918 A1 Oct. 26, 2017

Related U.S. Application Data

(63) Continuation of application No. PCT/US2016/013506, filed on Jan. 15, 2016.

(60) Provisional application No. 62/245,647, filed on Oct. 23, 2015, provisional application No. 62/143,988, filed on Apr. 7, 2015, provisional application No. 62/104,772, filed on Jan. 18, 2015.

(51) Int. Cl.
| | |
|---|---|
| *A61K 31/519* | (2006.01) |
| *C07D 487/04* | (2006.01) |
| *C07D 471/04* | (2006.01) |
| *C07D 239/48* | (2006.01) |
| *C07D 401/12* | (2006.01) |
| *C07D 403/12* | (2006.01) |
| *C07D 405/12* | (2006.01) |
| *C07D 405/14* | (2006.01) |

(52) U.S. Cl.
CPC ......... *C07D 487/04* (2013.01); *C07D 239/48* (2013.01); *C07D 401/12* (2013.01); *C07D 403/12* (2013.01); *C07D 405/12* (2013.01); *C07D 405/14* (2013.01); *C07D 471/04* (2013.01)

(58) Field of Classification Search
CPC .......................... A61K 31/519; C07D 471/04
USPC ..................... 514/264.11; 544/278
See application file for complete search history.

(56) References Cited

U.S. PATENT DOCUMENTS

2006/0142312 A1 6/2006 Flamme et al.
2014/0296233 A1 10/2014 D'Agostino et al.

FOREIGN PATENT DOCUMENTS

WO 2014/011900 A2 1/2014
WO 2014/182829 A1 11/2014

OTHER PUBLICATIONS

Chawla et. al.; Current Research & Information on Pharmaceutical Science, 2004, 5(1), p. 9.*
Newman et. al.; Drug Discovery Today; 2003, 8(19) p. 898-905.*
Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Carmi et al., Epidermal growth factor receptor irreversible inhibitors: chemical exploration of the cysteine-trap portion. Mini Rev Med Chem. Oct. 2011;11(12):1019-30.

\* cited by examiner

*Primary Examiner* — Jeffrey H Murray
(74) *Attorney, Agent, or Firm* — McCarter & English, LLP; Yu Lu; Wei Song

(57) ABSTRACT

The disclosure includes compounds of Formula (I)

Formula (I)

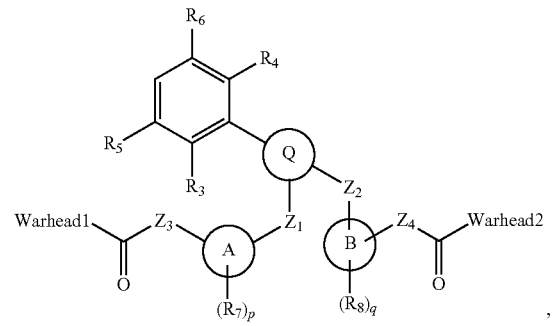

wherein Warhead1, Warhead2, $R_3$, $R_4$, $R_5$, $R_6$, $R_7$, $R_8$, Q, A, B, p, q, $Z_1$, $Z_2$, $Z_3$, and $Z_4$ are defined herein. Also disclosed is a method for treating a neoplastic disease with these compounds.

19 Claims, No Drawings

DUAL-WARHEAD COVALENT INHIBITORS OF FGFR-4

REFERENCE TO RELATED APPLICATIONS

This application is a continuation of International Patent Application No. PCT/US2016/013506, filed on Jan. 15, 2016, which claims the benefit of the filing dates under 35 U.S.C. 119(e) of U.S. Provisional Application No. 62/104,772, filed on Jan. 18, 2015; 62/143,988, filed on Apr. 7, 2015; and 62/245,647, filed on Oct. 23, 2015, the entire contents of each of the above applications are incorporated herein by reference.

BACKGROUND OF THE INVENTION

Fibroblast growth factor receptor 4 (FGFR-4) is a protein that in humans is encoded by the FGFR-4 gene. This protein is a member of the fibroblast growth factor receptor family, where amino acid sequence was highly conserved between members throughout evolution. FGFR family members 1-4 differ from one another in their ligand affinities and tissue distribution. A full-length representative protein consists of an extracellular region composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. The genomic organization of the FGFR-4 gene encompasses 18 exons. Although alternative splicing has been observed, there is no evidence that the C-terminal half of the IgIII domain of this protein varies between three alternate forms, as indicated for FGFR 1-3. Ectopic mineralization, characterized by inappropriate calcium-phosphorus deposition in soft tissue, has been observed in rats treated with an FGFR-1 inhibitor (Brown, A P et al. (2005), *Toxicol. Pathol.*, 449-455). This suggests that selective inhibition of FGFR-4 without inhibition of other isoforms of FGFR, including FGFR-1, may be desirable in order to avoid certain toxicities. FGFR-4 preferentially binds fibroblast growth factor 19 (FGF19) and has recently been associated with the progression of sarcomas, renal cell cancer, breast cancer, gastric cancer, pancreatic cancer, ovarian cancer, and liver cancer (Ho H K, et al. (2009) *J. Hepatol.*, 50(1):118-127; Motoda N, et al., (2011) *Int. J. Oncol.*, 38(1):133-143; Poh W, et al., (2012) *Mol. Cancer*, 11(14):1-10; Zaid T M, et al., (2013) *Clin. Cancer Res.* 19(4):809-820.; Ye Y W, et al., (2011) *Cancer*, 117(23):5304-5313).

FGFR-4 is a highly unique protein that there are two cysteine residues near the binding site of small molecule FGFR-4 inhibitor: Cys477 and Cys552. The covalent FGFR-4 inhibitors reported by Brameld, Kenneth (WO 2014/182829) and Tan L etc. (*Proc. National. Acad. Sci. USA.*, 2014 Nov. 11, 111(45), E4869-E4877) covalently binds to Cys477, while the covalent FGFR-4 inhibitors reported by Bifulco, Neil, etc. (WO 2014/011900) covalently binds to Cys552. Although these covalent FGFR-4 inhibitors have made a significant contribution to the art, there is a continuing search in this field of art for improved pharmaceuticals.

SUMMARY OF THE INVENTION

The present invention relates to a class of rationally designed dual-warhead covalent FGFR-4 inhibitors in which one warhead covalently bind to the cysteine residue Cys477 and at the same time the other warhead covalently bind to the cysteine residue Cys552. Therefore, such dual-warheads FGFR-4 inhibitors may possess highly favourable potency. In addition, since cysteine residue Cys522 only occurs in FGFR-4 but not in FGFR-1/2/3, our dual-warheads inhibitors may be highly selective to FGFR-4. Thus, the compounds of the present invention may be useful in treating diseases with aberrant activation of the FGFR-4 signaling pathway.

Thus in one aspect, the invention provides a dual-warhead covalent inhibitor of FGFR-4 that can covalently bind to both Cys477 and Cys552 residues of FGFR-4.

In a related aspect, the invention provides compounds of Formula (I), or an N-oxide thereof, or a pharmaceutically acceptable salt, solvate, polymorph, stereoisomer, tautomer, an isotopic form, or a prodrug of said compound of Formula (I) or N-oxide thereof:

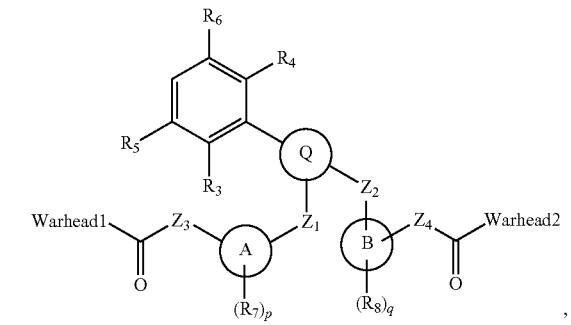

Formula (I)

wherein:

Q is a 9- or 10-membered bicyclic heterocyclic, or a pseudo-bicyclic;

each of A, and B is a cycloalkyl, cycloalkenyl, heterocycloalkyl, heterocycloalkenyl, aryl, heteroaryl;

$Z_1$ is alkyl, alkenyl, or alkynyl;

$Z_2$ is N(H), O, S, S(O$_2$);

$Z_3$ is N(R$_a$) if the atom which it connects to ring A is a carbon atom; or $Z_3$ is a direct bond if ring A is a heterocycloalkyl, heterocycloalkenyl, or heteroaryl and the atom which $Z_3$ connects to ring A is a nitrogen atom;

$Z_4$ is N(R$_a$) if the atom which it connects to ring B is a carbon atom; or $Z_4$ is a direct bond if ring B is a heterocycloalkyl, heterocycloalkenyl, or heteroaryl and the atom which $Z_4$ connects to ring B is a nitrogen atom;

Warhead1 is

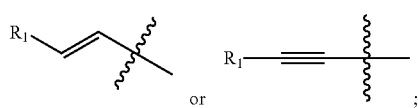

Warhead2 is

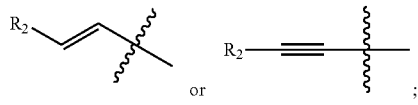

each of p, q, independently, is 0, 1, 2, 3, or 4; and each of $R_1$, $R_2$, $R_3$, $R_4$, $R_5$, $R_6$, $R_7$, and $R_8$, independently, is H, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, alkyl-$NR_bR_c$, $NR_bR_c$, $C(O)R_a$, $S(O)R_a$, $SO_2R_a$, $P(O)R_bR_c$, $C(O)N(R_b)R_c$, $N(R_b)C(O)R_c$, $C(O)OR_a$, $OC(O)R_a$, $SO_2N(R_b)R_c$, or $N(R_b)SO_2R_c$, in which each of $R_a$, $R_b$, and $R_c$, independently, is H, alkyl, alkenyl, alkynyl, cycloalkyl, cycloalkenyl, heterocycloalkyl, heterocycloalkenyl, aryl, heteroaryl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, dialkylamino, or alkylamino.

In certain embodiments, Q is

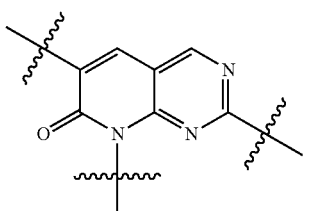

,

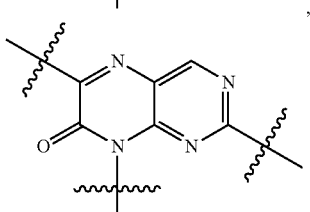

,

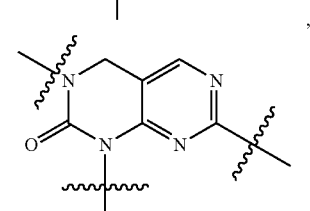

,

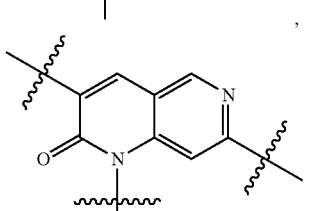

,

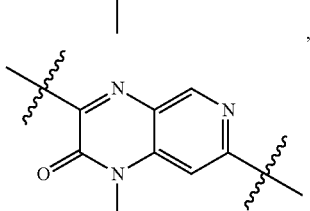

,

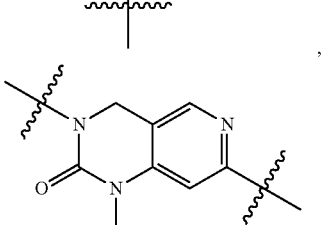

or

-continued

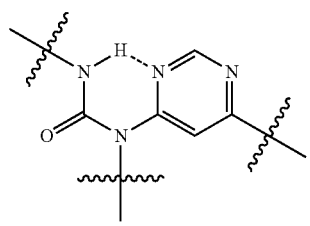

.

In certain embodiments, the compound is represented by (II):

Formula (II)

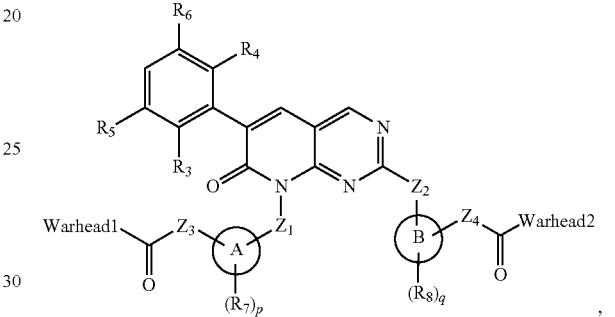

, in which $Z_1$ is alkyl.

In certain embodiments, the compound is represented by formula (III):

Formula (III)

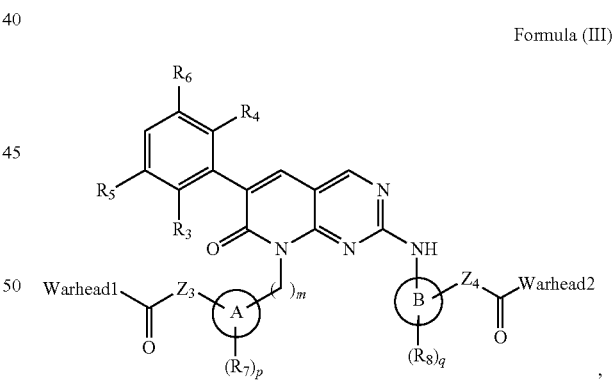

, in which m is 0, 1, 2, 3, or 4.

In any of the preceding embodiments, A may be

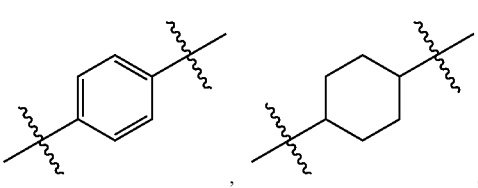

,

-continued

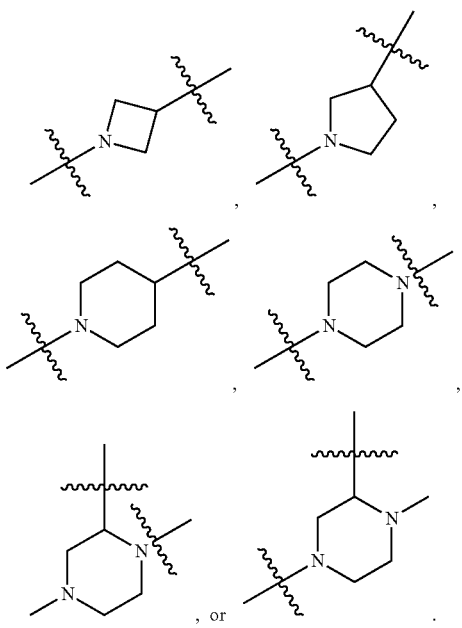

In any of the preceding embodiments, B may be

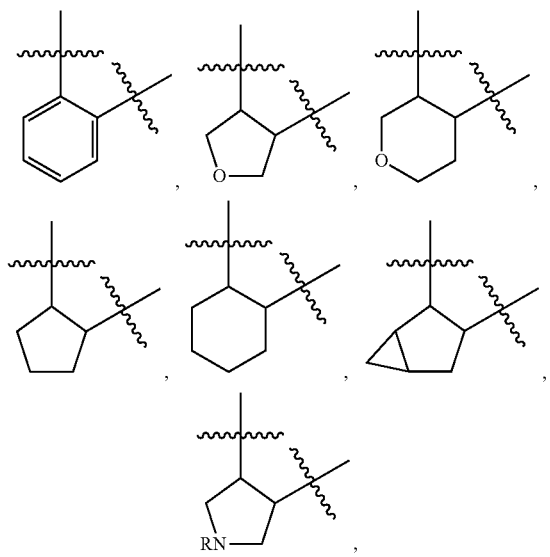

in which R is H, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, alkyl-$NR_bR_c$, $NR_bR_c$, $C(O)R_a$, $S(O)R_a$, $SO_2R_a$, $P(O)R_bR_c$, $C(O)N(R_b)R_c$, $N(R_b)C(O)R_c$, $C(O)OR_a$, $OC(O)R_a$, $SO_2N(R_b)R_c$, or $N(R_b)SO_2R_c$.

In any of the preceding embodiments, each of $R_3$ and $R_4$, may independently be H or halo.

In any of the preceding embodiments, each of $R_5$ and $R_6$, may independently be H or alkoxy.

In any of the preceding embodiments, each of Warhead1 and Warhead2, may independently be

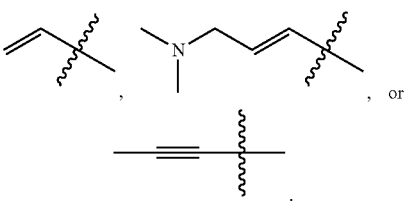

In certain embodiments, each of $R_3$ and $R_4$, is independently H or halo; each of $R_5$ and $R_6$, is independently H or alkoxy; and each of Warhead1 and Warhead2, is independently

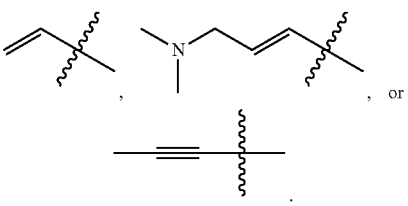

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in, for example, treating a neoplastic disease, therapeutic uses thereof, and use of the compounds for the manufacture of a medicament for treating the disease/disorder.

In certain embodiments, the invention provides a pharmaceutical composition comprising any one of a compound of Formula (I), (II), or (III), such as those described herein, or an N-oxide thereof, or a pharmaceutically acceptable salt, solvate, polymorph, tautomer, stereoisomer, an isotopic form, or a prodrug thereof, or an N-oxide thereof, and a pharmaceutically acceptable diluent or carrier.

This invention also relates to a method of treating a neoplastic disease, comprising administering to a subject in need thereof an effective amount of any one of a compound of Formula (I), (II), or (III), or an N-oxide thereof, or a pharmaceutically acceptable salt, solvate, polymorph, tautomer, stereoisomer, an isotopic form, or a prodrug thereof, or an N-oxide thereof, or an effective amount of one or more of the compounds, modifications, and/or salts, and compositions thereof, such as those described herein.

In certain embodiments, the neoplastic disease includes but are not limited to: lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

In certain embodiments, the neoplastic disease is liver cancer, breast cancer, lung cancer, ovarian cancer, or a sarcoma. In certain embodiments, the neoplastic disease is hepatocellular carcinoma.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc.) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

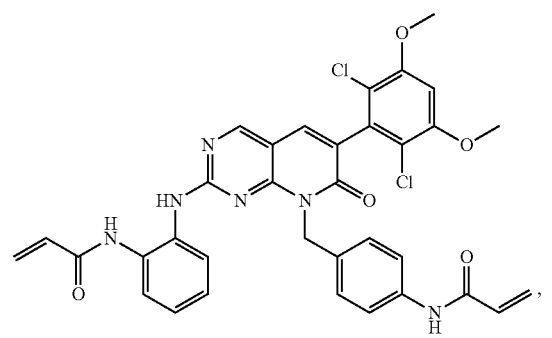

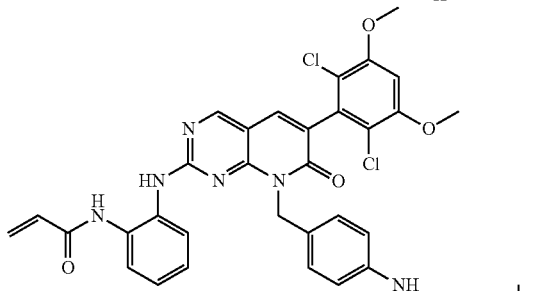

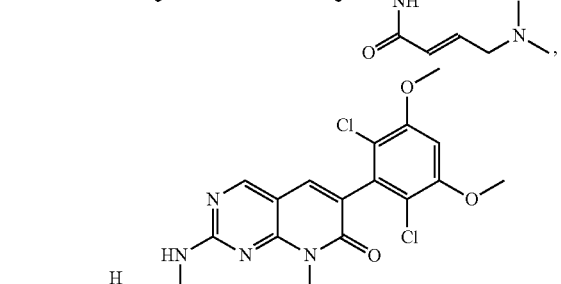

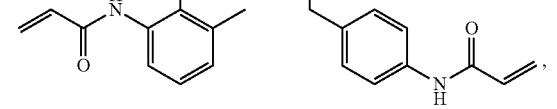

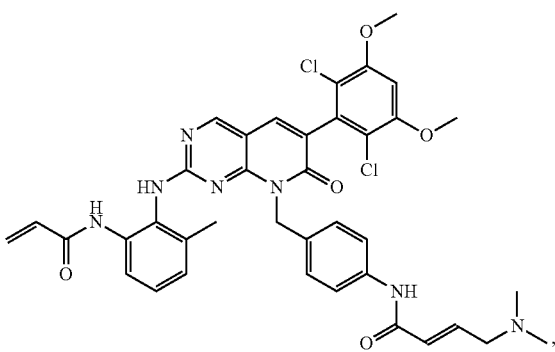

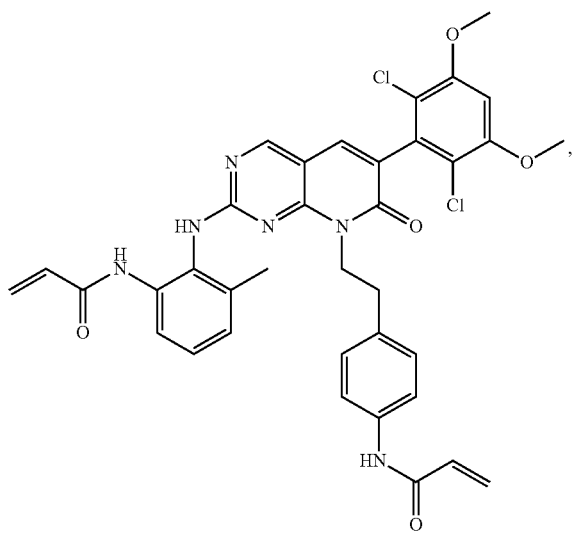

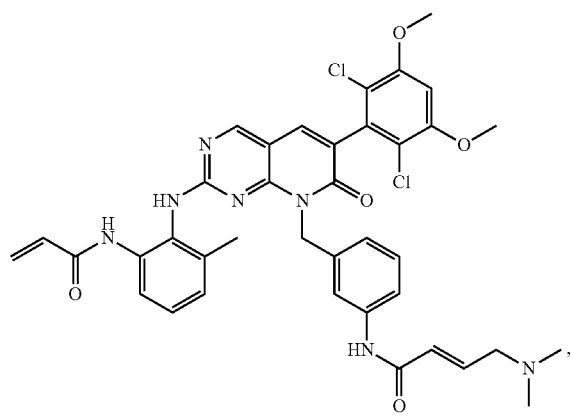

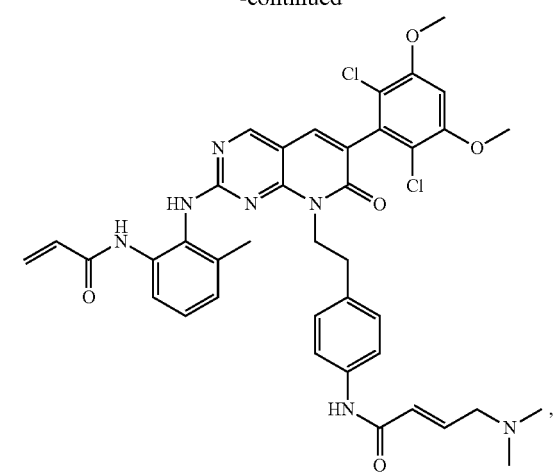
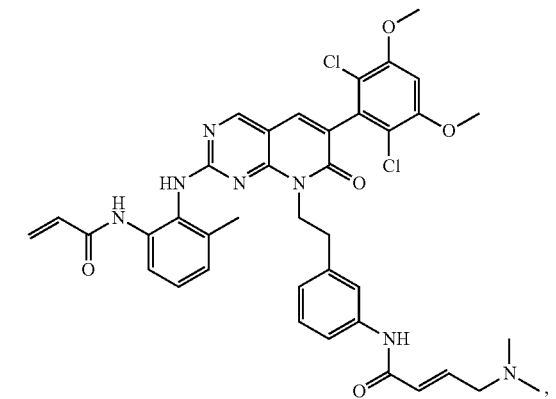
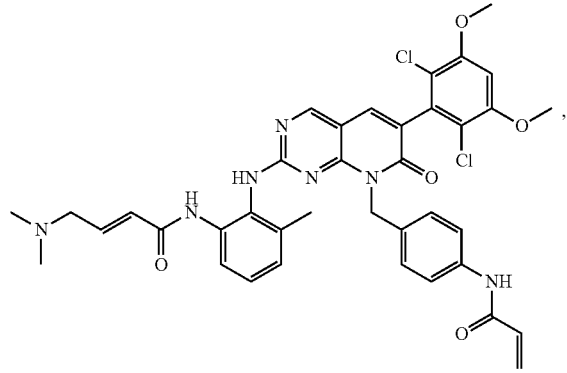
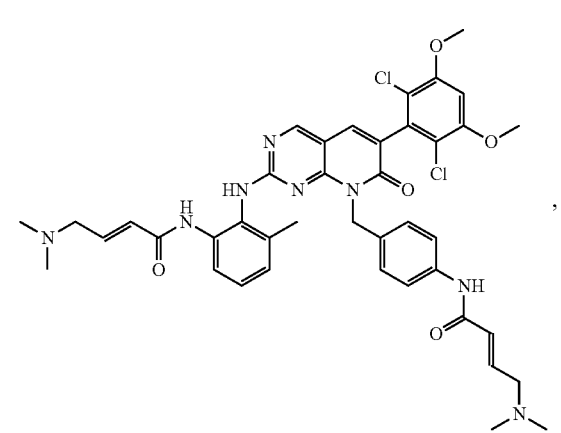
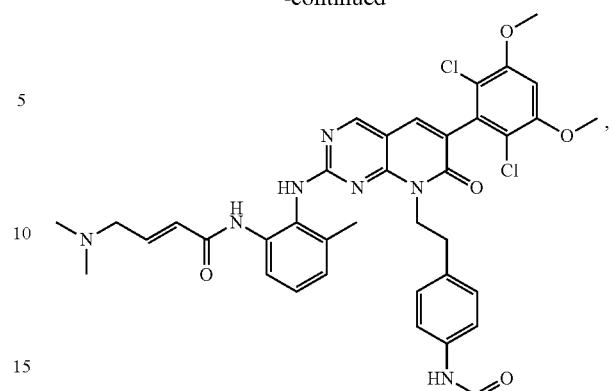
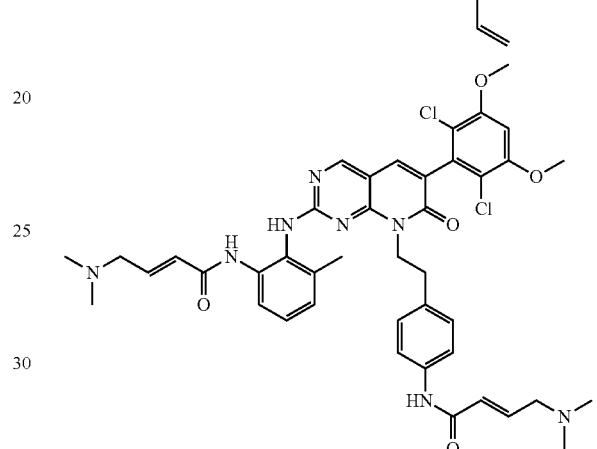
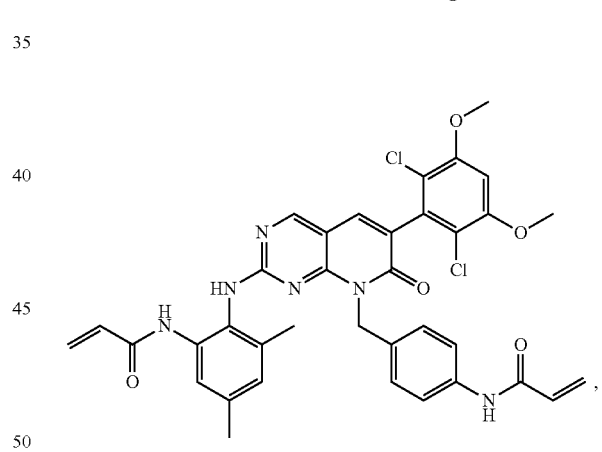
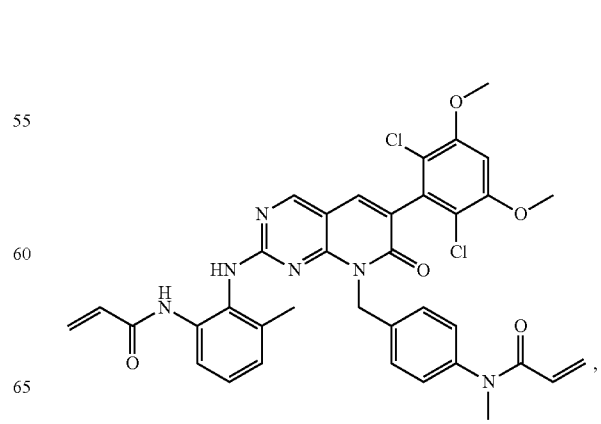

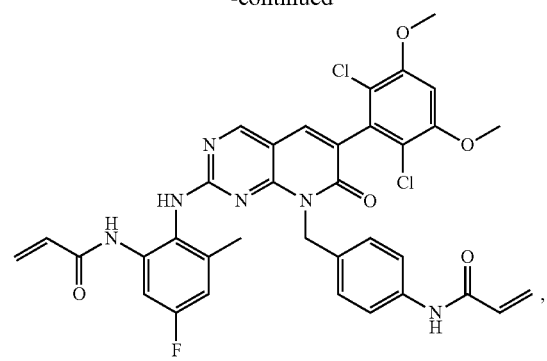
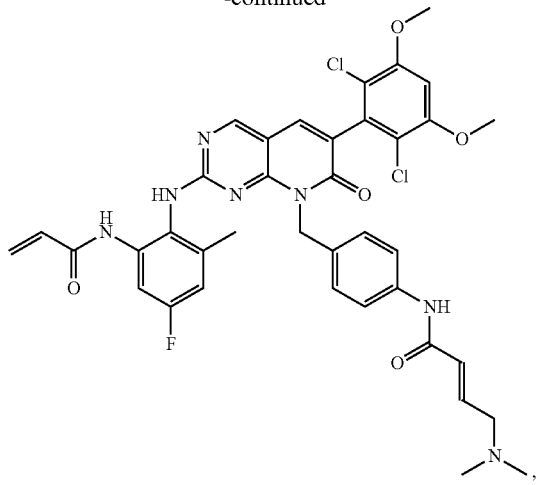
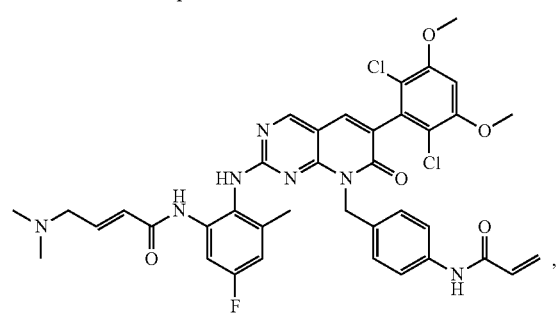
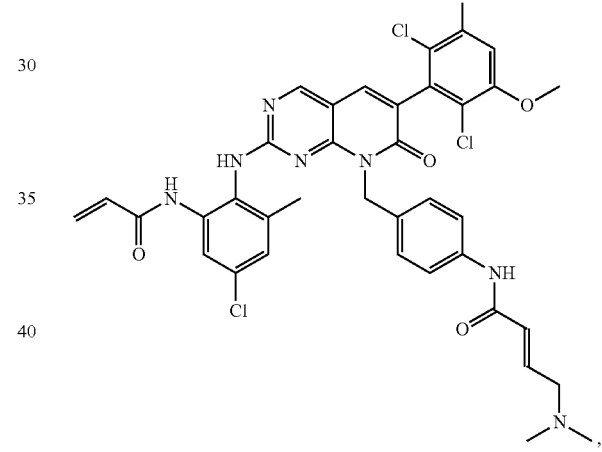
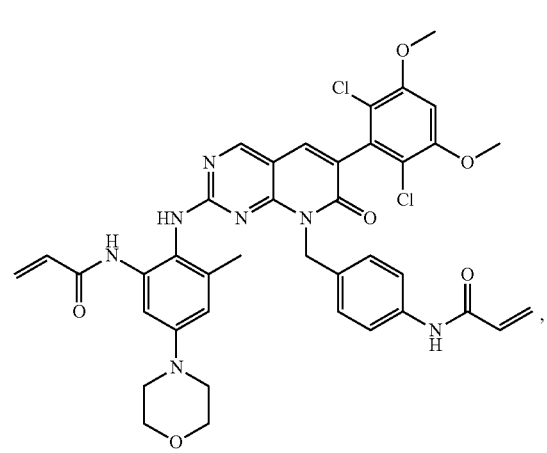
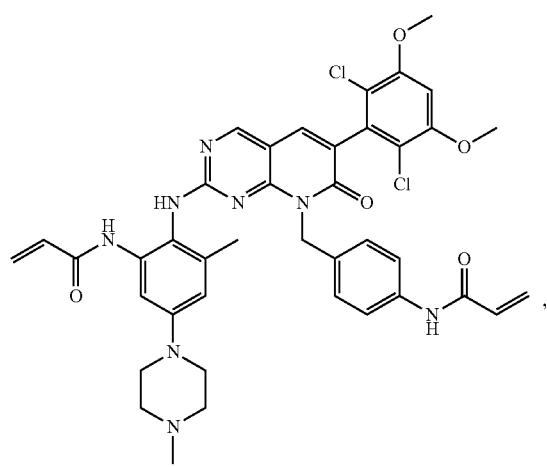
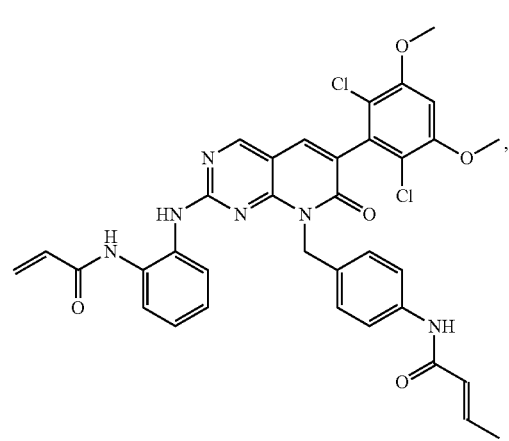

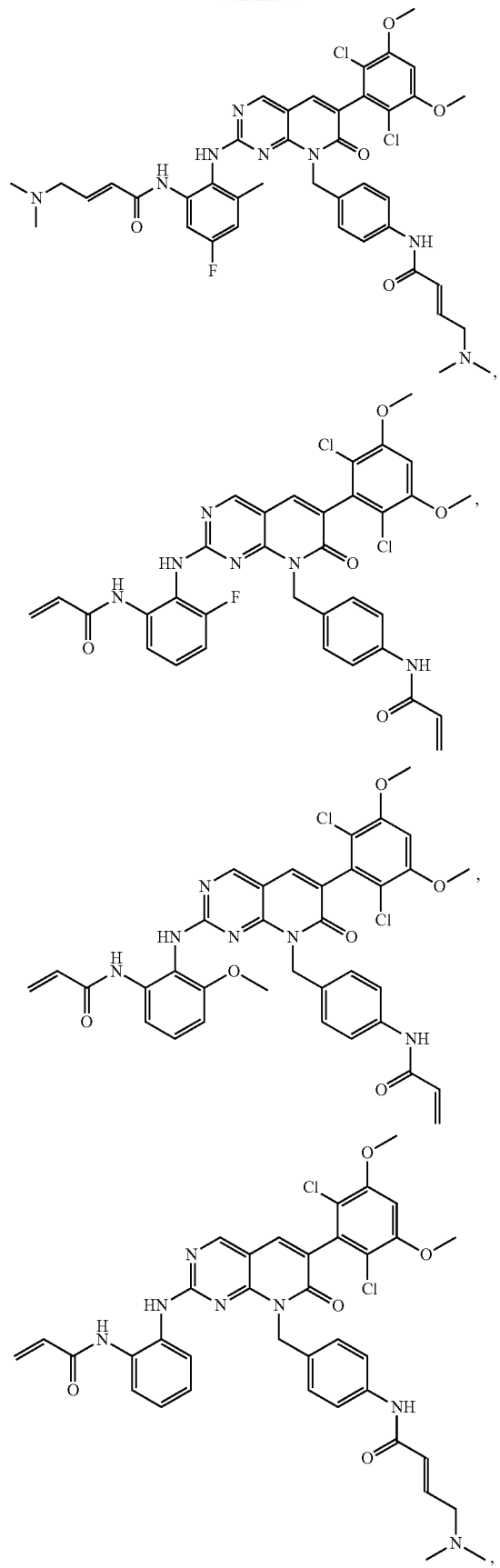
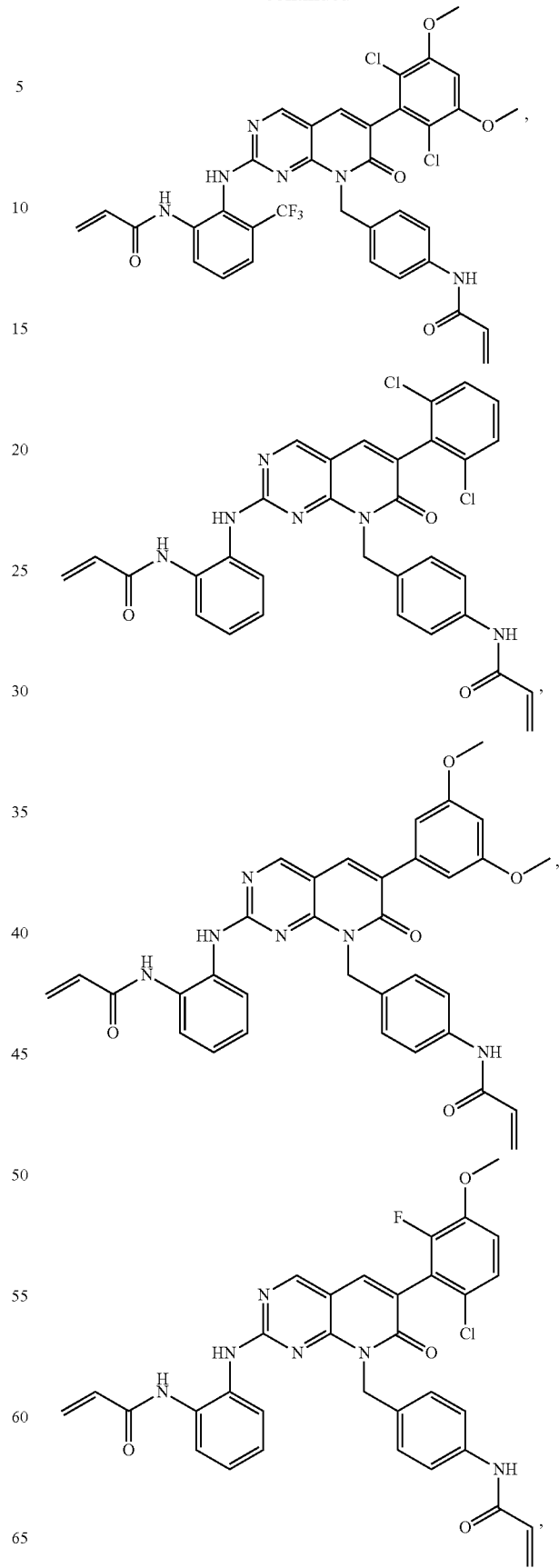

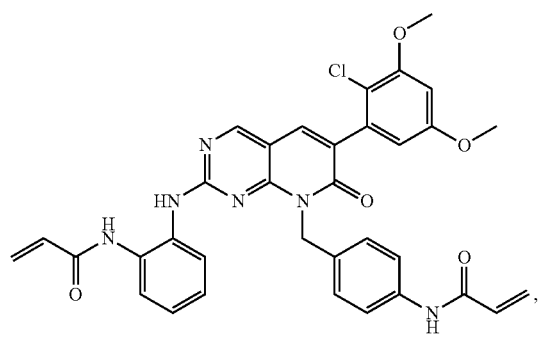
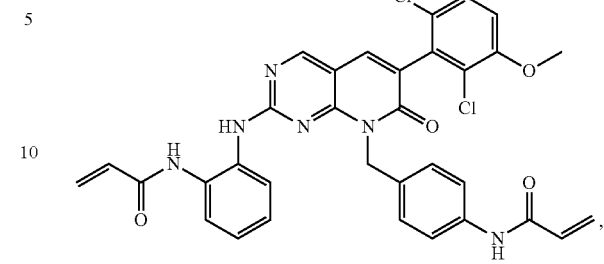
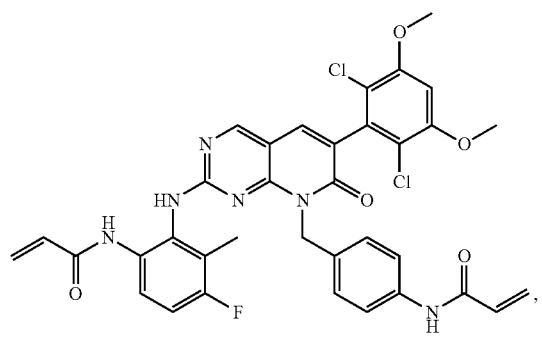
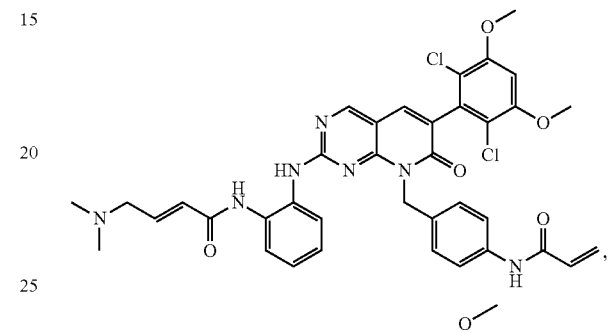
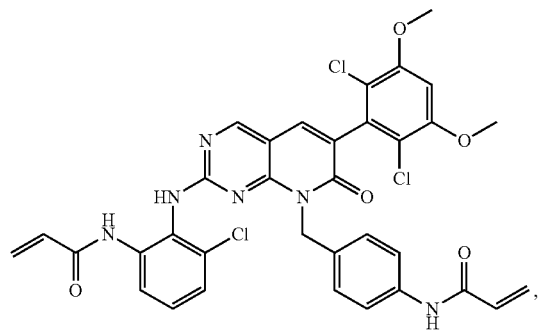
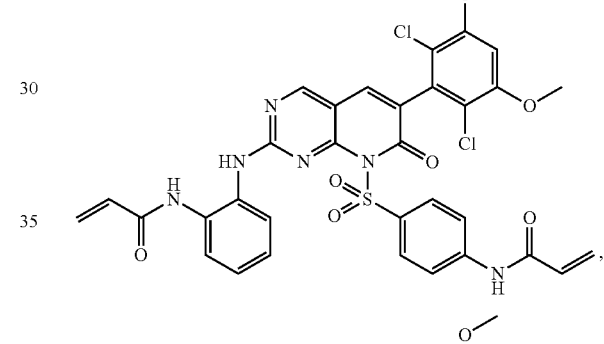
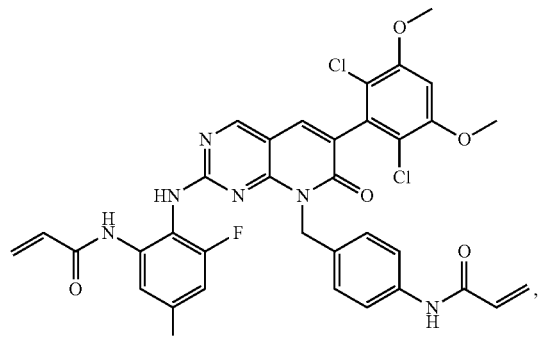
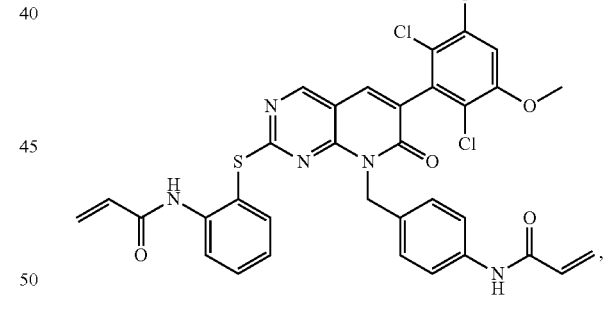
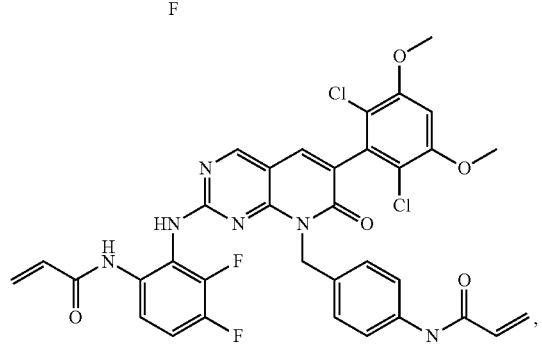
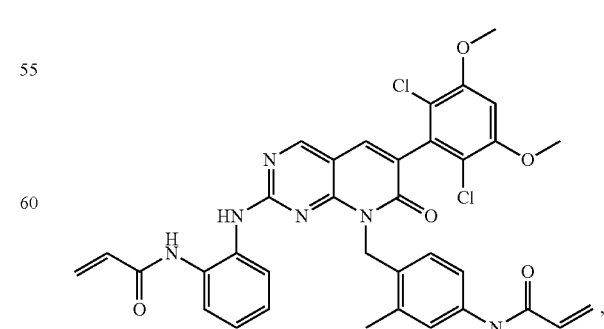

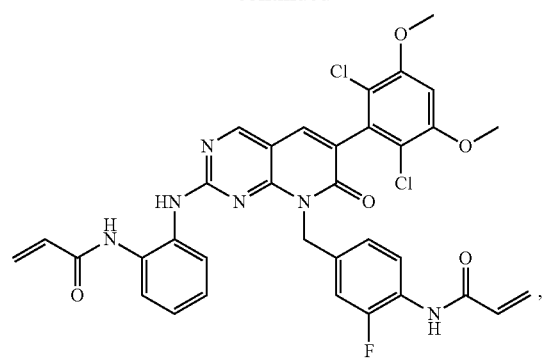
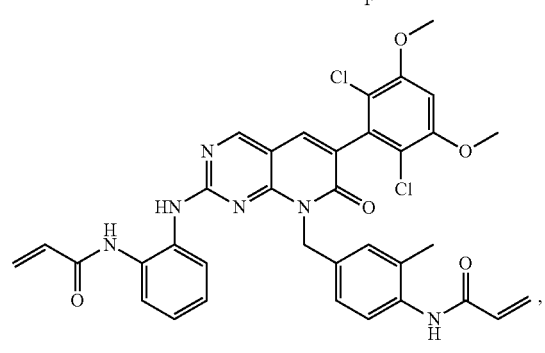
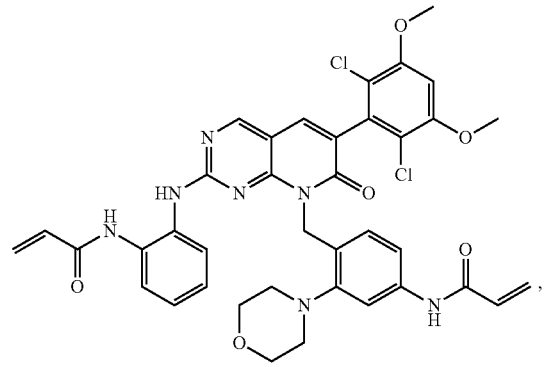
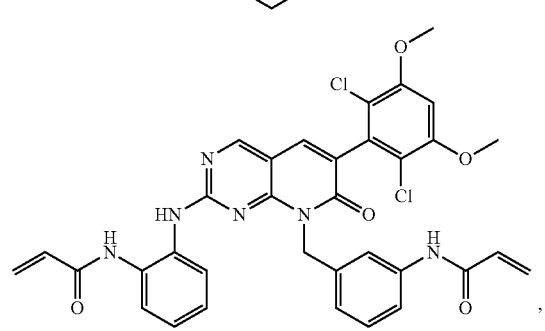
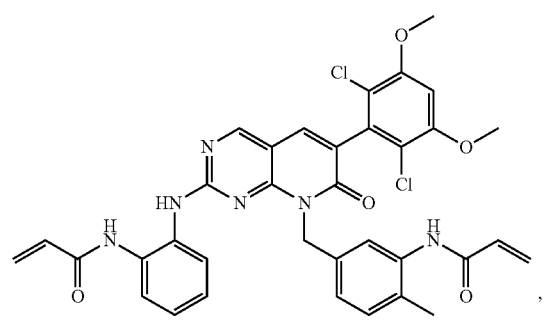
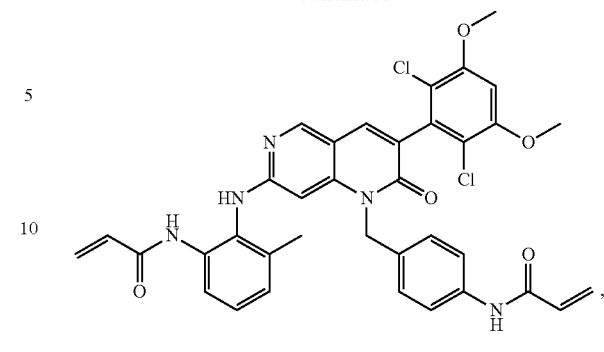
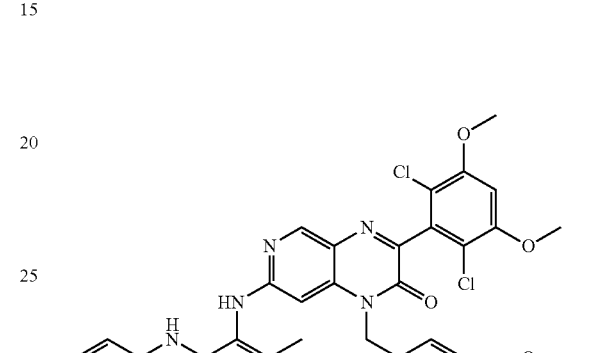
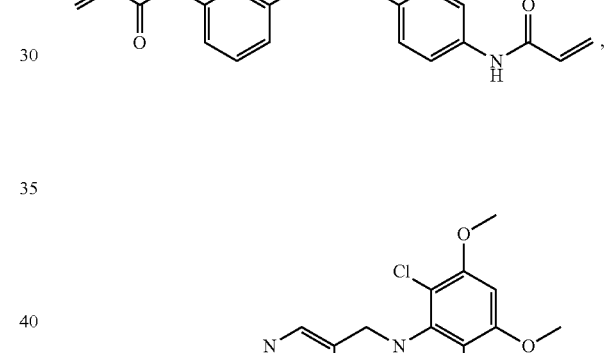
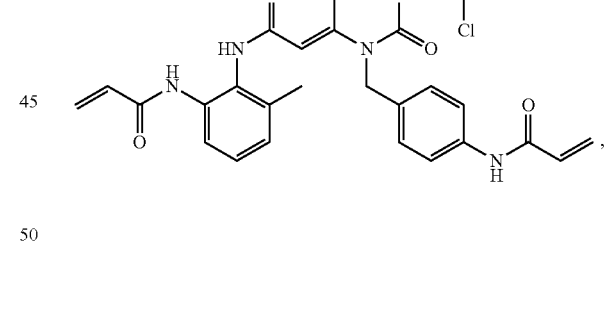
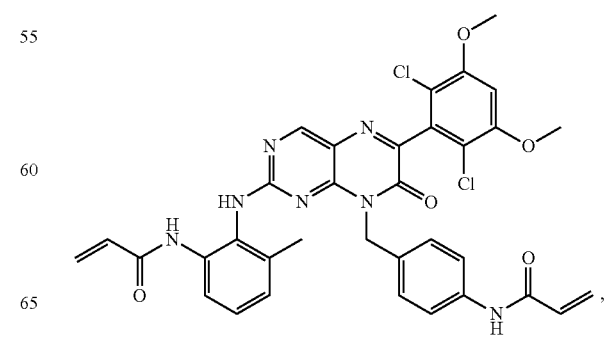

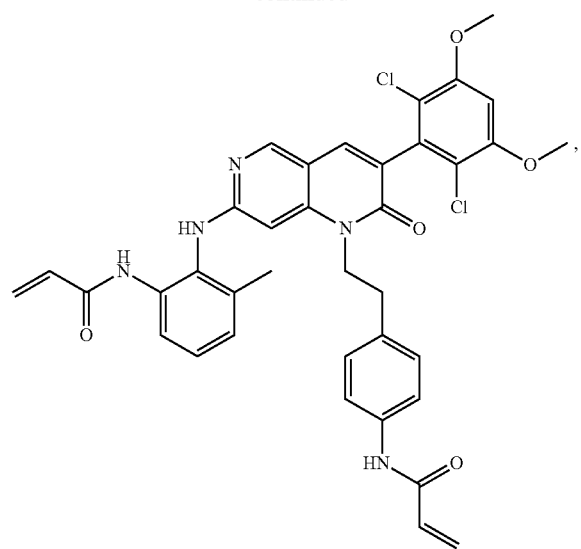
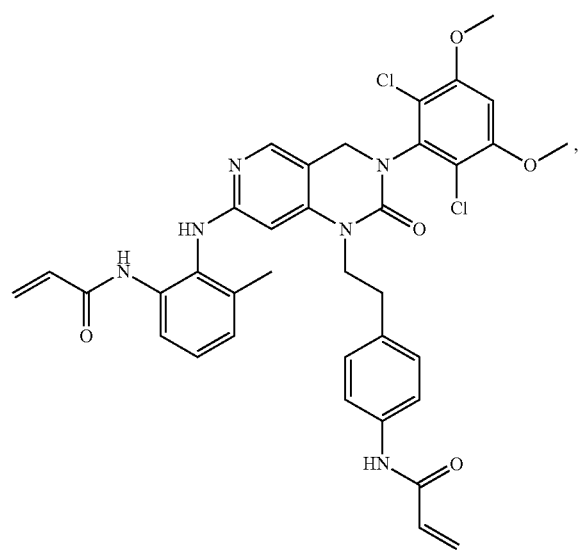
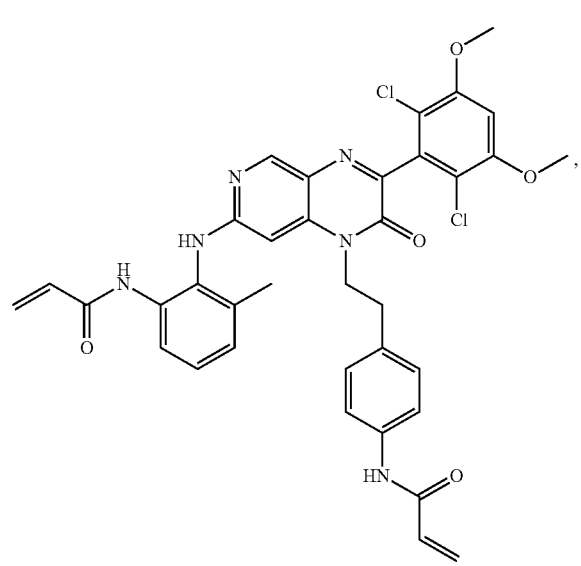
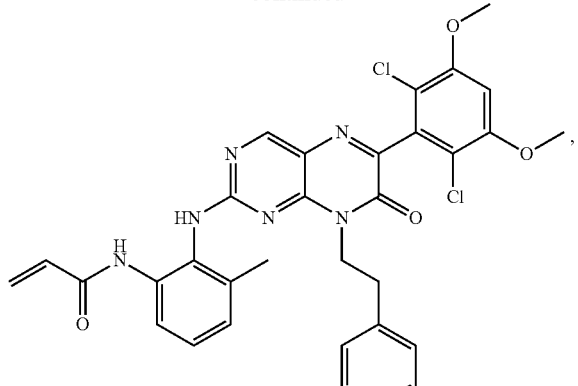
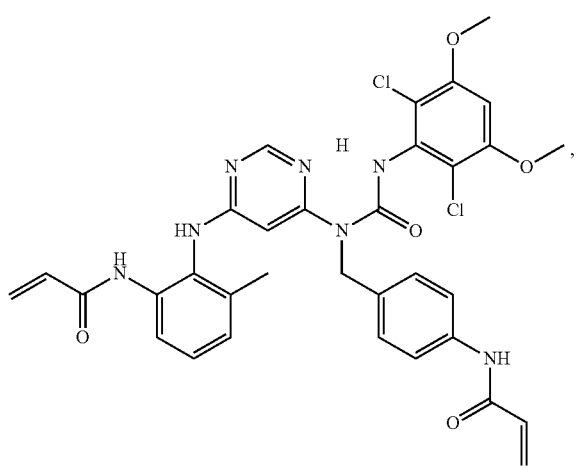
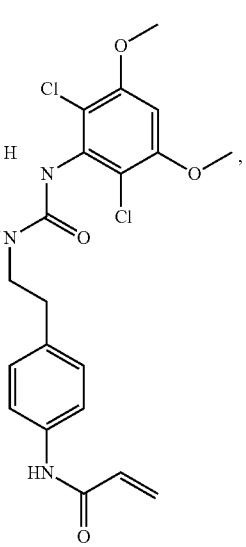

21
-continued
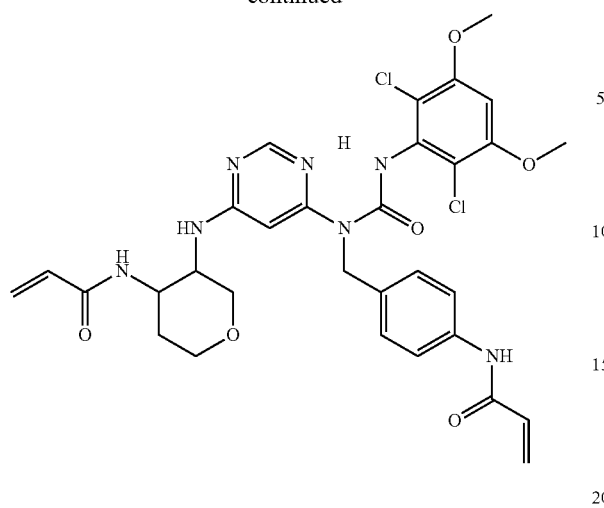
22
-continued
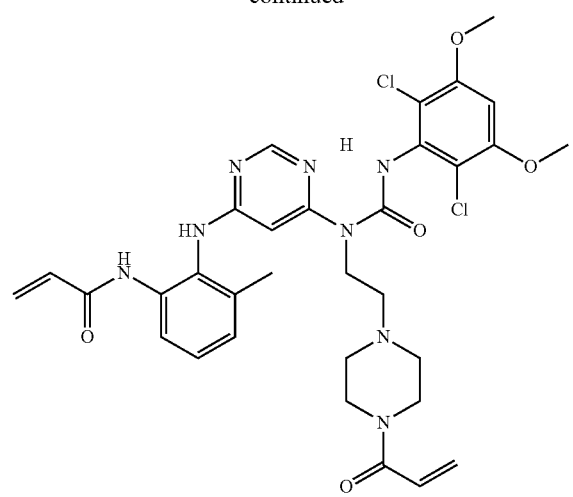
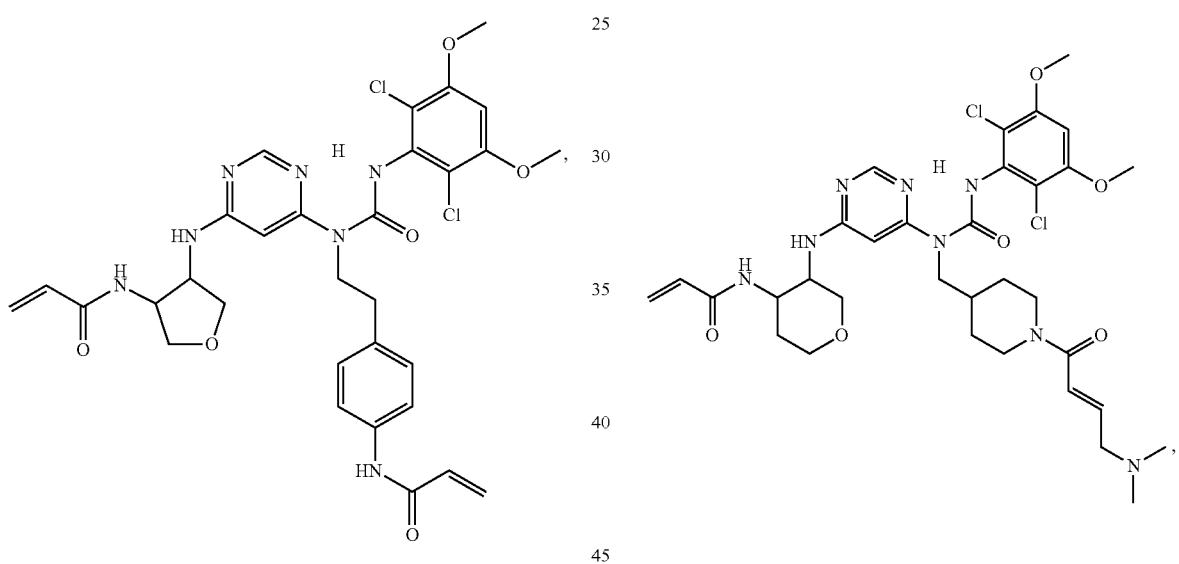
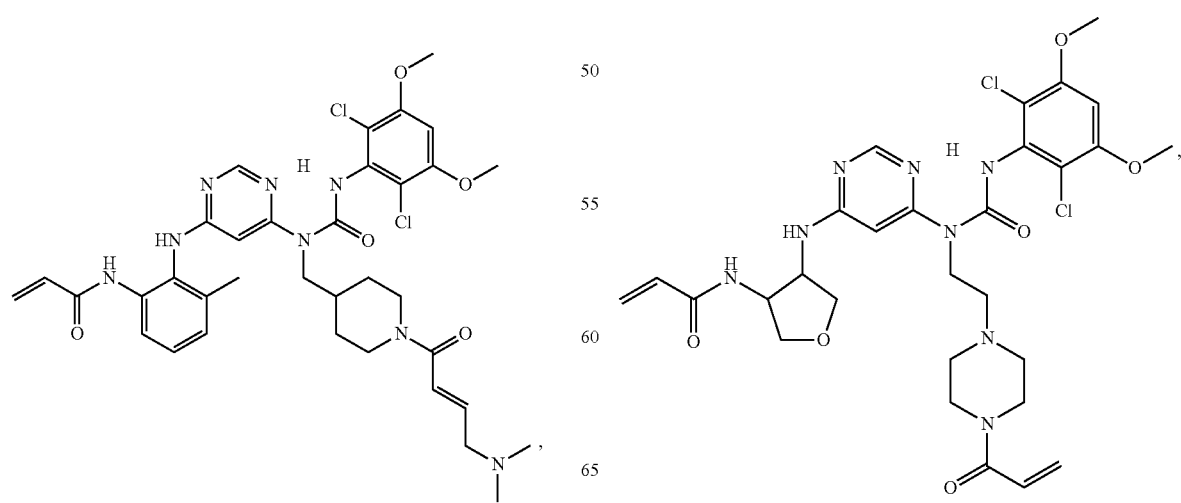

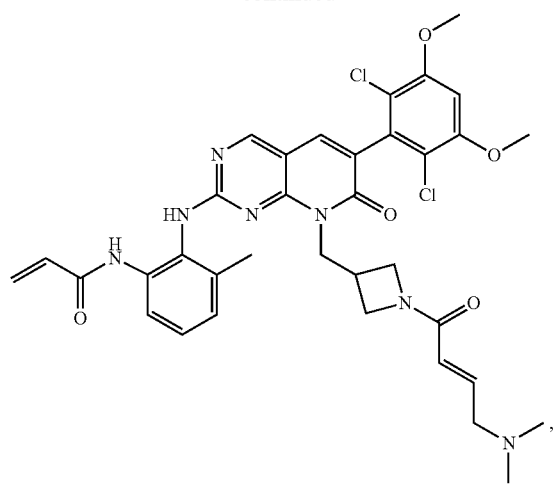
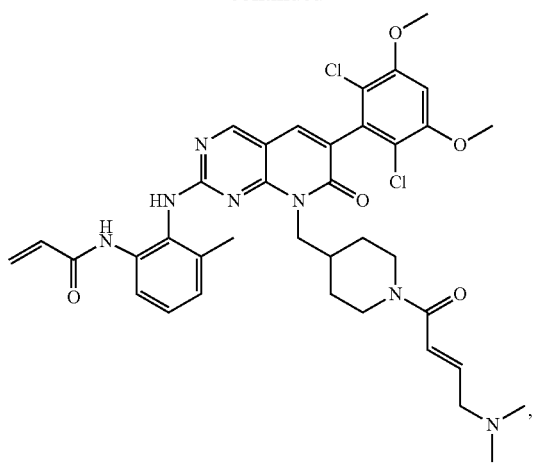
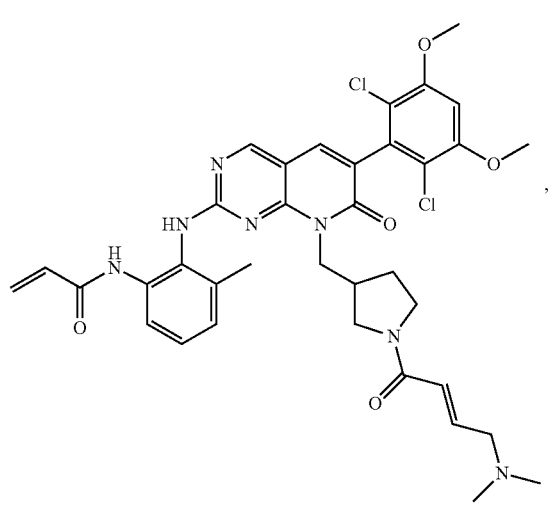
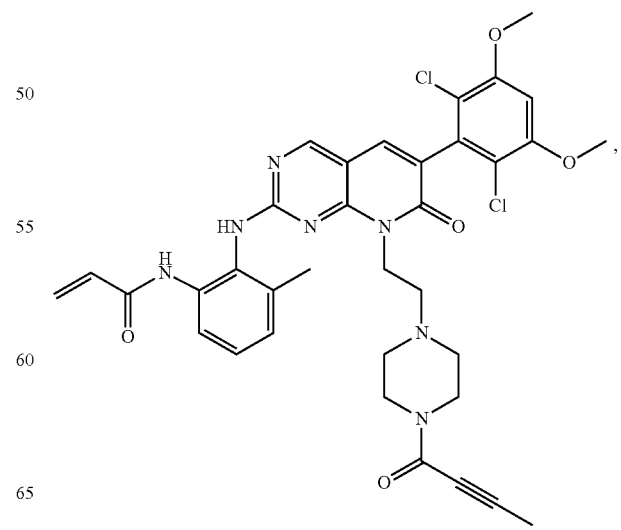

25
-continued
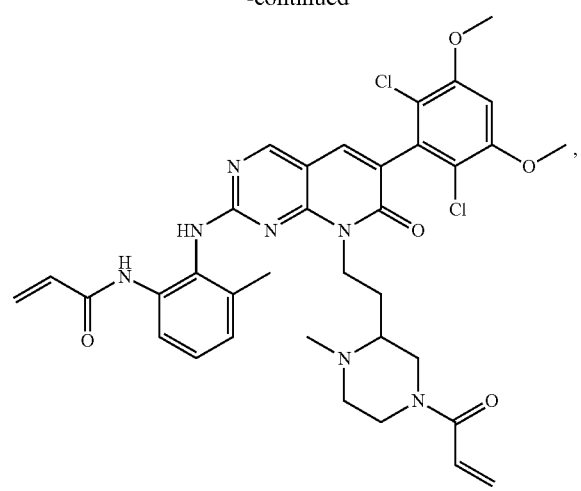
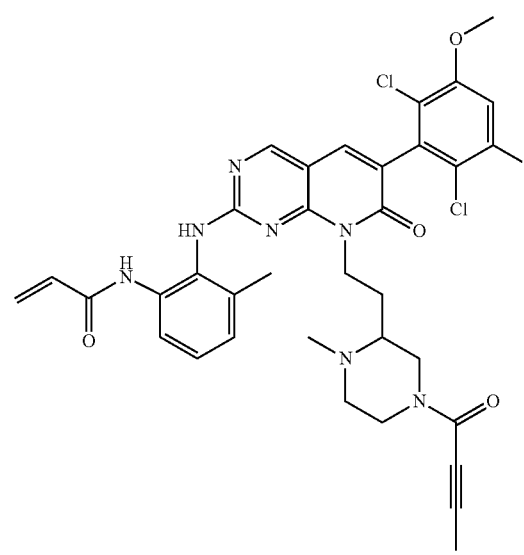
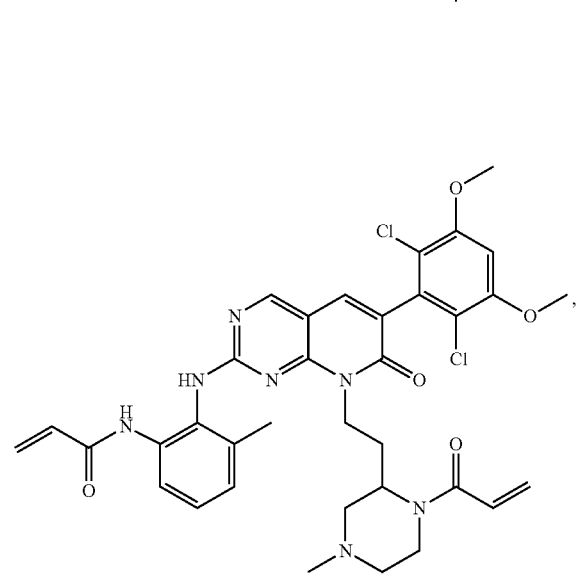
26
-continued
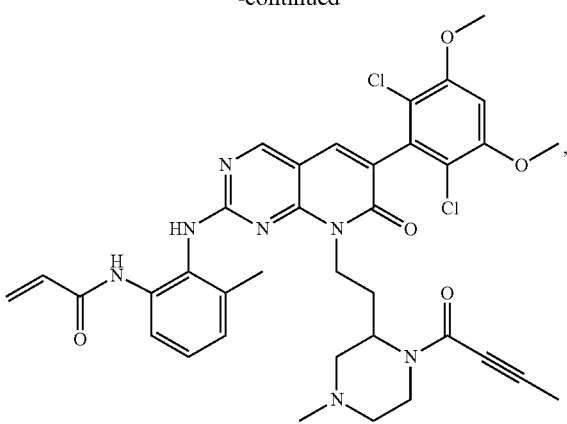
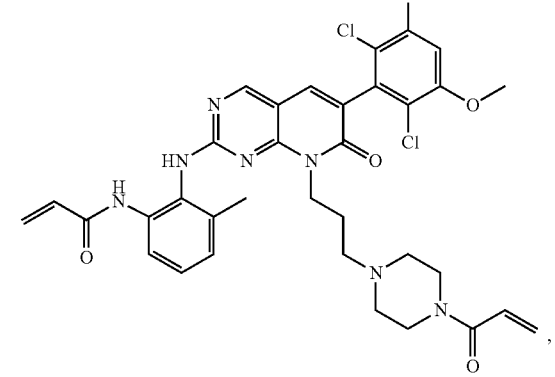
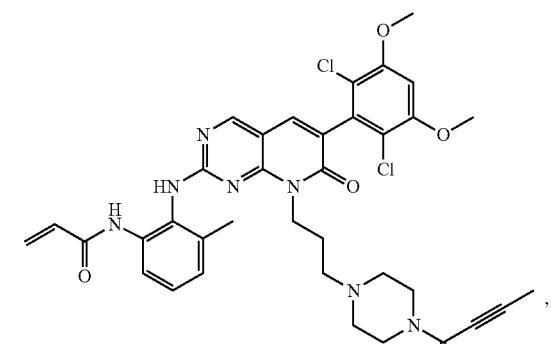
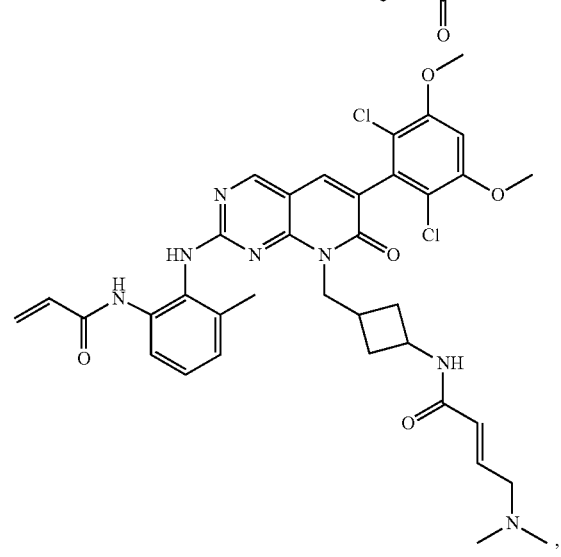

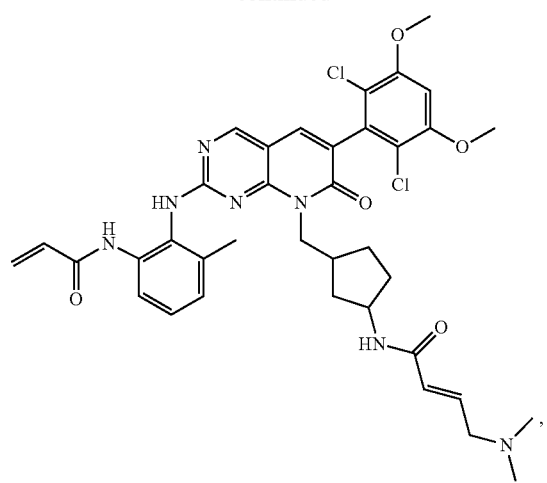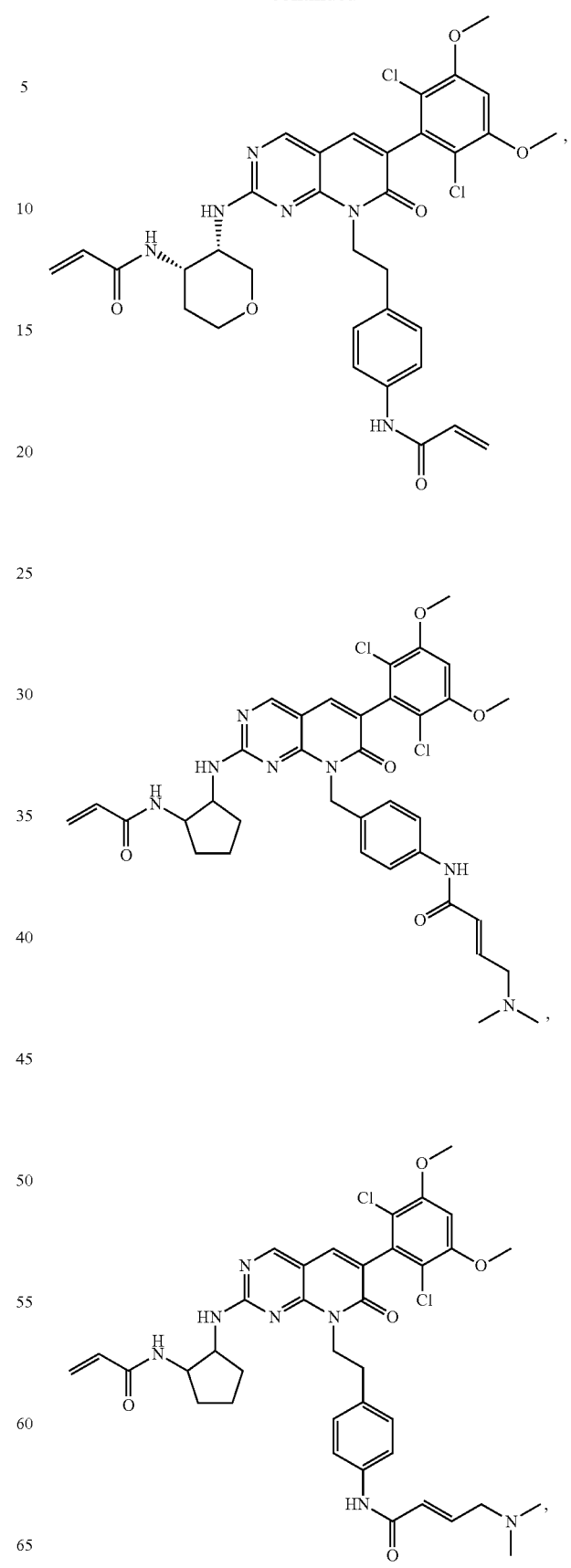

29
-continued
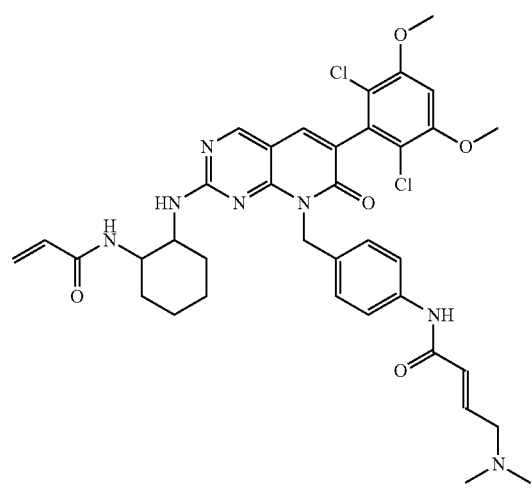
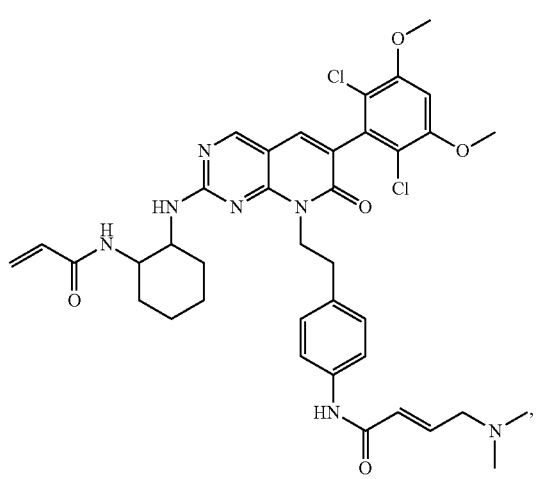
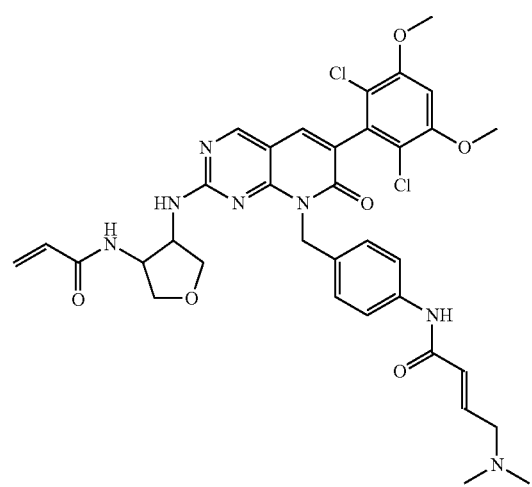
30
-continued
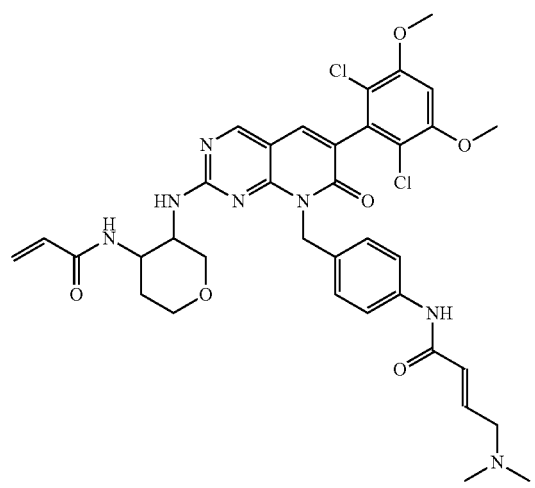
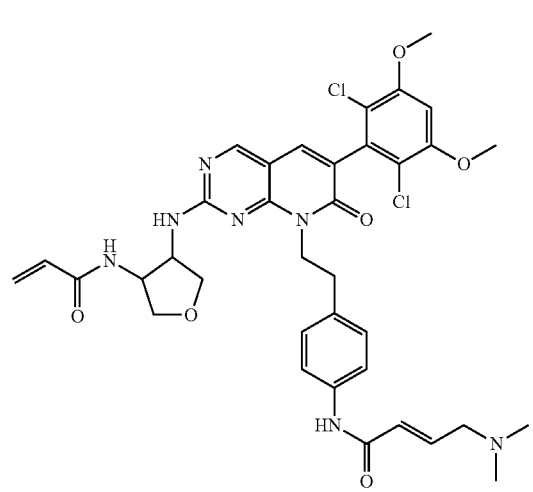

31
-continued
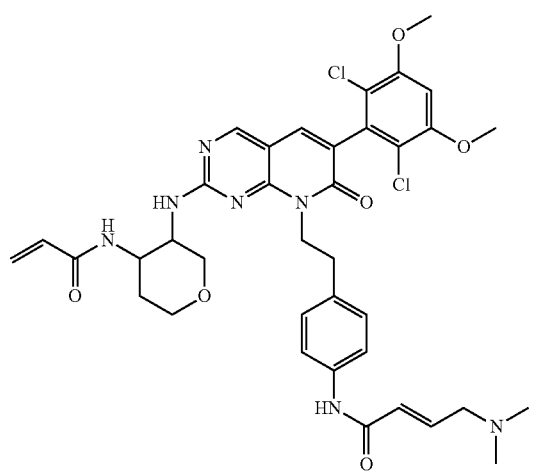
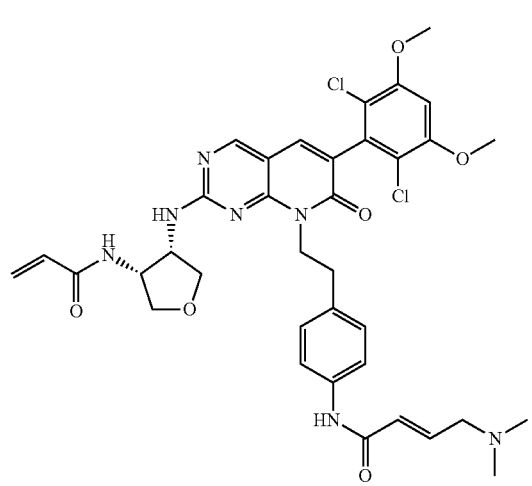
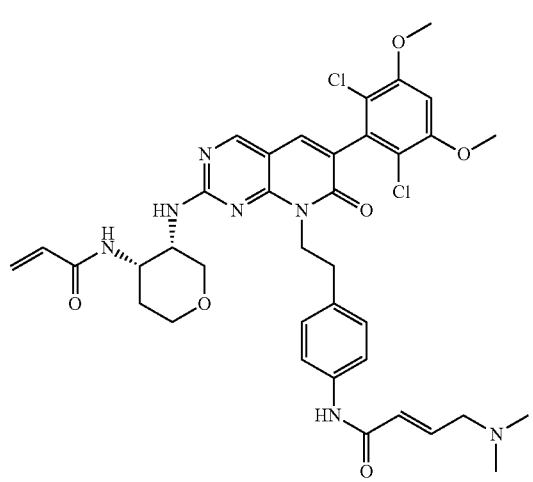
32
-continued
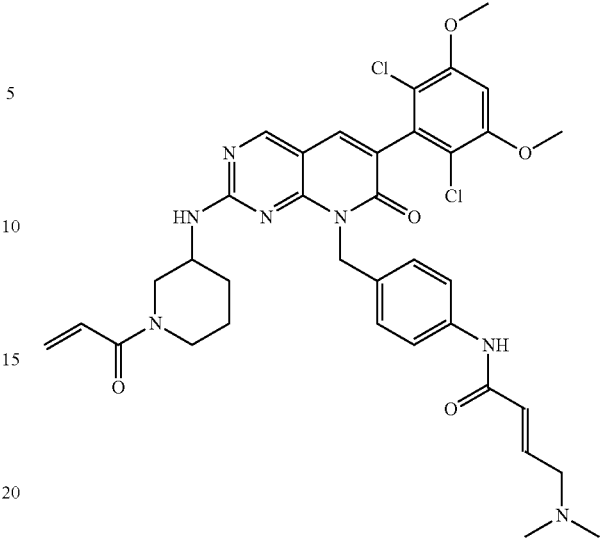

33
-continued
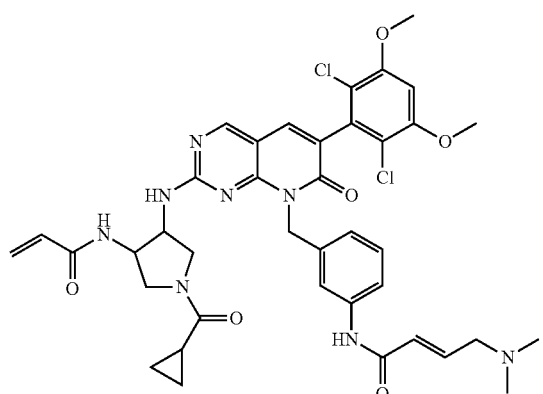
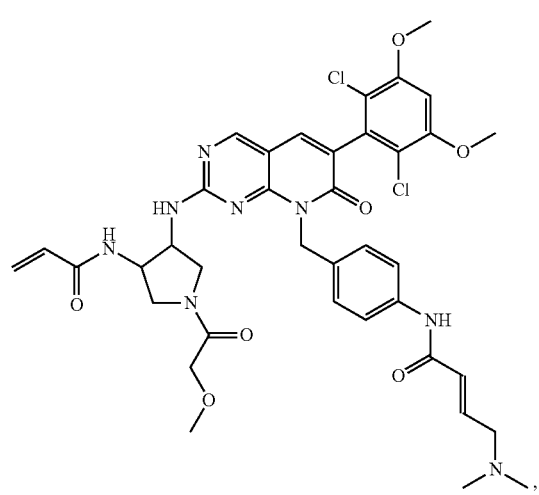
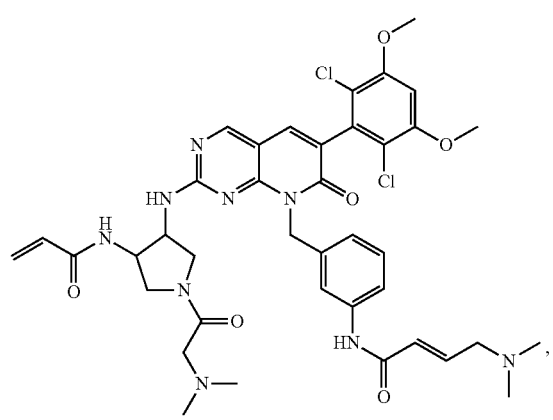
34
-continued
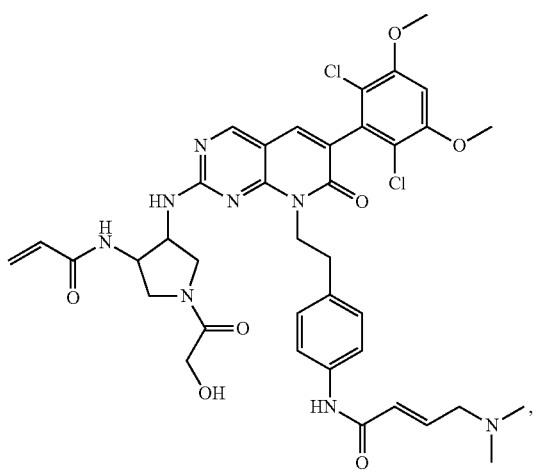
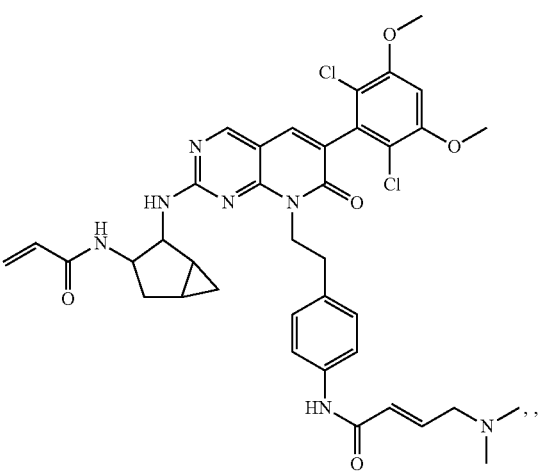
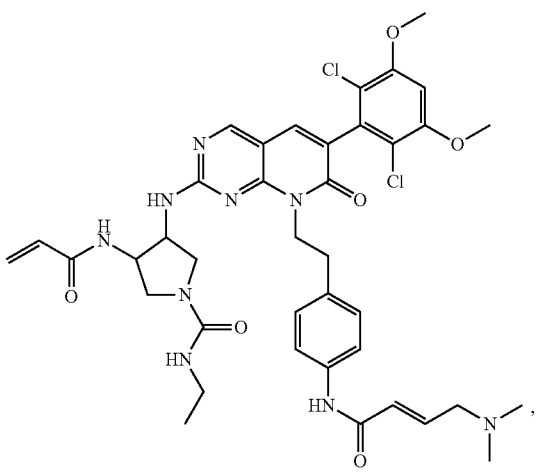

35
-continued
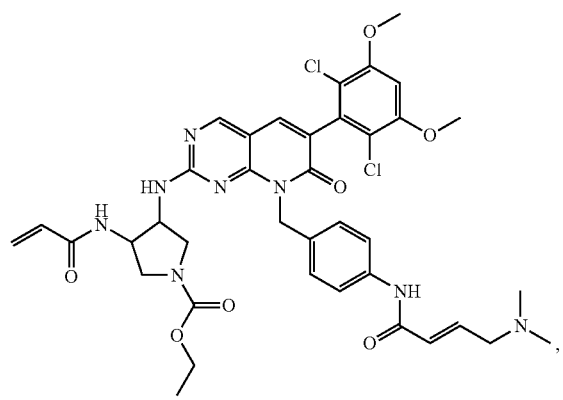
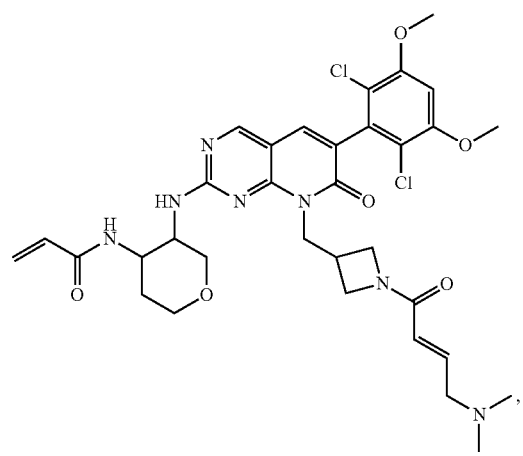
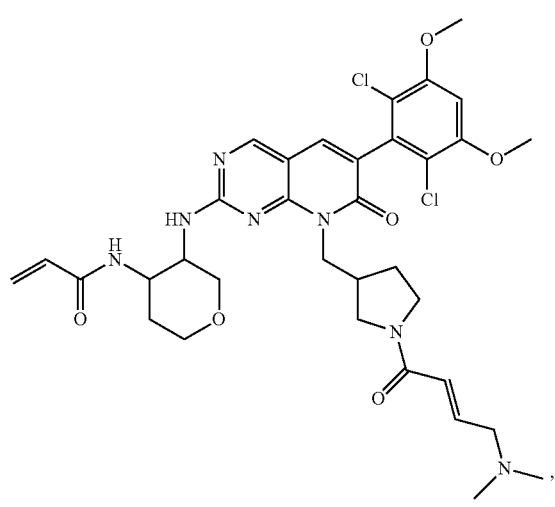
36
-continued
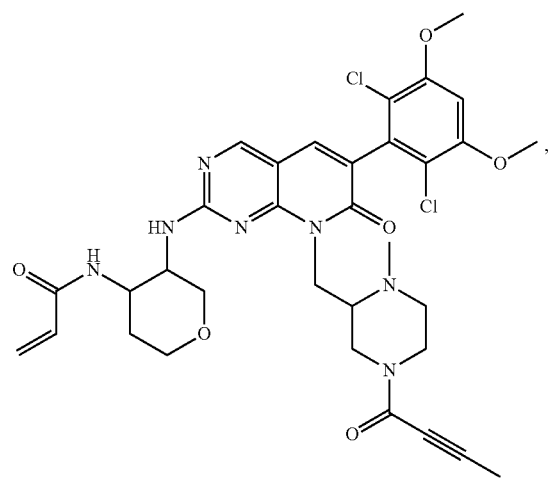
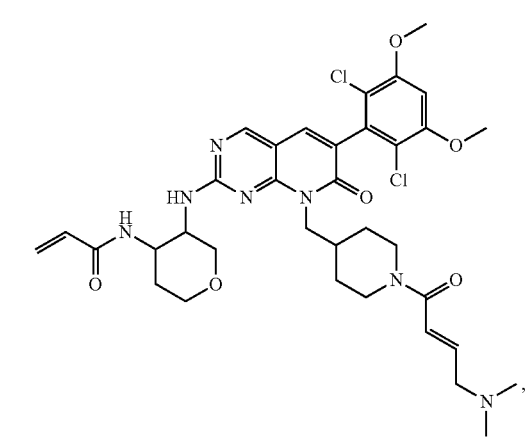
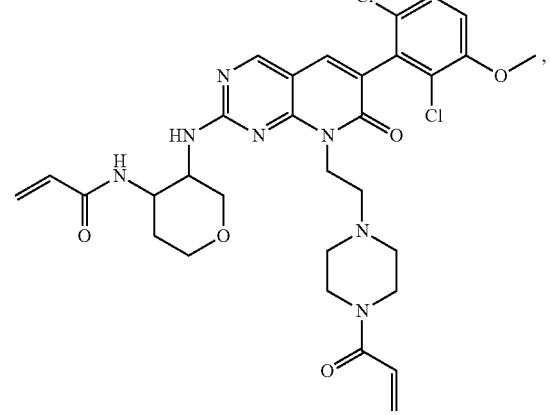

37
-continued
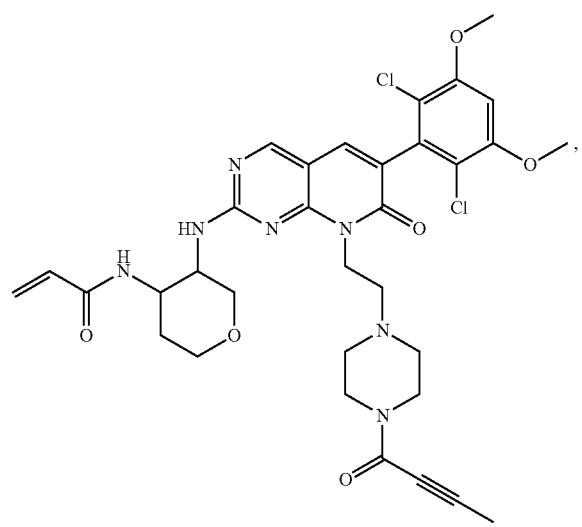
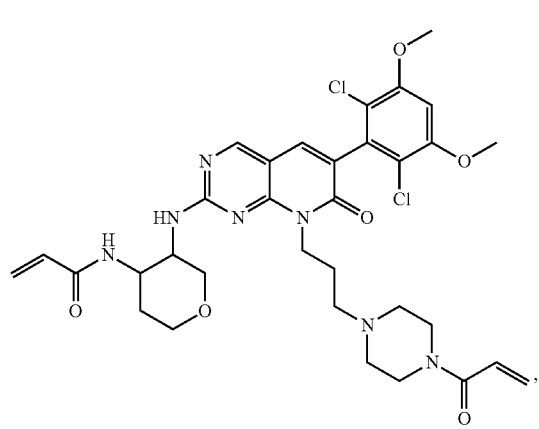
38
-continued
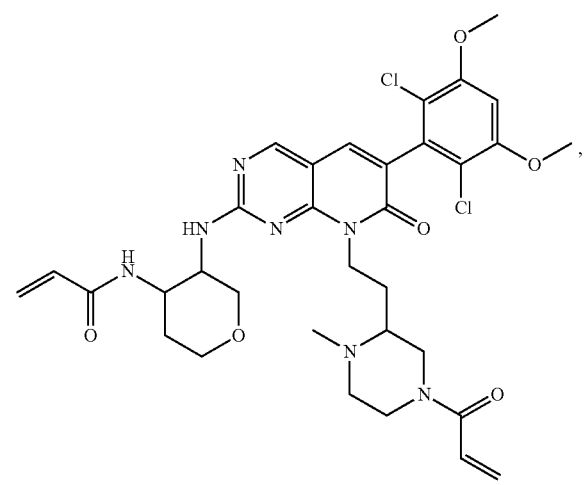
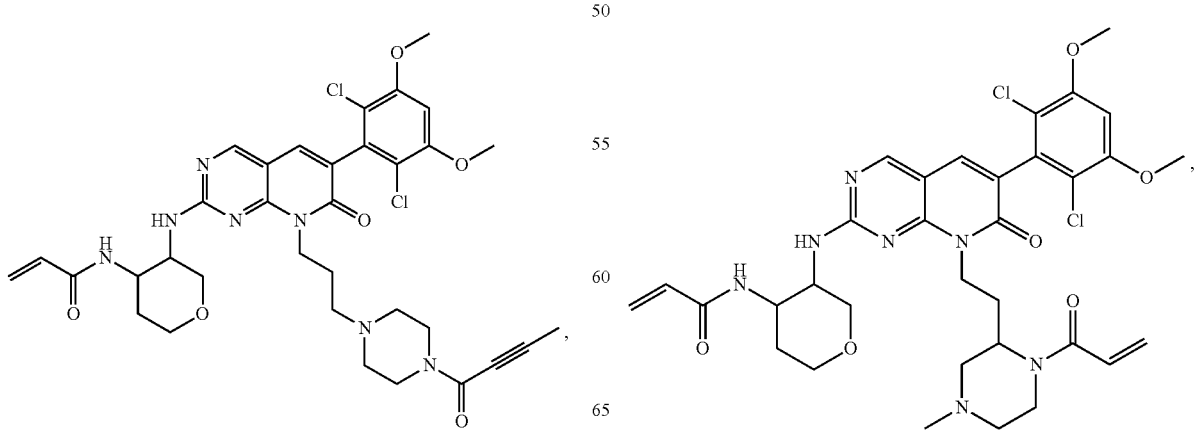

-continued
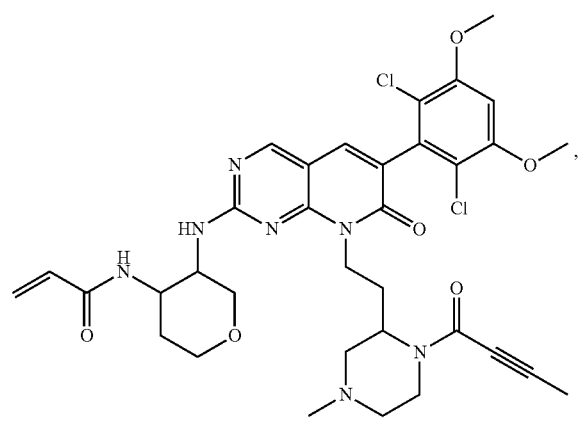
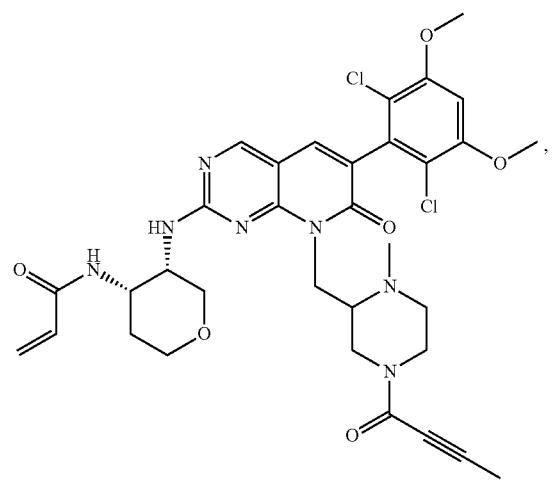
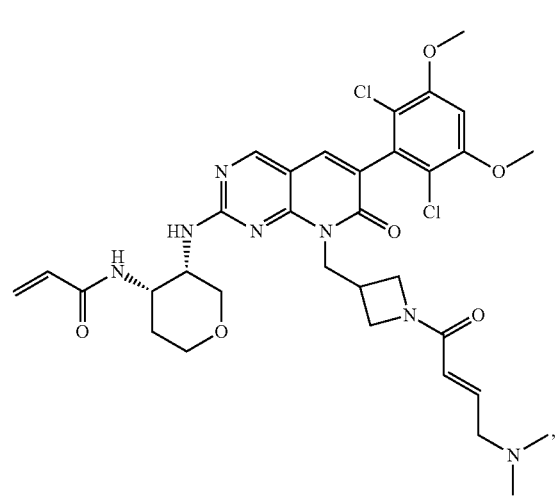
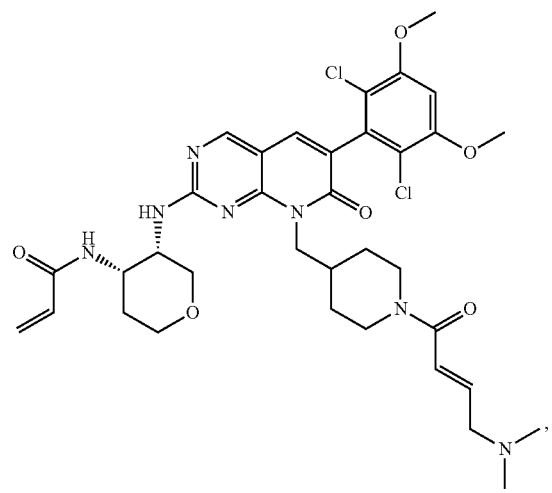
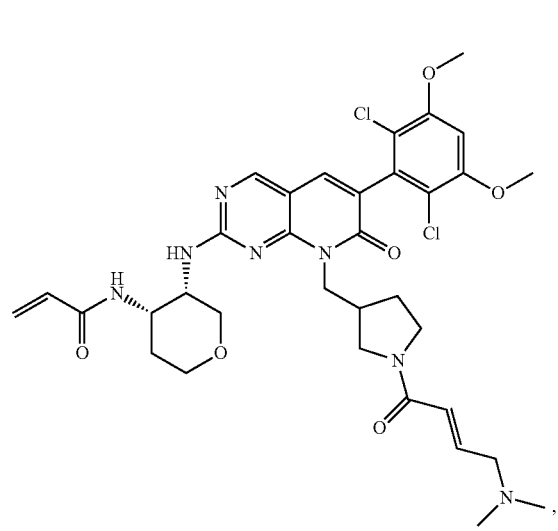
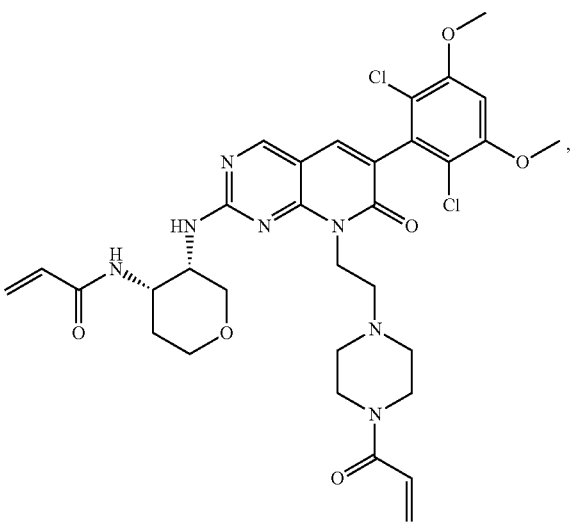

41
-continued
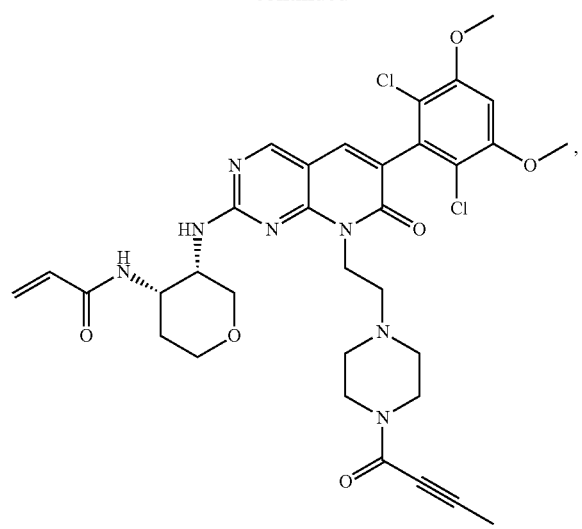
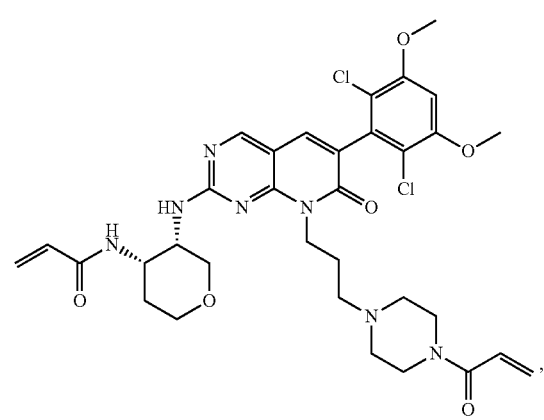
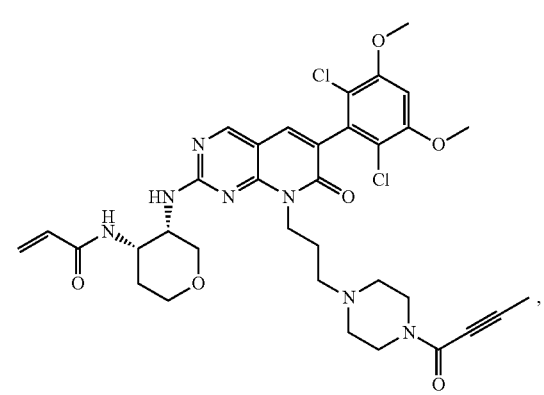
42
-continued
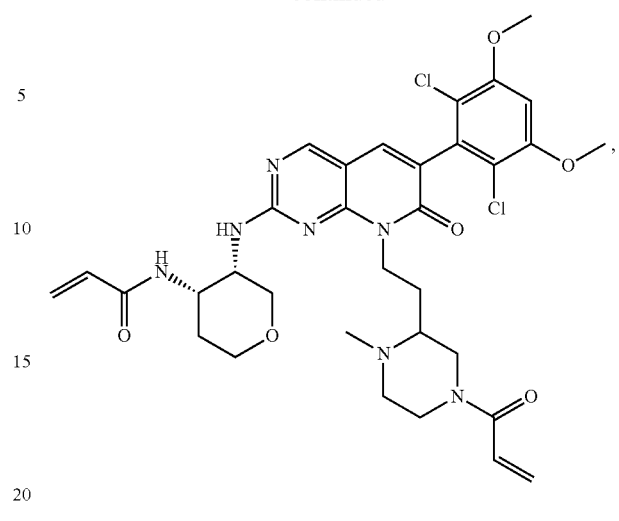
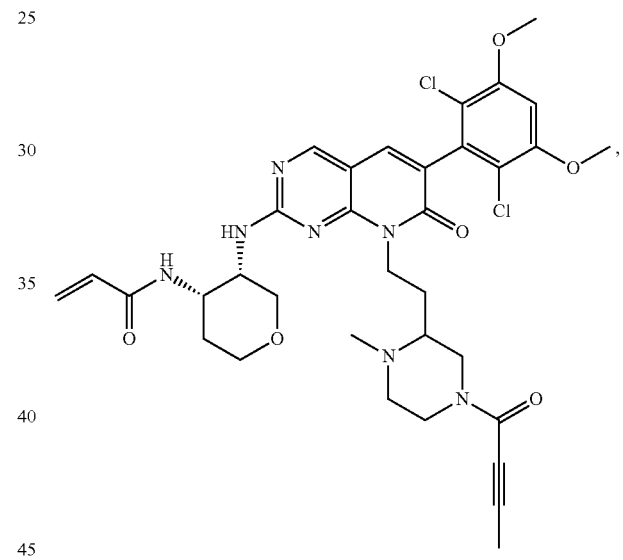
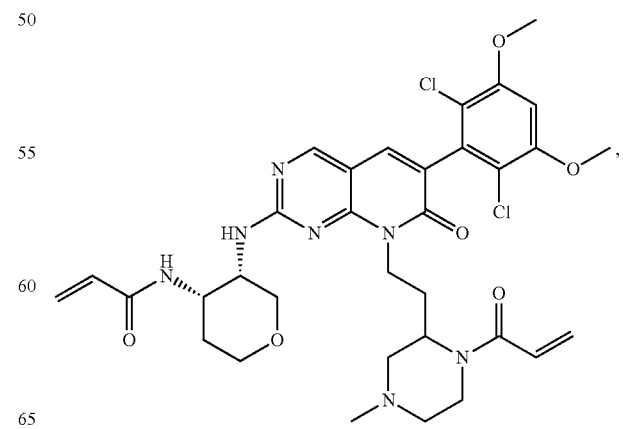

43
-continued
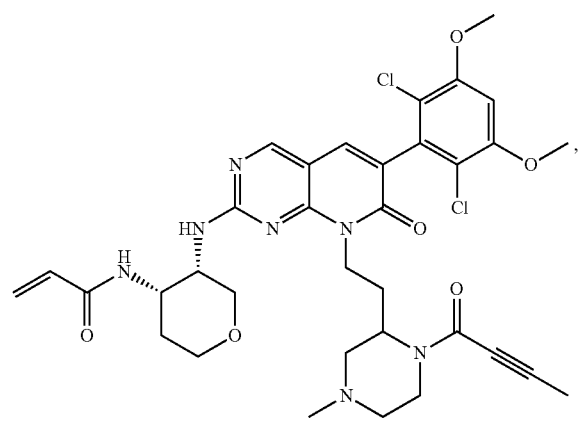
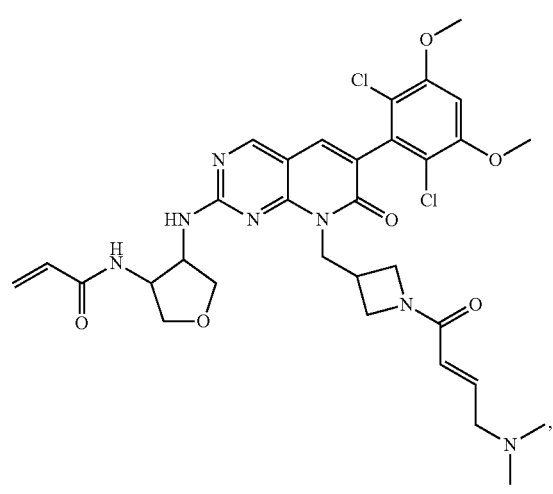
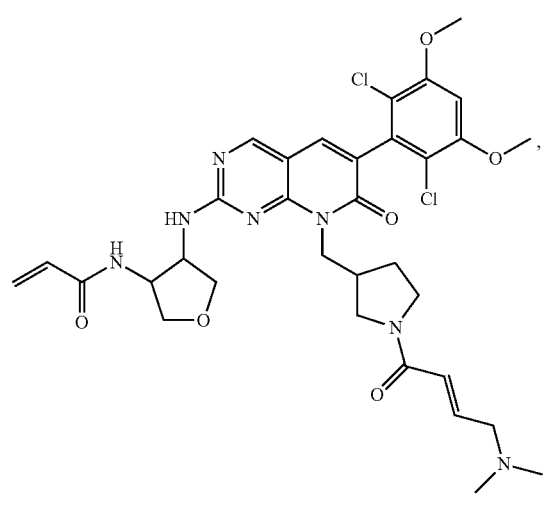
44
-continued
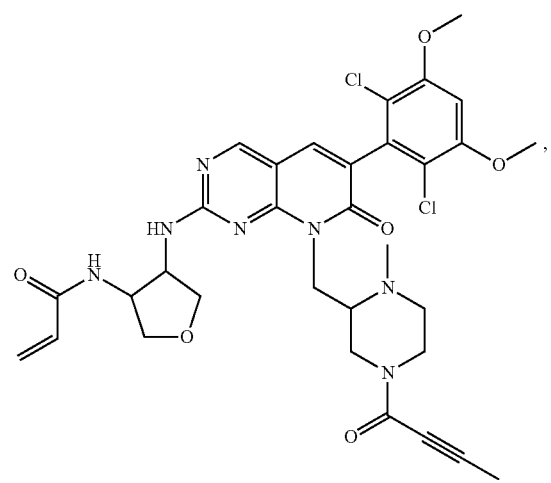
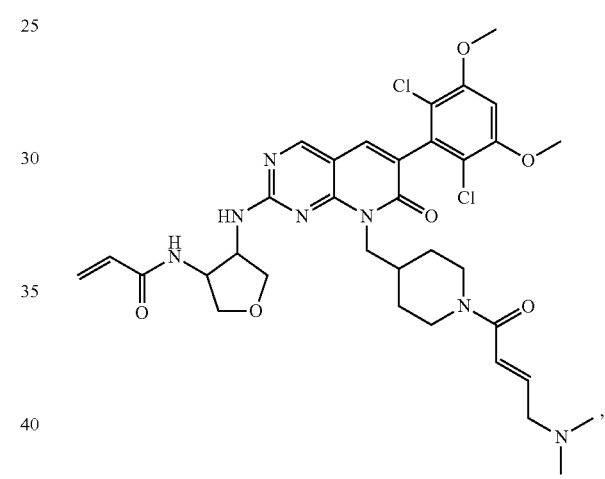
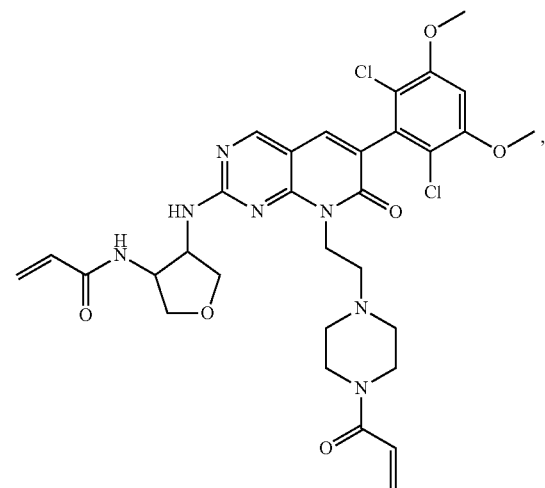

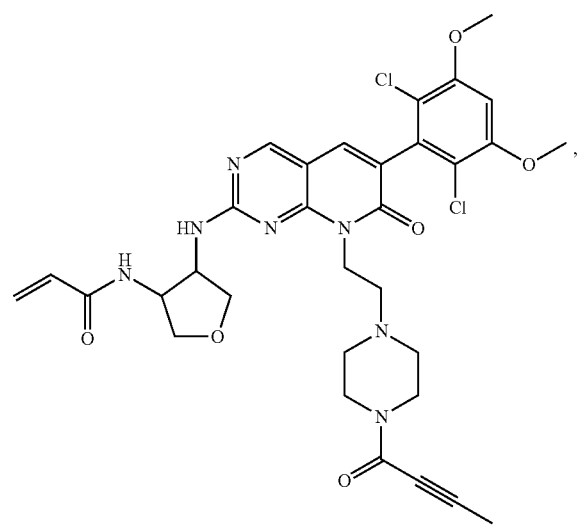
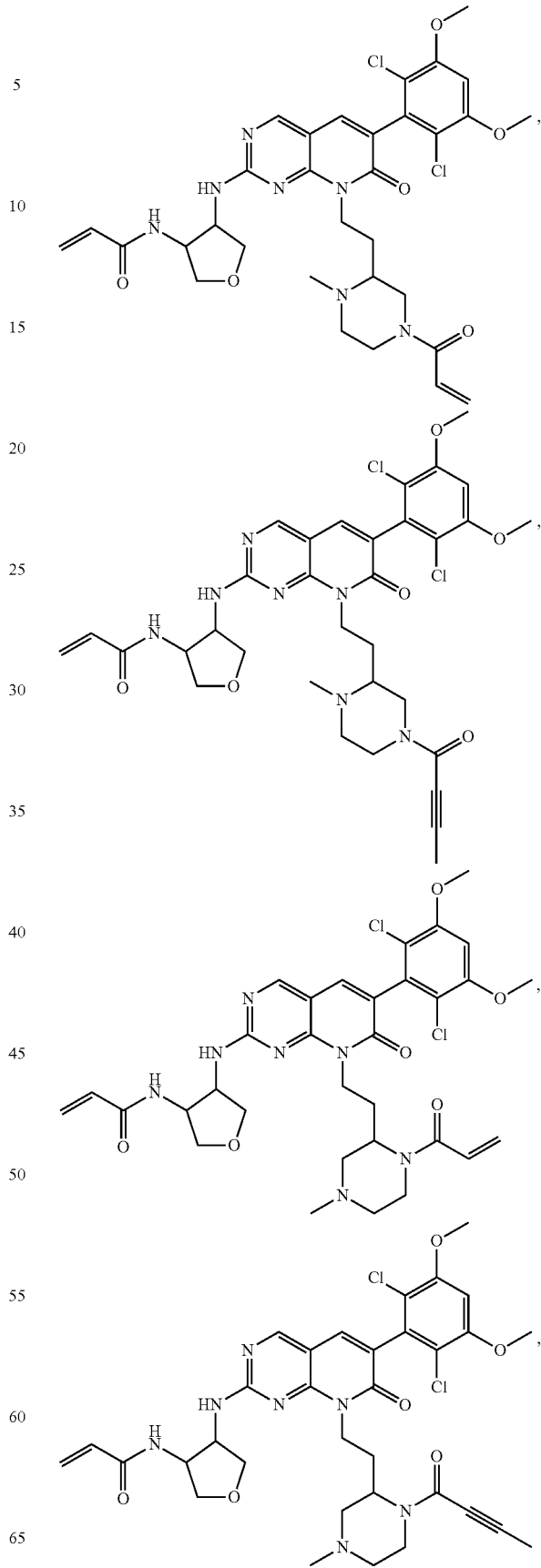

47
-continued
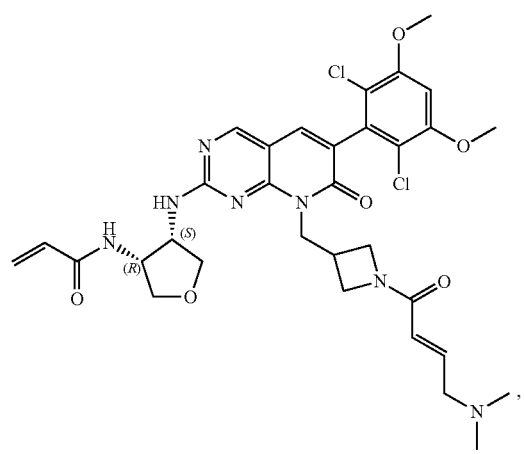
48
-continued
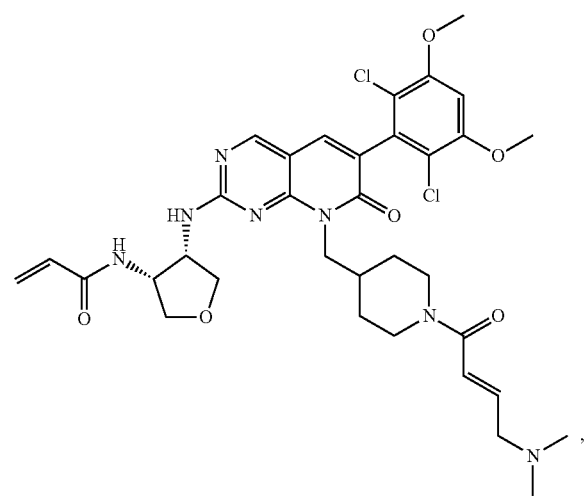
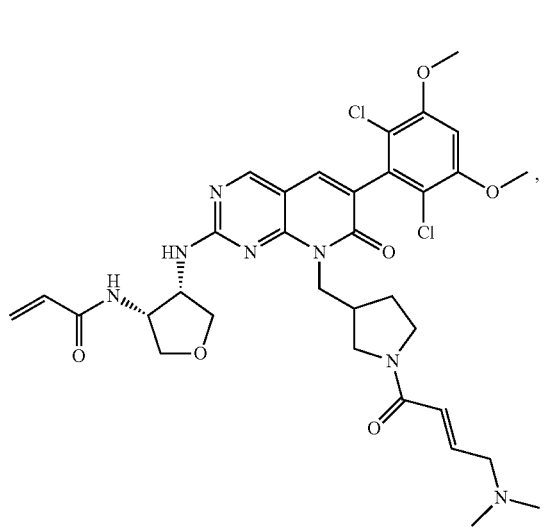
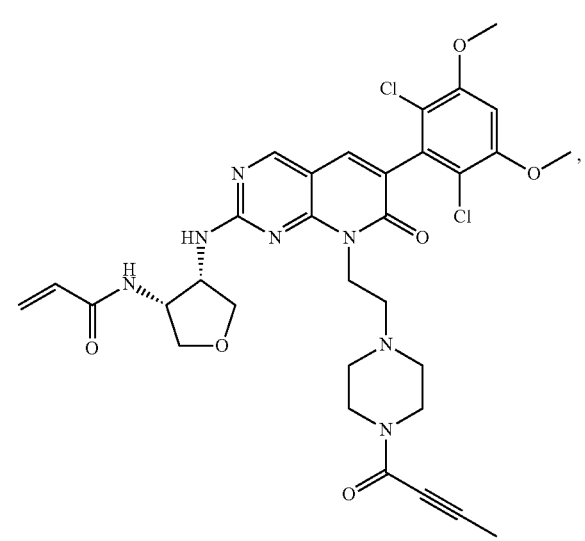
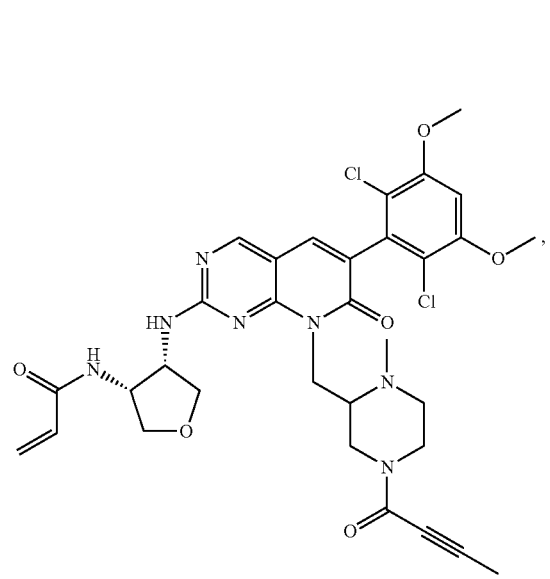

49
-continued
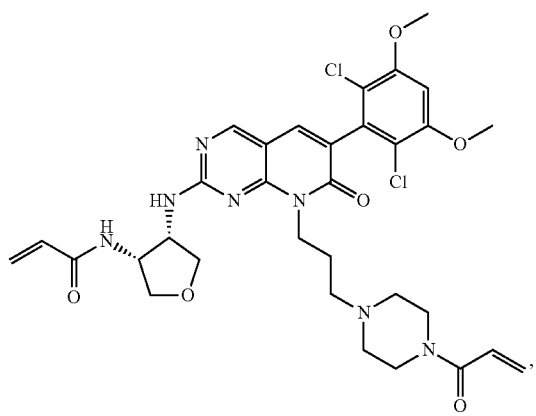
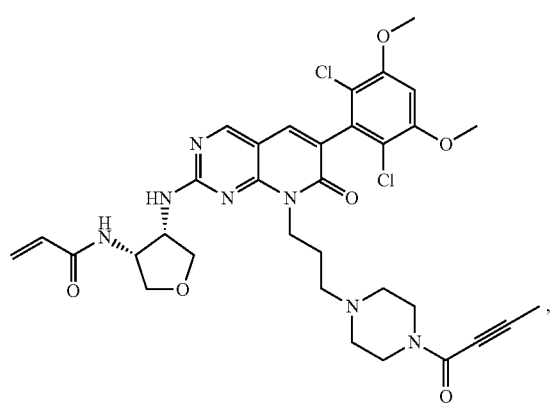
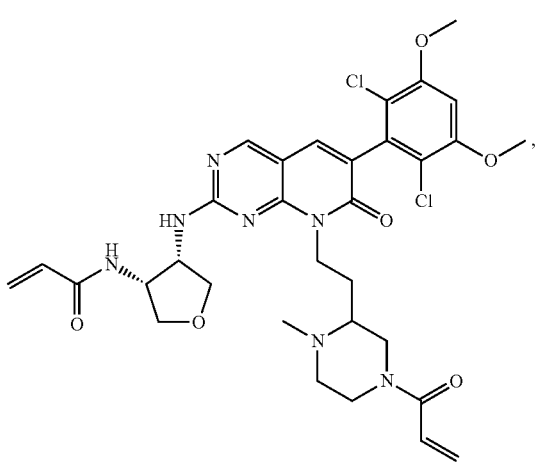
50
-continued
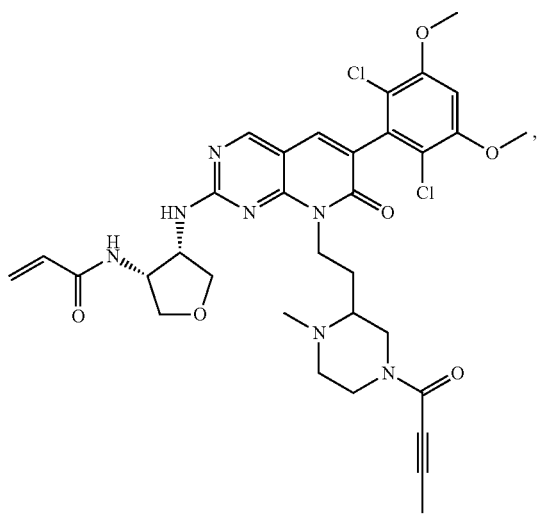
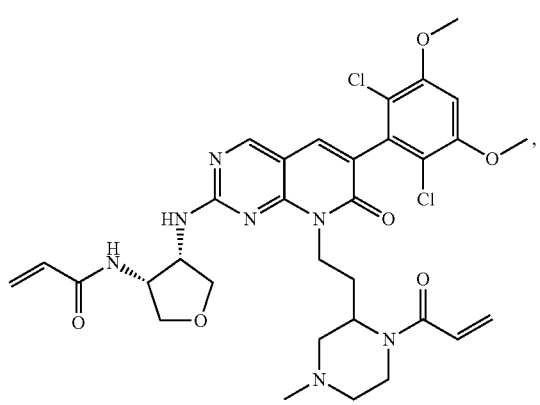
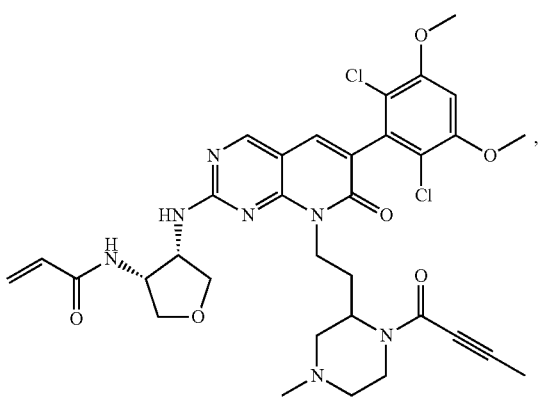

51
-continued
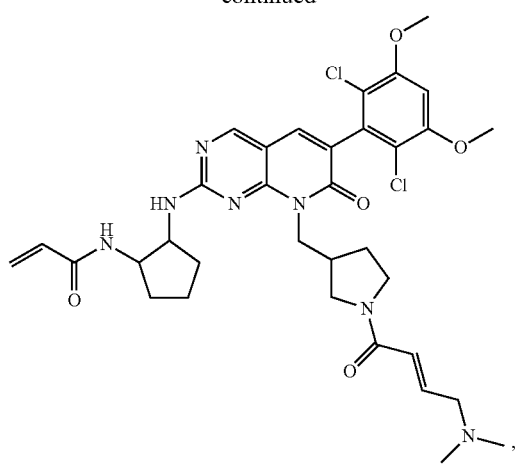
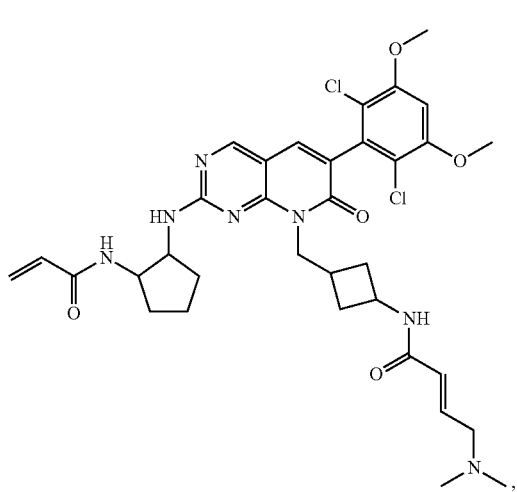
52
-continued
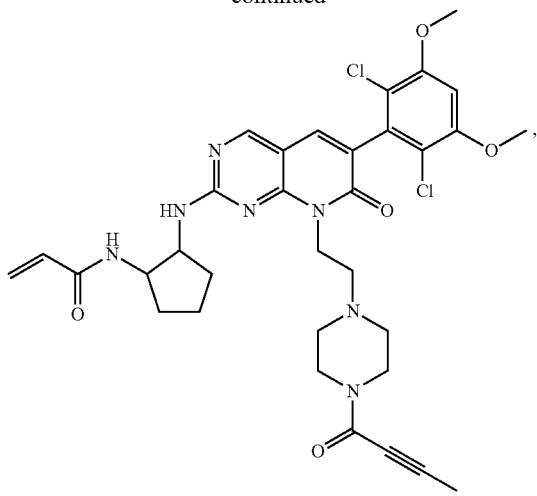
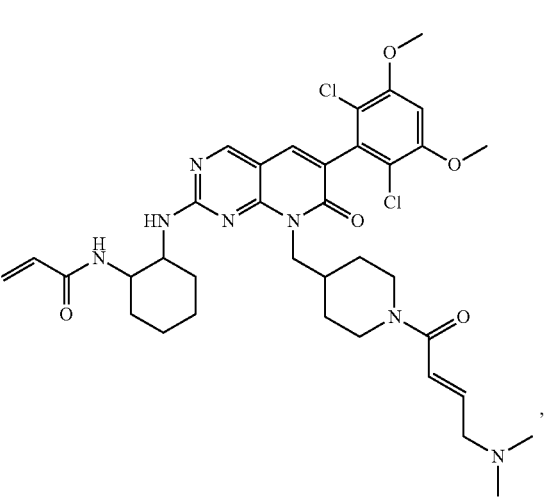

53
-continued
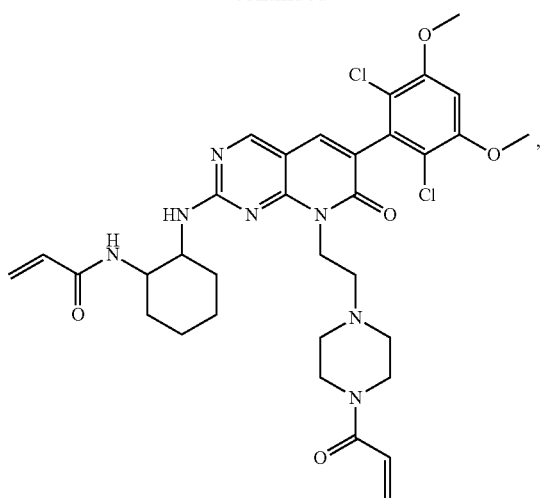
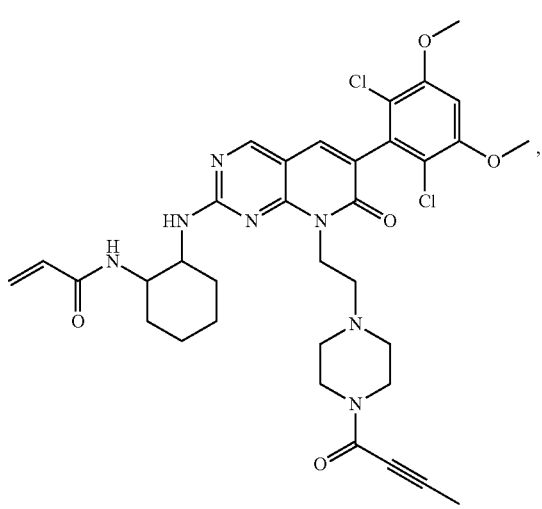
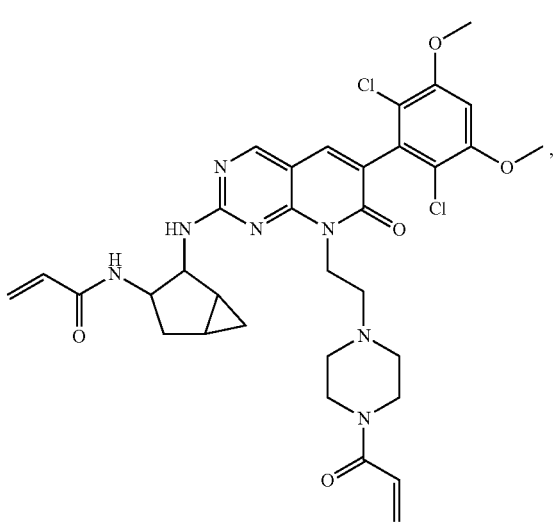
54
-continued
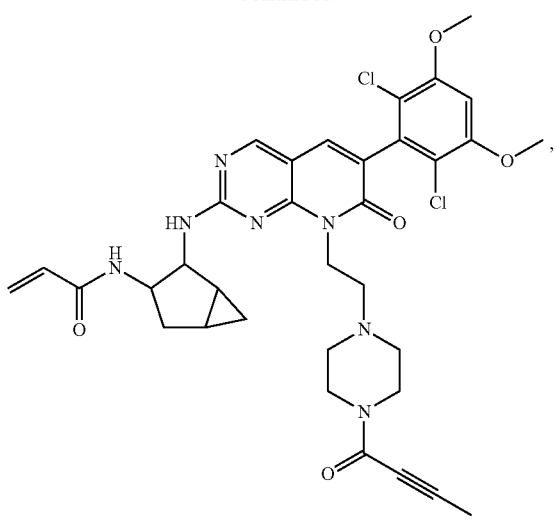
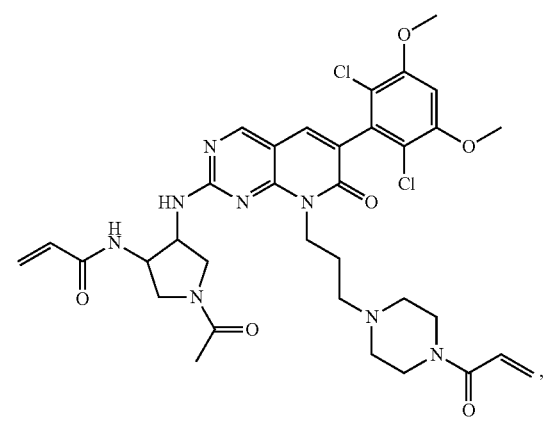
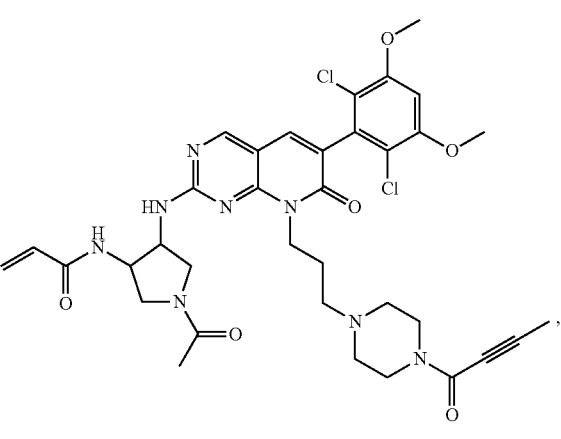

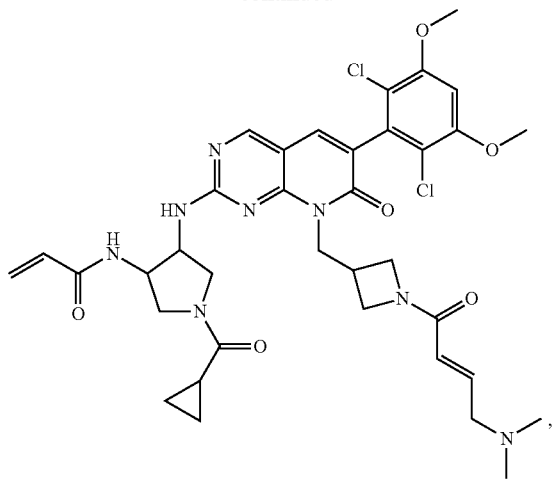

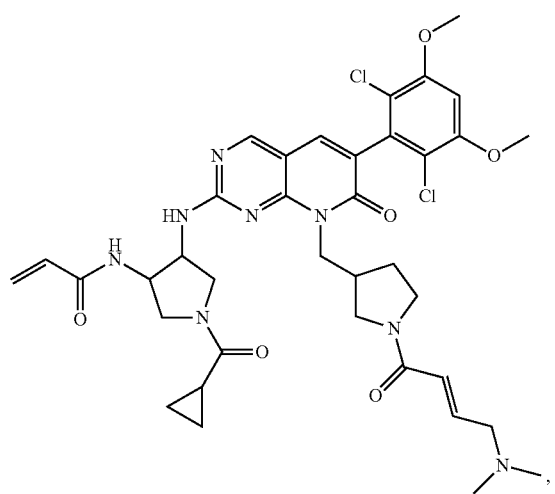

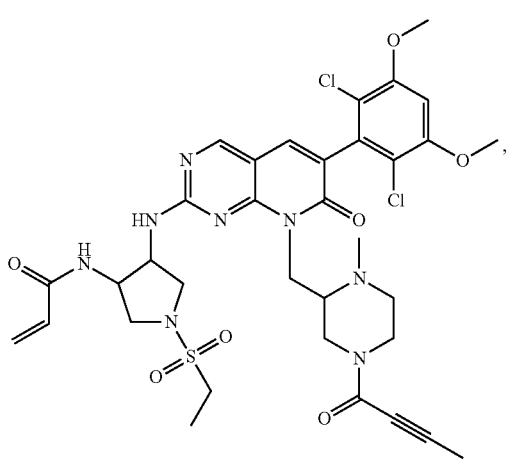

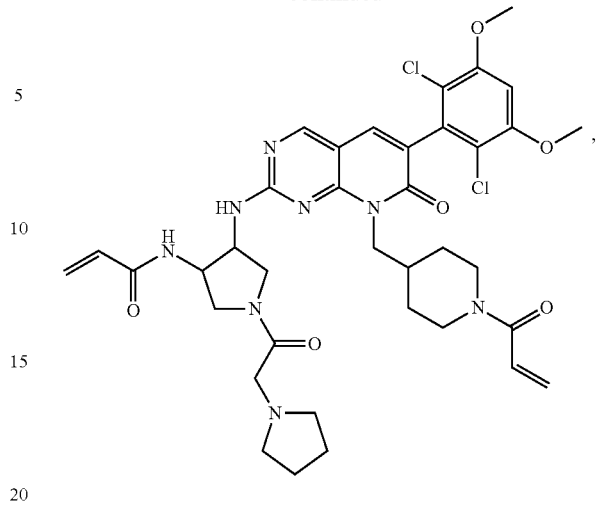

The invention also provides an N-oxide of any of the compounds of the invention, or a pharmaceutically acceptable salt, solvate, polymorph, tautomer, stereoisomer, an isotopic form, or a prodrug thereof.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery*, 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters*, 1994, Vol. 4, p. 1985.

Deuterium-enriched compounds: deuterium (D or $^2H$) is a stable, non-radioactive isotope of hydrogen and has an atomic weight of 2.0144. Hydrogen naturally occurs as a mixture of the isotopes $^xH$ (hydrogen or protium), D ($^2H$ or deuterium), and T ($^3H$ or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as $(C_{1-4})$ alkyl halides, e.g., methyl, ethyl, iso-propyl and tert-butyl chlorides, bromides and iodides; di-$(C_{1-4})$ alkyl sulfates, e.g., dimethyl, diethyl and diamyl sulfates; alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs (*Mol. Cancer Therapy*, 2004 Mar. 3(3):233-244). Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example, by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g., benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NR$_a$R$_b$ where R$_a$ and R$_b$ are each independently two further substituents where a hydrogen or carbon atom is alpha to the nitrogen. It is noted that carbamoyl moieties may include protected derivatives thereof.

Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —NO$_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, *Protecting Groups in Organic Synthesis*, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Pseudo-bicyclic" means a nonvalent intramolecular hydrogen bonds lock the conformation of a molecule to forms a "pseudo-ring".

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1 (M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDGFRa(D842V), PDGFRa(T674I), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g., Bcl-xL, Bcl-2, Bcl-w), histone deacetylases (HDAC), histone acetyltransferases (HAT), and methyltransferase (e.g., histone lysine methyltransferases, histone arginine methyltransferase, DNA methyltransferase, etc.).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), antibody conjugate (e.g., brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc.).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, kinase inhibitors, epigenetic agents, HSP90 inhibitors, PARP inhibitors, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

The invention further provides methods for the prevention or treatment of a neoplastic disease. In one embodiment, the invention relates to a method of treating a neoplastic disease, in a subject in need of treatment comprising administering to said subject a therapeutically effective amount of a compound of the invention. In one embodiment, the invention further provides for the use of a compound of the invention in the manufacture of a medicament for halting or decreasing a neoplastic disease.

In certain embodiments, the neoplastic disease is a lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

It should be understood that the invention is not limited to the particular embodiments shown and described herein, but that various changes and modifications may be made without departing from the spirit and scope of the invention as defined by the claims.

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of key intermediate 1-6 is described in Scheme 1. $R_3$, $R_4$, $R_5$, and $R_6$ in Scheme 1 are the same as those described in the Summary section above.

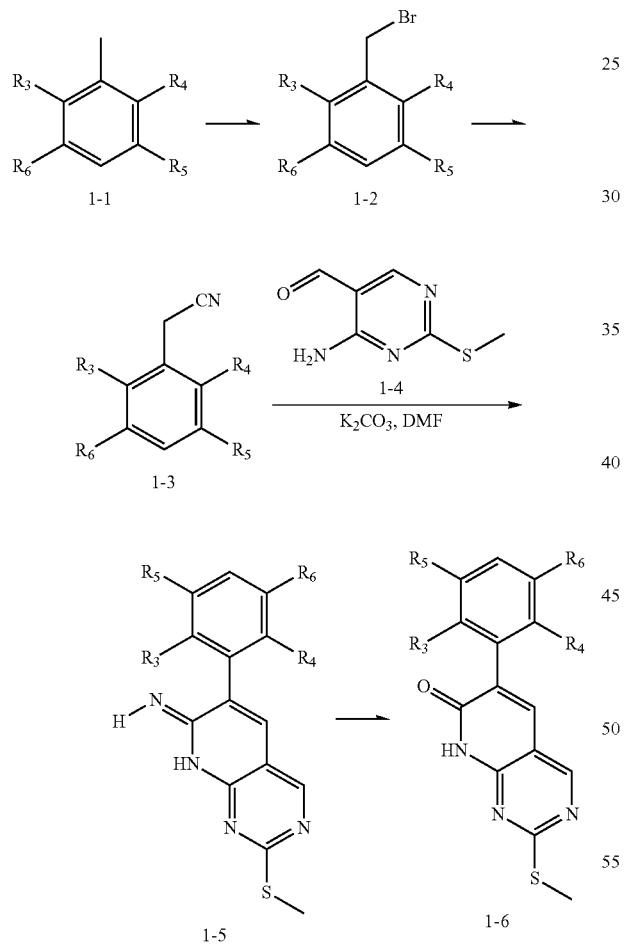

In Scheme 1, substituted toluene 1-1 is brominated to give benzyl bromide 1-2, which is further substituted to benzyl nitrile 1-3. Condensation of 1-3 and anilino aldehyde 1-4 yields bicyclic intermediate 1-5, which upon hydrolysis gives pyrimido-pyridone 1-6.

A typical approach to synthesize of Formular (II) compounds in which $Z_1$ is —$(CH_2)_m$—, $Z_2$ is NH, $Z_3$ is NH, and $Z_4$ is NH, is described in Scheme 2. Warhead1, Warhead2, $R_3$, $R_4$, $R_5$, $R_6$, $R_7$, $R_8$, A, B, p, q, $Z_3$, and $Z_4$ in Scheme 2 are the same as those described in the Summary section above.

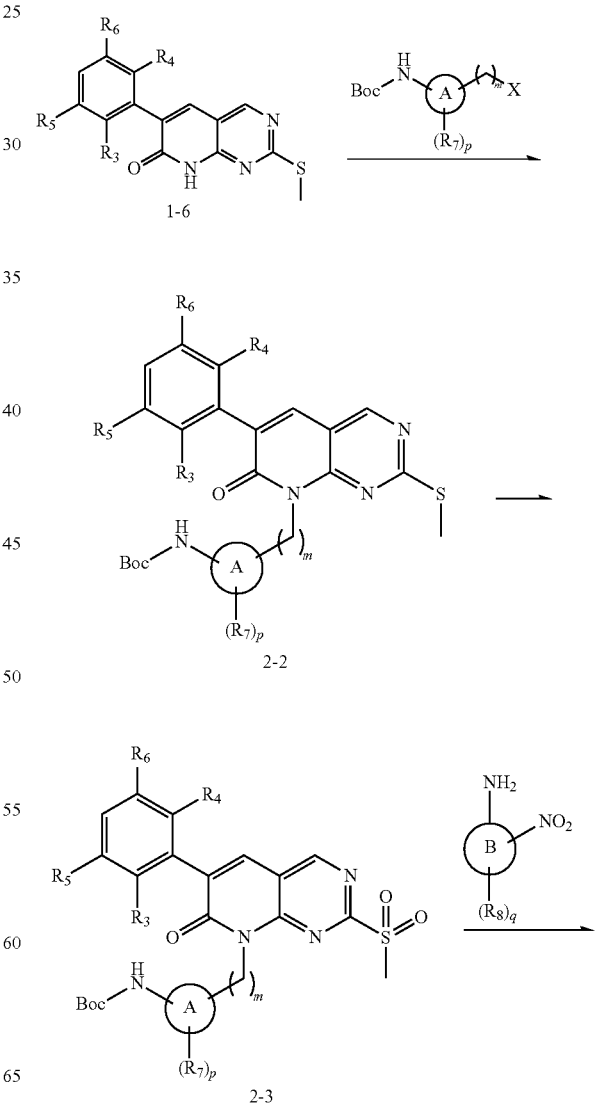

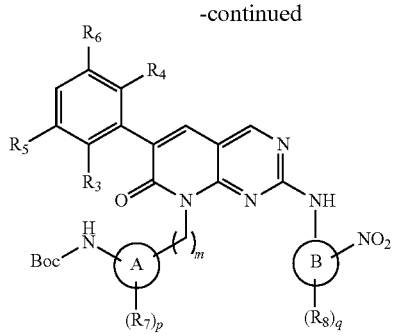

2-4

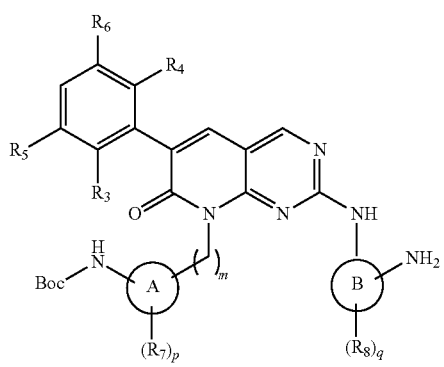

2-5

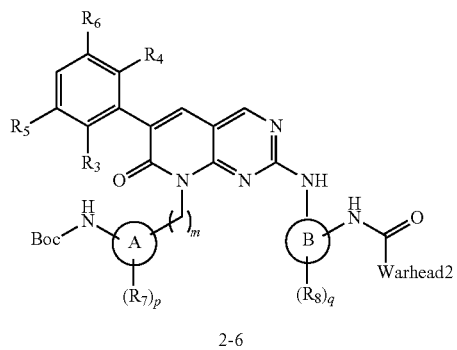

2-6

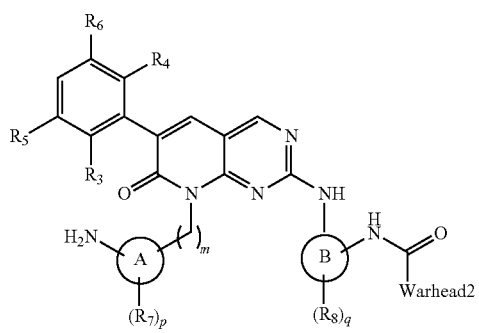

2-7

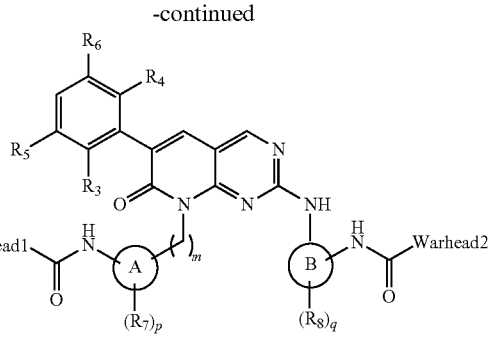

Formula (II)

In Scheme 2, the intermediate 1-6 can be alkylated to give intermediate 2-2, via either $S_N2$ substitution or Mitsunobu reaction. Subsequent oxidation leads to sulfone intermediate 2-3, which reacts with (o)-nitro anilines or (o)-NHBoc anilines to give 2-4. Reduction of $NO_2$ or de-Boc in 2-4 to $NH_2$ results in aniline 2-5. Amide coupling of 2-5 with corresponding acid or acid chloride to install Warhead2 group yields intermediate 2-6. Deprotection of Boc group of 2-6 results in amine intermediate 2-7. Coupling with corresponding acid or acid chloride to install Warhead1 group gives final compound with Formula (II).

Formular (I) compounds with Q of other 10 membered bicyclic heterocyclic such as

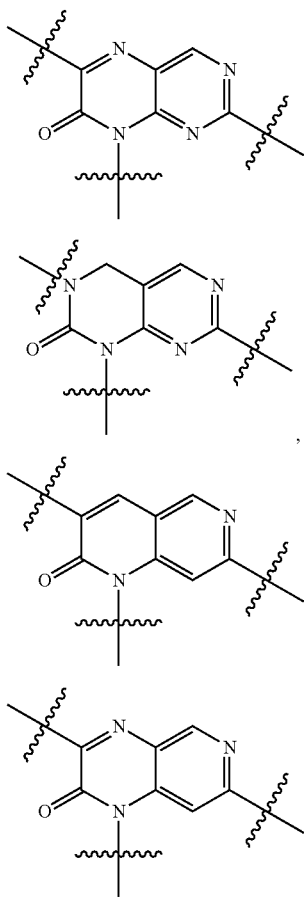

-continued

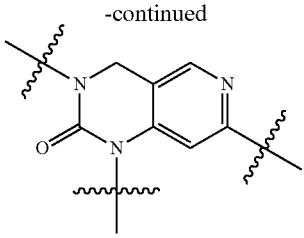

can be prepared by the schemes similar to Scheme 2 by using different starting materials similar to intermediate 1-6, for example,

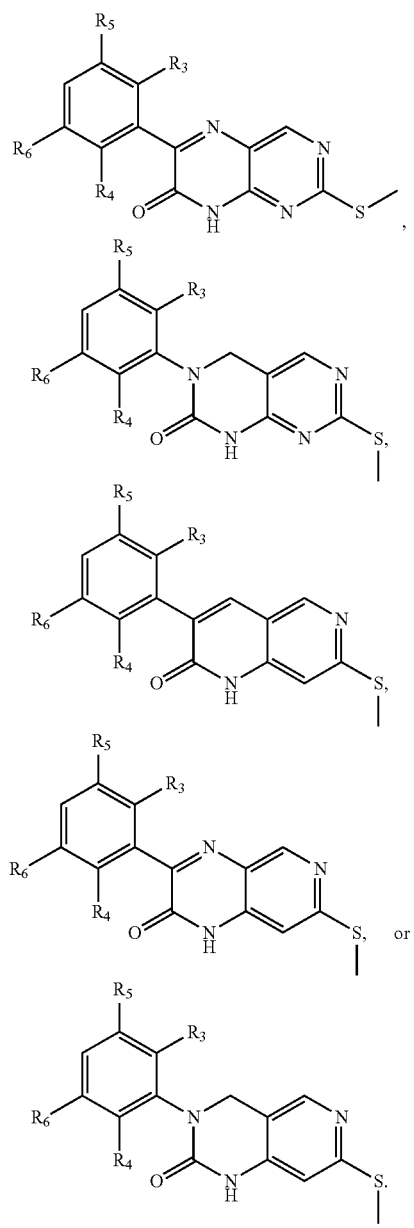

These intermediates can be prepared by the standard procedures of organic chemistry.

As a further example, a typical approach to synthesize of Formular (V-1) compounds

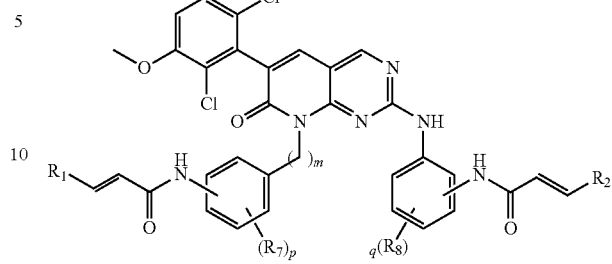

in which $R_1$ is equal to $R_2$ is described in Scheme A. m, p, q, $R_7$, and $R_8$ in Scheme A are the same as those described in the Summary section above.

Scheme A

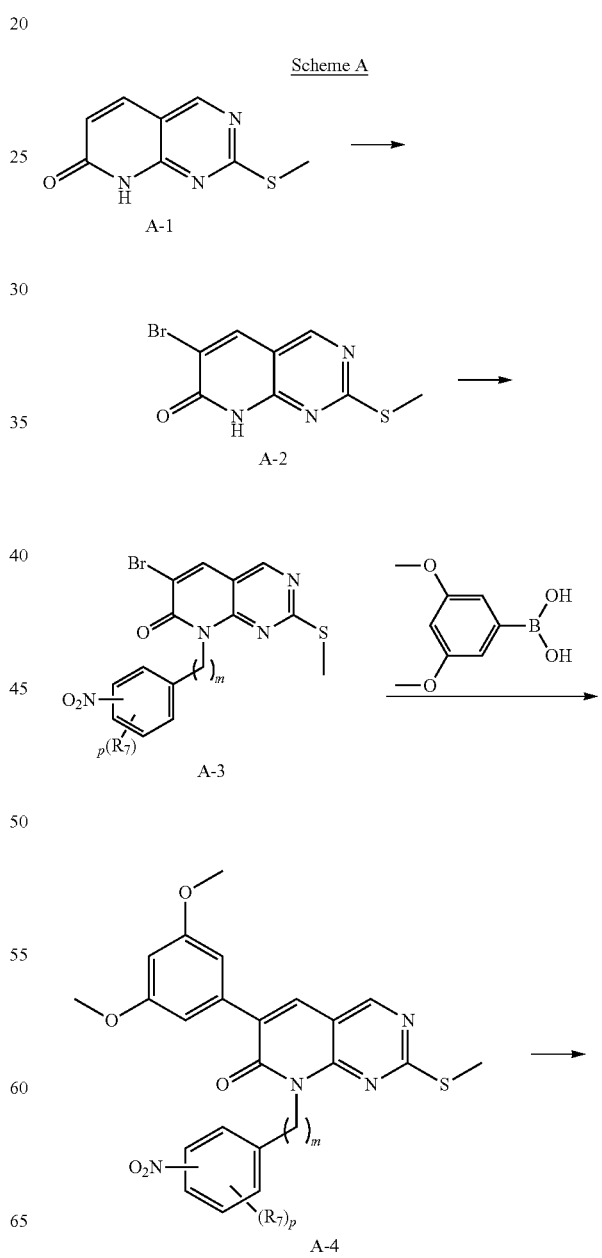

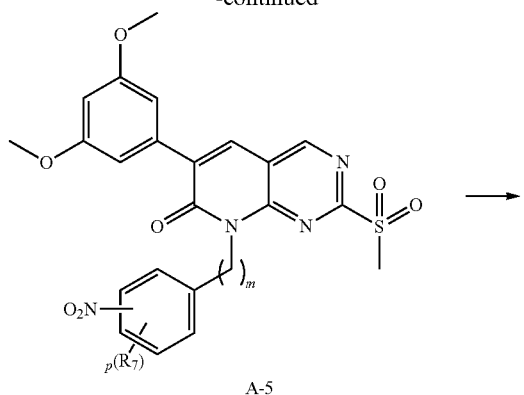

A-5

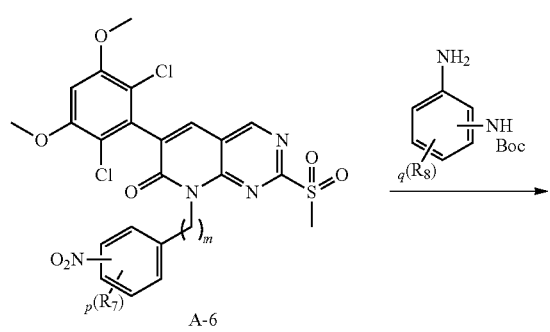

A-6

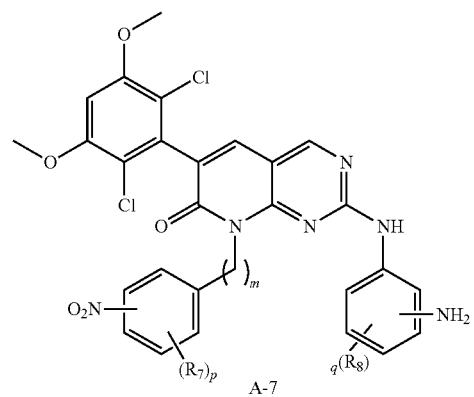

A-7

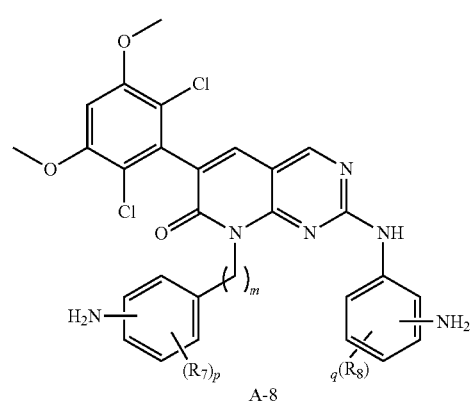

A-8

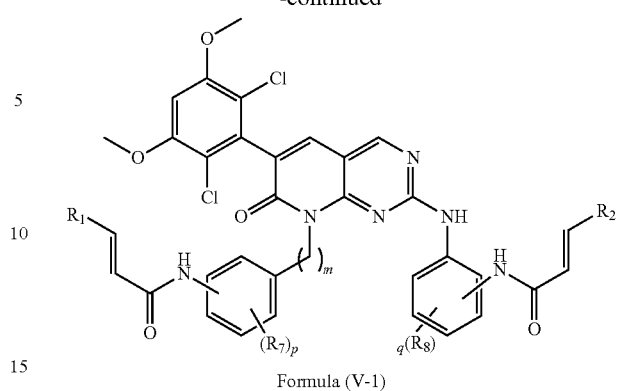

Formula (V-1)

In Scheme A, the commercially available starting material 2-(methylthio)pyrido[2,3-d]pyrimidin-7(8H)-one (A-1) can be selectively brominated to give A-2, which can then be alkylated to give intermediate A-3. A-3 undergoes Suzuki coupling to yield thioether A-4, which is subsequently oxidized to give sulfone intermediate A-5. Bis-chlorination followed by substitution reaction with Boc-protected benzene-1,2-diamine followed by a de-Boc process to give intermediate A-7. The nitro group in A-7 is reduced to give di-amino analogue A-8, which upon double acylation with acryl chloride gives final compounds of Formula (V-1).

As a further example, a typical approach to synthesize of Formular (V-1) compounds

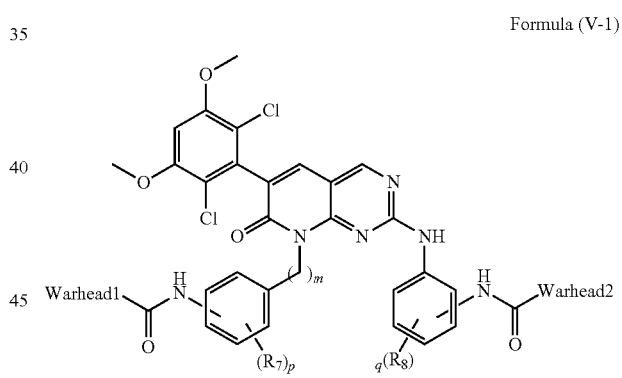

Formula (V-1)

is described in Scheme B. Warhead1, Warhead2, m, p, q, $R_7$, and $R_8$ in Scheme B are the same as those described in the Summary section above.

Scheme B

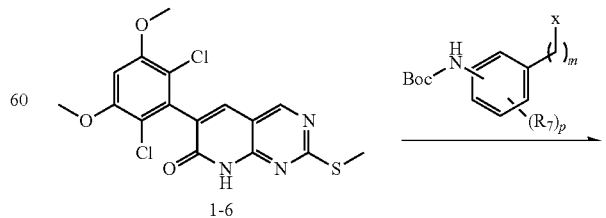

1-6

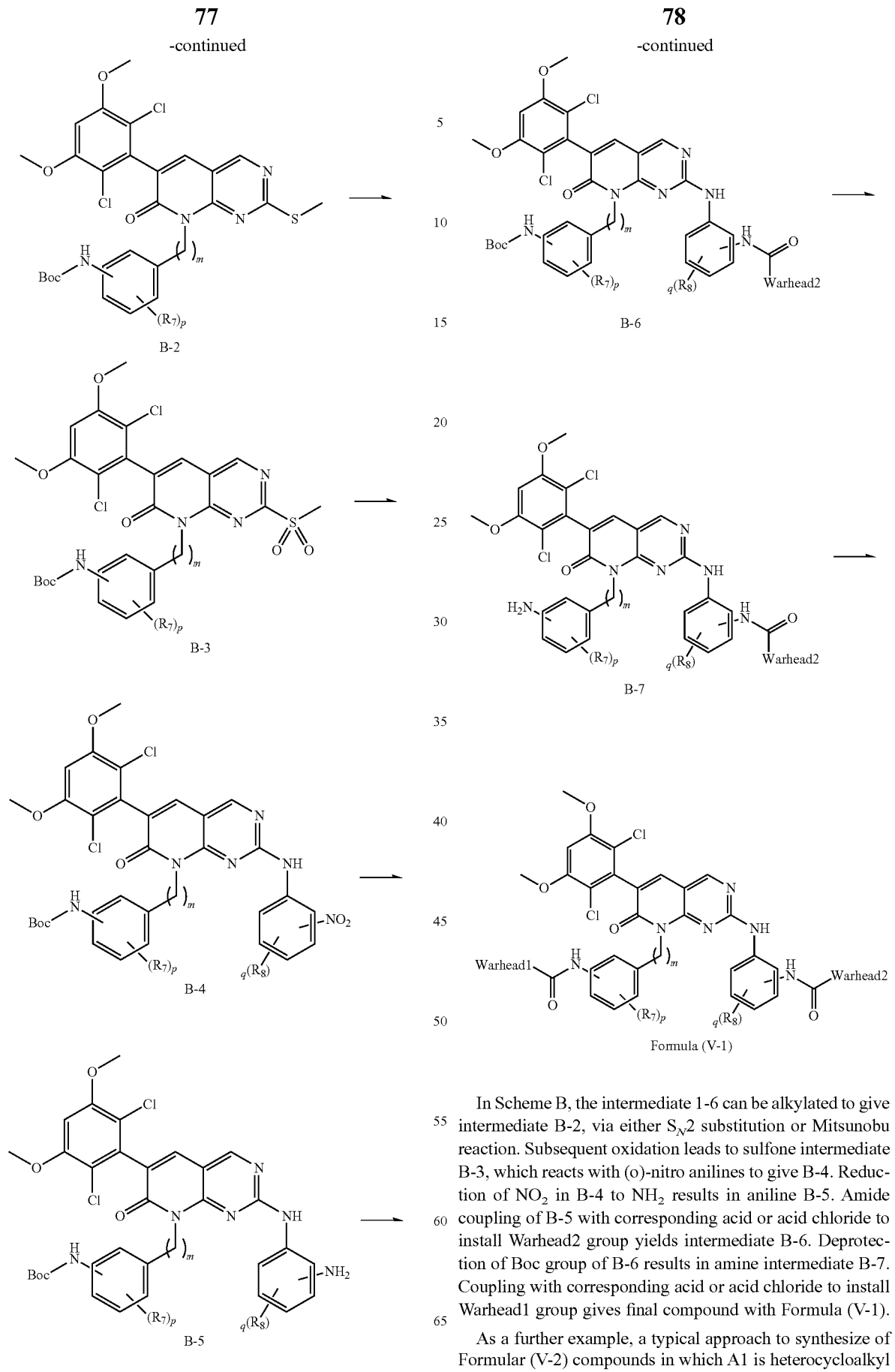

In Scheme B, the intermediate 1-6 can be alkylated to give intermediate B-2, via either $S_N2$ substitution or Mitsunobu reaction. Subsequent oxidation leads to sulfone intermediate B-3, which reacts with (o)-nitro anilines to give B-4. Reduction of $NO_2$ in B-4 to $NH_2$ results in aniline B-5. Amide coupling of B-5 with corresponding acid or acid chloride to install Warhead2 group yields intermediate B-6. Deprotection of Boc group of B-6 results in amine intermediate B-7. Coupling with corresponding acid or acid chloride to install Warhead1 group gives final compound with Formula (V-1).

As a further example, a typical approach to synthesize of Formular (V-2) compounds in which A1 is heterocycloalkyl Formula (V-2)
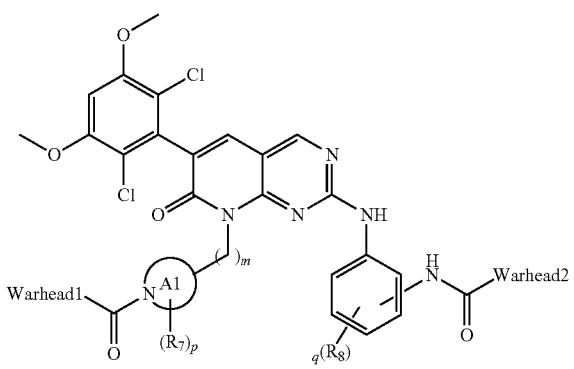
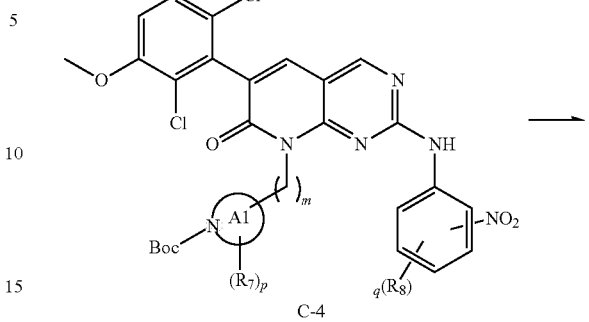
C-4
is described in Scheme C. Warhead1, Warhead2, m, p, q, R$_7$, and R$_8$ in Scheme C are the same as those described in the Summary section above.
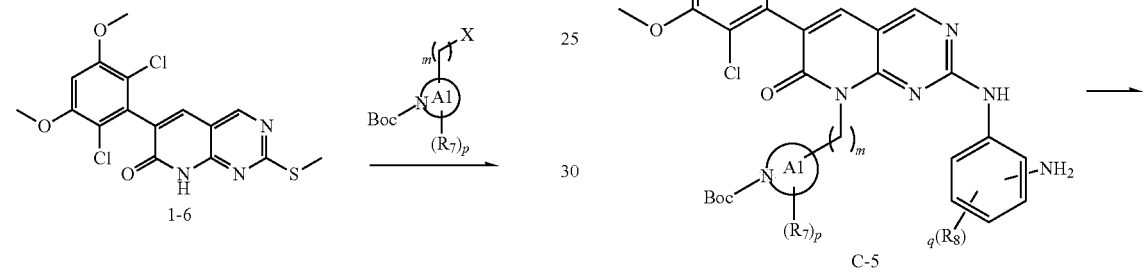
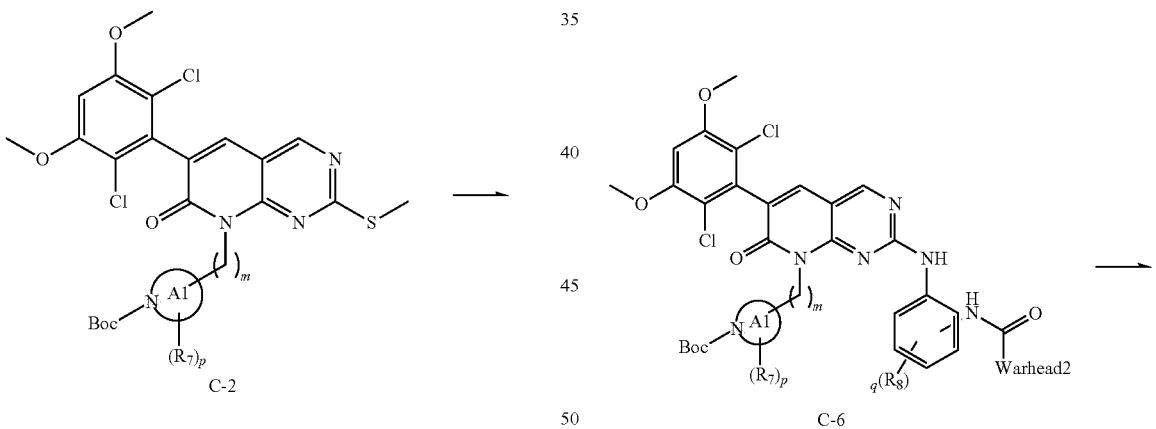
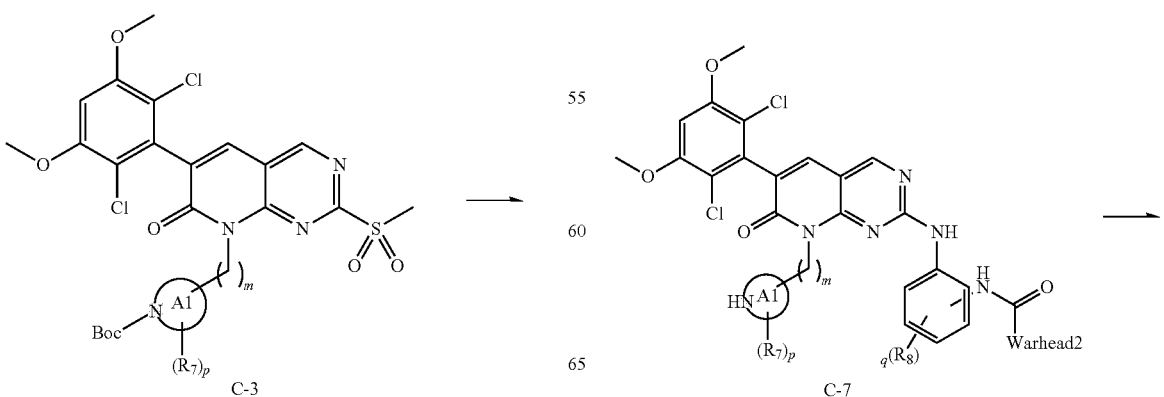

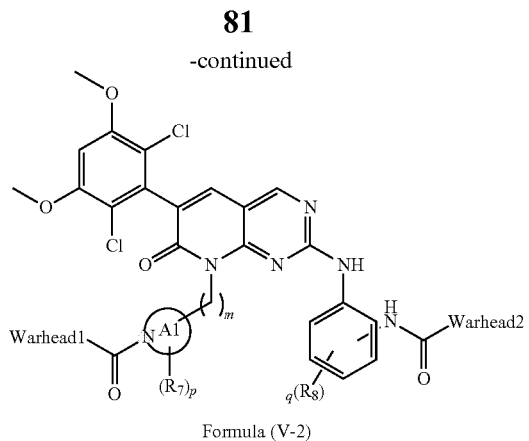

Formula (V-2)

In Scheme C, the intermediate 1-6 can be alkylated to give intermediate C-2, via either S$_N$2 substitution or Mitsunobu reaction. Subsequent oxidation leads to sulfone intermediate C-3, which reacts with (o)-nitro anilines to give C-4. Reduction of NO$_2$ in C-4 to NH$_2$ results in aniline C-5. Amide coupling of C-5 with corresponding acid or acid chloride to install Warhead2 group yields intermediate C-6. Deprotection of Boc group of C-6 results in amine intermediate C-7. Coupling with corresponding acid or acid chloride to install Warhead1 group gives final compound with Formula (V-2).

As a further example, a typical approach to synthesize of Formular (V-3) compounds in which B1 is cycloalkyl or heterocycloalkyl Formula (V-3)

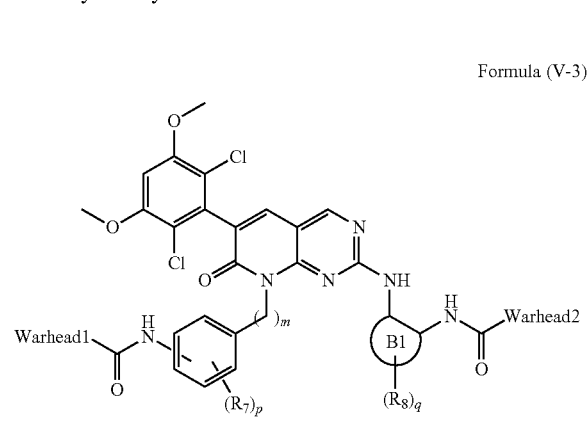

is described in Scheme D. Warhead1, Warhead2; m, p, q, R$_7$, and R$_8$ in Scheme D are the same as those described in the Summary section above.

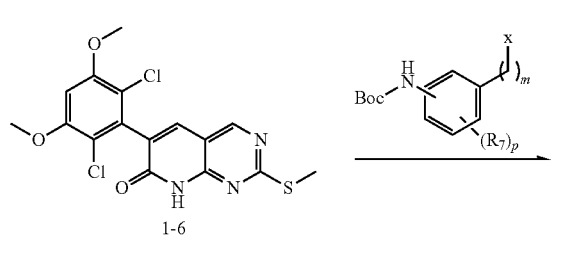

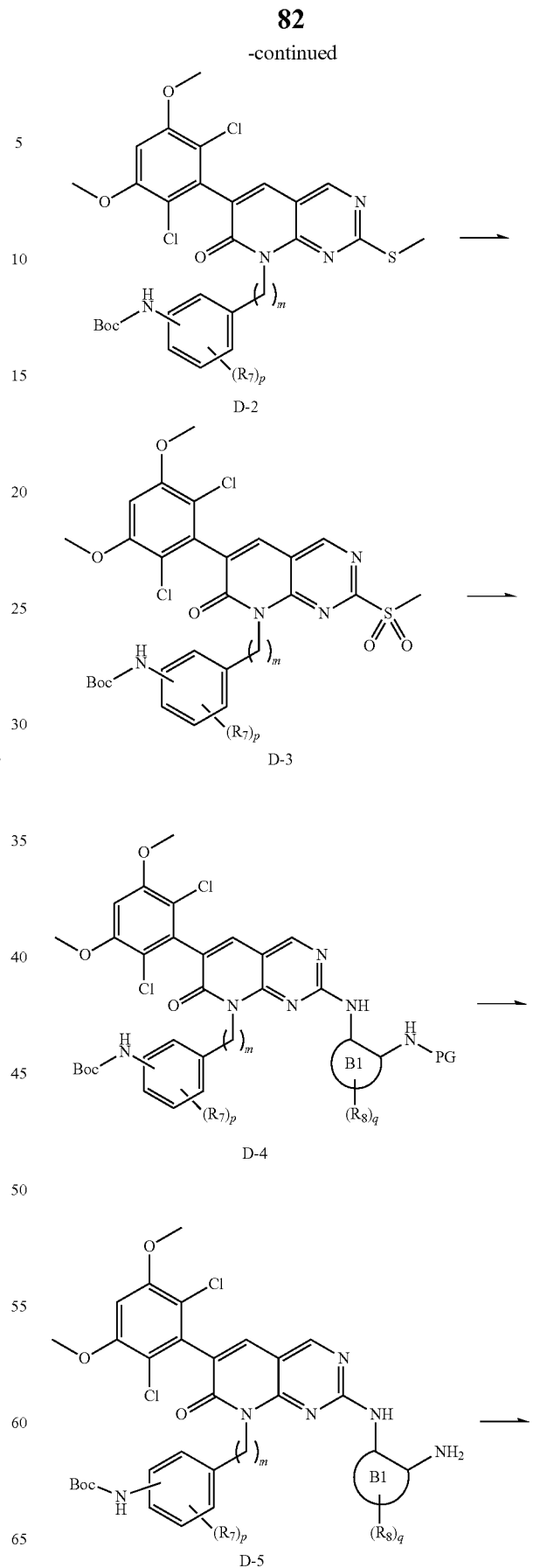

-continued

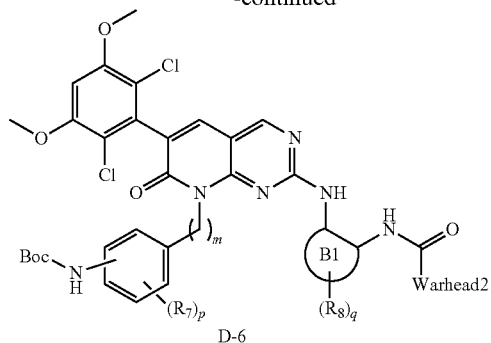
D-6

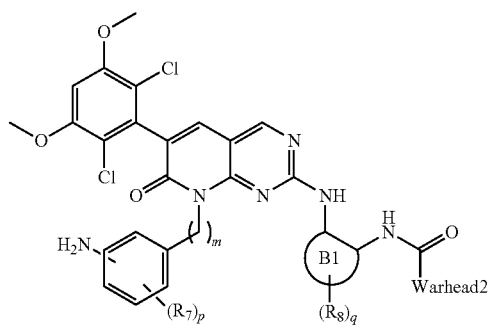
D-7

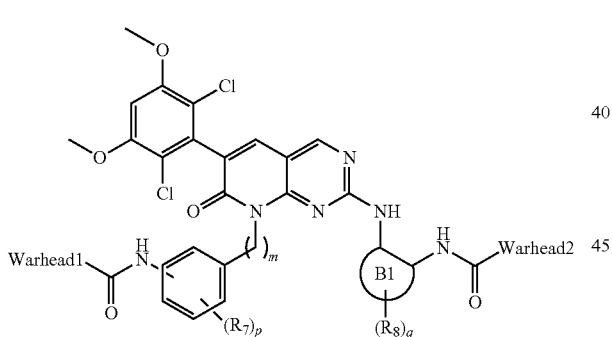
Formula (V-3)

In Scheme D, the intermediate 1-6 can be alkylated to give intermediate D-2, via either S$_N$2 substitution or Mitsunobu reaction. Subsequent oxidation leads to sulfone intermediate D-3, which reacts with appropriate amine to give D-4. Selective deprotection of D-4 results in amine D-5. Amide coupling of D-5 with corresponding acid or acid chloride to install Warhead2 group yields intermediate D-6. Deprotection of Boc group of D-6 results in amine intermediate D-7. Coupling with corresponding acid or acid chloride to install Warhead1 group gives final compound with Formula (V-3).

As a further example, a typical approach to synthesize of Formular (V-4) compounds in which A1 is heterocycloalkyl and B1 is cycloalkyl or heterocycloalkyl

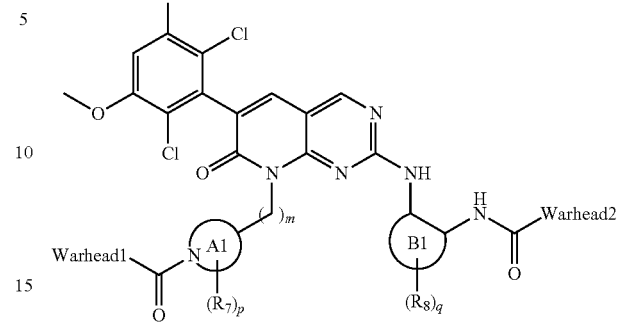
Formula (V-3)

is described in Scheme E. Warhead1, Warhead2, m, p, q, R$_7$, and R$_8$ in Scheme E are the same as those described in the Summary section above.

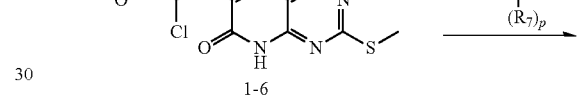
1-6

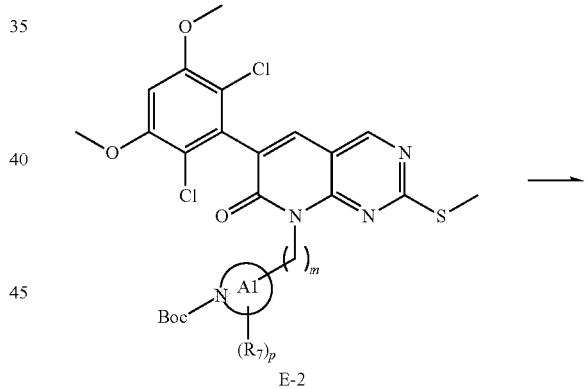
E-2

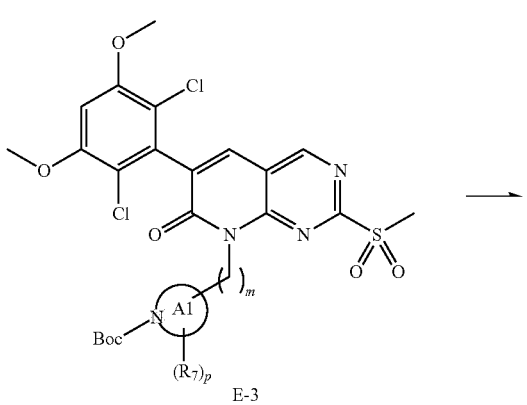
E-3

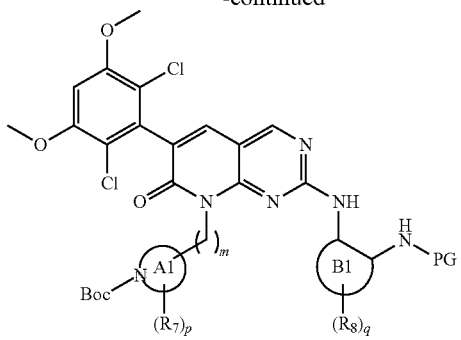

E-4

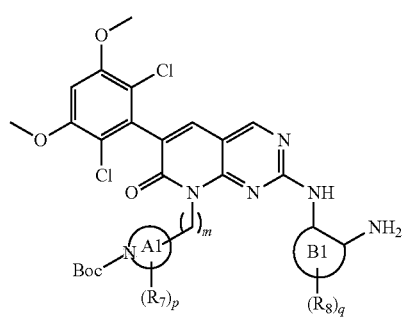

E-5

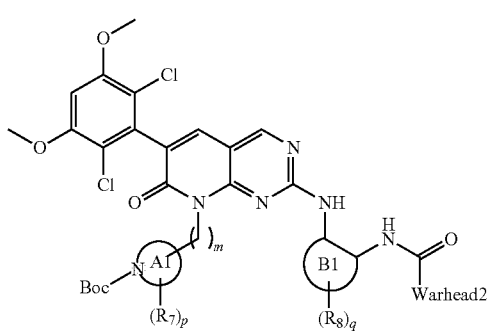

E-6

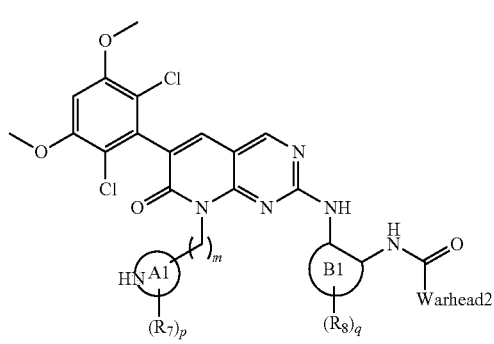

E-7

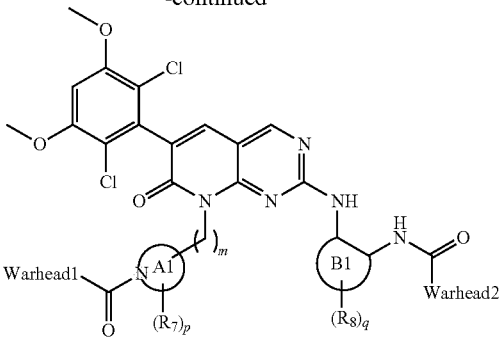

Formula (V-4)

In Scheme E, the intermediate 1-6 can be alkylated to give intermediate E-2, via either $S_N2$ substitution or Mitsunobu reaction. Subsequent oxidation leads to sulfone intermediate E-3, which reacts with appropriate amine to give E-4. Selective deprotection of E-4 results in amine intermediate E-5. Amide coupling of E-5 with corresponding acid or acid chloride to install Warhead2 group yields intermediate E-6. Deprotection of Boc group of E-6 results in amine intermediate E-7. Coupling with corresponding acid or acid chloride to install Warhead1 group gives final compound with Formula (V-4).

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example 1: Preparation of Intermediate 6

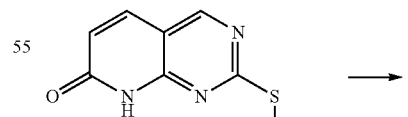

1

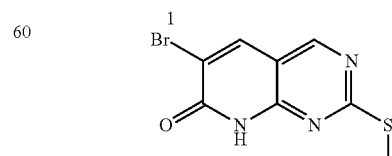

2

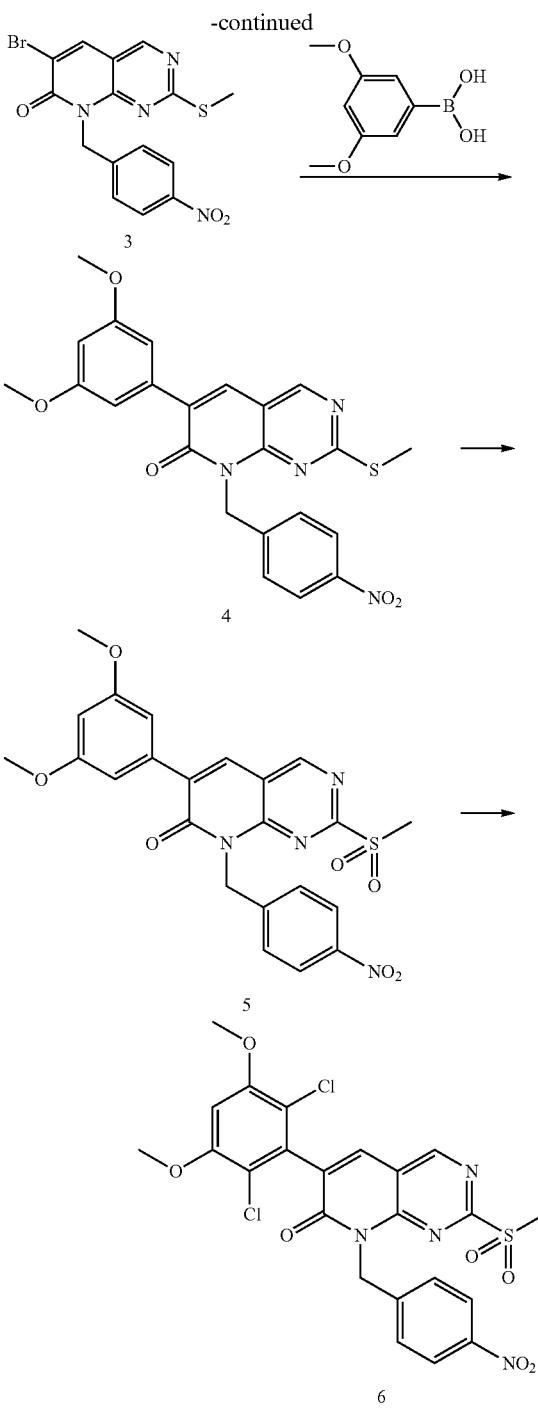

ESMS m/z 272 (M+H)+; $^1$H NMR (400 MHz, DMSO-$d_6$) δ ppm 12.88 (br. s., 1H), 8.84 (s, 1H), 8.47 (s, 1H), 2.57 (s, 3H).

Step 2: Synthesis of 6-bromo-2-(methylthio)-8-(4-nitrobenzyl)pyrido[2,3-d]pyrimidin-7(8H)-one (intermediate 3)

To the solution of NaH (2.2 mmol, 1.5 equiv.) in DMF (5 mL) was at rt added intermediate (1.5 mmol) and the mixture heated to 50° C. for 30 minutes. Cooled to rt, added p-nitrobenzyl bromide (1.8 mmol, 1.2 equiv.) as a solution in DMF (1 mL). Heated to 50° C. for 3 hours. Cooled, diluted with water, extracted 3× with. Organic portions combined and washed with brine and dried over MgSO$_4$, filtered and stripped. Used without further purification. m/z (MH+)=407.

Step 3: Synthesis of 6-(3,5-dimethoxyphenyl)-2-(methylthio)-8-(4-nitrobenzyl)pyrido[2,3-d]pyrimidin-7(8H)-one (intermediate 4)

Intermediate 3 (0.50 mmol), (3,5-dimethoxyphenyl)boronic acid (1.50 mmol), K$_3$PO$_4$ (1.50 mmol) and Pd(PPh$_3$)$_4$(0.02 mmol) were mixed as solids and placed under argon. Argon was bubbled through the mixture of dimethoxyethane:ethanol:water (1:1:1, 2.0 mL) for 20 min. The solvent was added to the solid and the suspension was heated under microwave irradiation at 120° C. for 1 h. After completion, the reaction mixture evaporated to dryness, the crude product was purified by silica gel column chromatography using dichloromethane:ethyl acetate (100:0.5) to yield intermediate 4, yield 80%. m/z (MH+)=407.

Step 4: Synthesis of 6-(3,5-dimethoxyphenyl)-2-(methylsulfonyl)-8-(4-nitrobenzyl)pyrido[2,3-d]pyrimidin-7(8H)-one (intermediate 5)

3-Chloroperbenzoic acid (3.27 mmol) was added to a solution of intermediate 4 (0.98 mmol) in dichloromethane (5.0 mL) at room temperature. After 30 minutes, the reaction was diluted with dichloromethane (50 mL) and washed twice with saturated NaHCO$_3$, followed by brine. The organic phase was separated and dried over Na$_2$SO$_4$, filtered and concentrated in vacuo. The residue was precipitated with ethyl acetate to provide intermediate 5 (71% yield), m/z (MH+)=497.

Step 5: Synthesis of 6-(2,6-dichloro-3,5-dimethoxyphenyl)-2-(methylsulfonyl)-8-(4-nitrobenzyl)pyrido[2,3-d]pyrimidin-7(8H)-one (intermediate 6)

To a solution of intermediate 5 (2.5 mmol) in acetonitrile (50 mL) was slowly added a solution of sulfuryl chloride (10.0 mmol) in acetonitrile (25 mL) over a period of 0.5 hour at a temperature ranging from −10° C. to 0° C. The reaction was monitored by thin layer chromatography (TLC). The reaction mixture was quenched by adding H$_2$O (10 mL). The resultant reaction solution was concentrated under reduced pressure, and the residue was recrystallizated with EtO Ac/petroleum ether=1:2 to give intermediate 6 (56% yield), $^1$H NMR (400 MHz, CDCl$_3$) δ 9.02 (s, 1H), 8.17 (d, J=8.6 Hz, 2H), 7.83 (d, J=8.6 Hz, 2H), 7.75 (s, 1H), 6.68 (s, 1H), 5.81 (s, 2H), 3.98 (s, 6H), 3.38 (s, 3H). m/z (MH+)=565.

Step 1: Synthesis of 6-bromo-2-(methylthio)pyrido[2,3-d]pyrimidin-7(8H)-one (intermediate 2)

To a solution of 2-(methylthio)pyrido[2,3-d]pyrimidin-7 (8H)-one (1, 1.00 g, 5.18 mmol) in anhydrous dimethylformamide (25 mL) was added N-bromosuccinimide (0.99 g, 5.59 mmol) portionwise at room temperature, and the reaction mixture was stirred for 18 h. The mixture was concentrated, and the solid was triturated with hot water (1×20 mL), filtered, and washed with isopropanol to give title compound. Yield 0.68 g, 2.50 mmol (48%), pale yellow solid.

Example 2: Preparation of CY-15-1

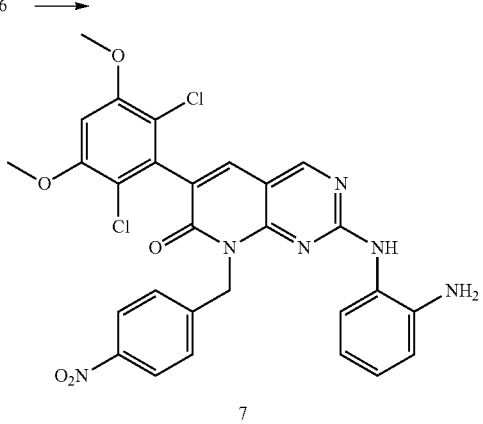

Step 1: Synthesis of 2-((2-aminophenyl)amino)-6-(2,6-dichloro-3,5-dimethoxyphenyl)-8-(4-nitrobenzyl)pyrido[2,3-d]pyrimidin-7(8H)-one (intermediate 7)

To a mixture of intermediate 6 (2.3 mmol) and benzene-1,2-diamine (4.5 mmol) in DMF (20 mL), potassium tert-butoxide (6.75 mmol) was added at −10° C., and the reaction mixture was stirred at room temperature for 5 minutes. The reaction mixture was diluted with EtOAc (150 mL), and the organic phase was separated, washed with water (2×150 mL) and then brine (150 mL), dried over sodium sulfate, filtered, and concentrated. The residue was recrystallizated with EtOAc to give intermediate 7 (yield 62%), m/z (MH$^+$)=593.

Step 2: Synthesis of 8-(4-aminobenzyl)-2-((2-aminophenyl)amino)-6-(2,6-dichloro-3,5-dimethoxyphenyl)pyrido[2,3-d]pyrimidin-7(8H)-one (intermediate 8)

A mixture of intermediate 7 (1.6 mmol) and tin(II) chloride hydrate (7.9 mmol) in EtOAc (50 mL) was stirred at 60° C. for 2 hours. The reaction was monitored by LCMS. The reaction mixture was basified with saturated aqueous sodium bicarbonate to pH=8-9, diluted with H2O (100 mL), and then extracted with EtOAc (3×100 mL). The combined organic layers were washed with brine (150 mL), dried over sodium sulfate, filtered, and concentrated. The residue was recrystallized with dichloromethane/ethyl acetate/petroleum ether (DCM/EtOAc/PE)=1/1/2 to give intermediate 8 (63% yield), m/z (MH$^+$)=563.

Step 3: Synthesis of N-(2-((8-(4-acrylamidobenzyl)-6-(2,6-dichloro-3,5-dimethoxyphenyl)-7-oxo-7,8-dihydropyrido[2,3-d]pyrimidin-2-yl)amino)phenyl)acrylamide (CY-20141215)

Intermediate 8 was taken up in DCM (2 ml) and cooled to 0° C., followed by addition of acryloyl chloride (0.25 mmol). The reaction was allowed to warm to room temperature and stirred overnight. The mixture was loaded directly onto silica gel and purified by flash chromatography using 0-100% EtOAc/Hexanes gradient to provide the product CY-15-1, m/z (MH$^+$)=671. $^1$H NMR (400 MHz, DMSO) δ 10.08 (s, 1H), 9.82 (s, 1H), 9.32 (s, 1H), 8.80 (s, 1H), 7.82 (d, J=5.6 Hz, 1H), 7.73 (d, J=7.5 Hz, 1H), 7.61 (d, J=7.7 Hz, 1H), 7.46 (d, J=8.4 Hz, 2H), 7.30-7.19 (m, 2H), 7.04 (d, J=23.0 Hz, 3H), 6.53 (dd, J=16.9, 10.3 Hz, 1H), 6.40 (dd, J=17.0, 10.1 Hz, 1H), 6.33-6.19 (m, 2H), 5.81-5.69 (m, 2H), 5.29 (s, 2H), 3.97 (s, 6H).

Example 3: Preparation of CY-15-2

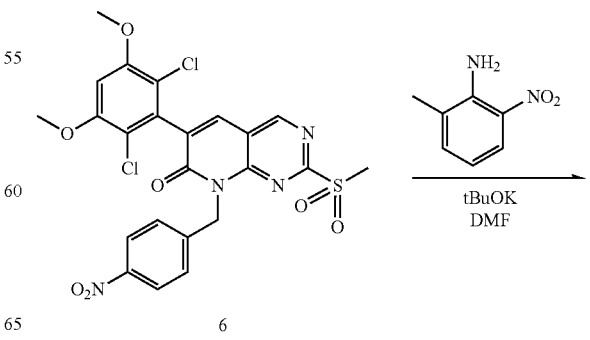

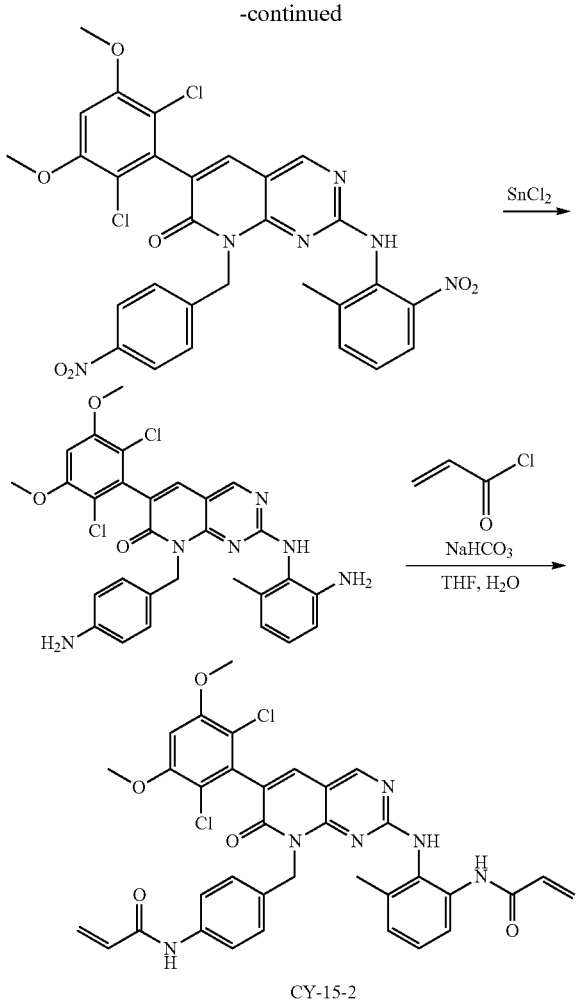

CY-15-2

Synthesis of 6-(2,6-dichloro-3,5-dimethoxyphenyl)-2-((2-methyl-6-nitrophenyl)amino)-8-(4-nitrobenzyl)pyrido[2,3-d]pyrimidin-7(8H)-one To a 30 mL flask were added 6-(2,6-dichloro-3,5-dimethoxyphenyl)-2-(methylsulfonyl)-8-(4-nitrobenzyl)pyrido[2,3-d]pyrimidin-7(8H)-one (300 mg, 0.532 mmol), 2-methyl-6-nitroaniline (160 mg, 1.05 mmol), DMF (8.0 mL) and potassium tert-butyloxide (170 mg, 1.52 mmol) in sequence. The reaction mixture was stirred at rt for 10 min then added with water (50 mL). The mixture was extracted with EtOAc (3×20 mL) and organic phase was concentrated. The residue was purified by flash column chromatrography (hexanes/EtOAc, 1:1 to 1:10, v/v) to give the title compound (112 mg, 33%) as yellow solid. MS (ESI): mass calcd. for $C_{29}H_{22}Cl_2N_6O_5$ 636.09, m/z found 636.8 [M+H]$^+$.

Synthesis of 2-((2-amino-6-methylphenyl)amino)-8-(4-aminobenzyl)-6-(2,6-dichloro-3,5-dimethoxyphenyl)pyrido[2,3-d]pyrimidin-7(8H)-one To a 100 mL round-bottomed flask were added 6-(2,6-dichloro-3,5-dimethoxyphenyl)-2-((2-methyl-6-nitrophenyl)amino)-8-(4-nitrobenzyl)pyrido[2,3-d]pyrimidin-7(8H)-one (112 mg, 0.176 mmol), EtOAc (5 mL) and SnCl$_2$.2H$_2$O (177 mg, 0.786 mmol). The mixture was heated at 60° C. for 4 h then cooled to rt. The mixture was added with saturated sodium bicarbonate solution (10 mL) then extracted with EtOAc (3×20 mL). The combined organic phase was concentrated to dryness and the residue was purified by flash column chromatrography (CH$_2$Cl$_2$/MeOH, 20:1, v/v) to give the title compound (71 mg, 70%) as yellow solid. MS (ESI): mass calcd. for $C_{29}H_{26}Cl_2N_6O_3$ 576.14, m/z found 576.8 [M+H]$^+$.

Synthesis of N-(4-((2-((2-acrylamido-6-methylphenyl)amino)-6-(2,6-dichloro-3,5-dimethoxyphenyl)-7-oxopyrido[2,3-d]pyrimidin-8(7H)-yl)methyl)phenyl)acrylamide (CY-15-2)

To a 100 mL round-bottomed flask were added 2-((2-amino-6-methylphenyl)amino)-8-(4-aminobenzyl)-6-(2,6-dichloro-3,5-dimethoxyphenyl)pyrido[2,3-d]pyrimidin-7(8H)-one (71 mg, 0.12 mmol), sodium bicarbonate (42 mg, 0.50 mmol), THF (6 mL) and water (1.5 mL). The mixture was stirred at rt for 5 min then added with acryloyl chloride (28 mg, 0.32 mmol). After stirred for another 30 min, the mixture was extracted with ethyl acetate (3×15 mL). The combined organic phase was concentrated to dryness. The residue was purified by flash column chromatrography (hexanes/EtOAc, 1:1 to pure EtOAc, v/v) following by trituration with n-hexane and ethyl acetate to give the title compound (26 mg, 31%) as light yellow solid. MS (ESI): mass calcd. for $C_{35}H_{30}Cl_2N_6O_5$ 684.17, m/z found 684.8 [M+H]$^+$. $^1$H NMR (400 MHz, DMSO) δ 10.07 (s, 1H), 9.46 (s, 1H), 9.13 (s, 1H), 8.77 (s, 1H), 7.86 (s, 1H), 7.77 (s, 1H), 7.47 (d, J=8.2 Hz, 1H), 7.34 (s, 2H), 7.23 (s, 1H), 7.02 (d, J=11.9 Hz, 1H), 6.76 (s, 2H), 6.53 (dd, J=17.2, 10.6 Hz, 1H), 6.486.35 (m, 1H), 6.24 (d, J=16.9 Hz, 2H), 5.78-5.62 (m, 2H), 5.02 (s, 2H), 3.97 (s, 6H), 2.13 (s, 3H).

Example 4: Preparation of IM-15-4

-continued

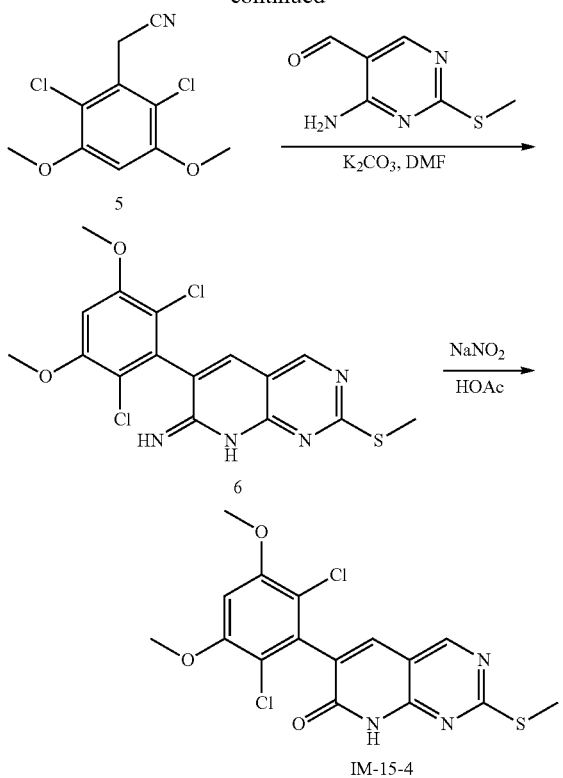

IM-15-4

Synthesis of 1,3-dimethoxy-5-methylbenzene

A stirring mixture of 1 (500.0 g, 4.02 mol), anhydrous K$_2$CO$_3$ (2783.0 g, 20.1 mol), and methyl iodide (2858.0 g, 20.1 mol) in acetonitrile (5 L) was refluxed overnight. After cooling, the reaction mixture was filtered through Celite. The solvent was removed by evaporation to get the product 2 (523.0 g, crude) as a yellow oil, which was used in the next step directly. LCMS: 153.2 (M+1)$^+$, t$_R$=2.6 min. HPLC: 88%, t$_R$=5.3 min. $^1$HNMR (400 MHz, CDCl$_3$) δ 6.33 (d, J=2.1 Hz, 2H), 6.28 (t, J=2.1 Hz, 1H), 3.77 (d, J=3.5 Hz, 6H), 2.30 (s, 3H).

Synthesis of 2,4-dichloro-1,5-dimethoxy-3-methylbenzene

Into a 3-necked round-bottom flask, which was purged and maintained with an inert atmosphere of nitrogen, was placed a solution of 1,3-dimethoxy-5-methylbenzene (523.0 g, crude) in dichloromethane (6 L). This was followed by the addition of sulfuroyl dichloride (927.7 g, 6.86 mol) dropwise with stirring at 0° C. The resulting solution was stirred overnight at room temperature. The pH value of the solution was adjusted to 8 with sodium carbonate (sat. aq.). The resulting solution was extracted with dichloromethane, and the combined organic layers were concentrated under vacuum. The resulting mixture was washed with hexane to give the product 3 (421.0 g, 47% for 2 steps) as a white solid. LCMS: 221.1 (M+1)$^+$, t$_R$=2.7 min. HPLC: 98%, t$_R$=7.1 min. $^1$HNMR (400 MHz, CDCl$_3$) δ 6.45 (s, 1H), 3.90 (s, 6H), 2.48 (s, 3H).

Synthesis of 3-(bromomethyl)-2,4-dichloro-1,5-dimethoxybenzene

Into a round-bottom flask, was placed a solution of 2,4-dichloro-1,5-dimethoxy-3-methylbenzene (418.0 g, 1.89 mol) in tetrachloromethane (5 L). NBS (353.3 g, 1.99 mol) and AIBN (40.4 g, 0.25 mol) were added to the reaction mixture. The resulting solution was heated to reflux overnight. The reaction was then quenched by the addition of sodium carbonate (sat. aq.). The organic layer was washed with sodium chloride (sat.). The resulting mixture was concentrated under vacuum to give the product 4 (378.0 g, 66%) as a yellow solid. $^1$HNMR (400 MHz, CDCl$_3$) δ 6.55 (s, 1H), 4.79 (s, 2H), 3.92 (s, 6H).

Synthesis of 2-(2,6-dichloro-3,5-dimethoxyphenyl)acetonitrile

To a solution of 4 (378 g, 1.26 mol) in THF (5 L), TBAF (659.2 g, 2.52 mol) and TMSCN (250 g, 2.52 mol) was added at 0° C. The reaction mixture was stirred at room temperature for 1 h. TLC analysis showed the reaction was completed. The solvent was evaporated in vacuo. The resulting mixture was washed with dichloromethane to give the product 5 (283 g, 91%) as a white solid. LCMS: 246.1 (M+1)$^+$, t$_R$=5.1 min. HPLC: 97%, t$_R$=5.1 min. $^1$HNMR (400 MHz, CDCl$_3$) δ 6.58 (s, 1H), 4.03 (s, 2H), 3.93 (s, 6H).

Synthesis of 6-(2,6-dichloro-3,5-dimethoxyphenyl)-2-(methylthio)pyrido[2,3-d]pyrimidin-7(8H)-imine Into a 100-mL round-bottom flask, was placed a solution of 4-amino-2-(methylsulfanyl)-pyrimidine-5-carbaldehyde (174.9 g, 1.03 mol) in DMF (1.5 L). 2-(2,6-Dichloro-3,5-dimethoxyphenyl) acetonitrile (253 g, 1.03 mol), and potassium carbonate (235.5 g, 3.09 mol) were added and the resulting solution was stirred overnight at 100° C. in an oil bath. The solvent was removed by evaporation to get the product 6 (302 g, crude), which was used in the next step directly. LCMS: 397.1 (M+1)$^+$, t$_R$=2.3 min. HPLC: 70%, t$_R$=4.5 min. $^1$HNMR (400 MHz, DMSO) δ 8.88 (s, 1H), 7.81 (s, 1H), 7.04 (s, 1H), 3.98 (s, 6H), 2.56 (s, 3H).

Synthesis of 6-(2,6-dichloro-3,5-dimethoxyphenyl)-2-(methylthio)pyrido[2,3-d]pyrimidin-7(8H)-one Into a 50-mL round-bottom flask, was placed a solution of 6-(2,6-dichloro-3,5-dimethoxyphenyl)-2-(methylthio) pyrido[2,3-d]pyrimidin-7(8H)-imine (151 g, crude) in acetic acid (8 L). NaNO$_2$ (131 g, 1.9 mol) was added the reaction mixture. The resulting solution was stirred for overnight at 70° C., and then it was quenched with water. The solids were collected by filtration and wash with dichloromethane to give 6-(2,6-dichloro-3,5-dimethoxyphenyl)-2-(methylthio) pyrido[2,3-d]pyrimidin-7(8H)-one IM-15-4 (75 g 36% for 2 steps) as a yellow solid. LCMS: 398.1 (M+1)$^+$, t$_R$=2.6 min. HPLC: 95%, t$_R$=5.0 min $^1$HNMR (400 MHz, DMSO) δ 12.74 (s, 1H), 8.92 (s, 1H), 7.92 (s, 1H), 7.02 (s, 1H), 3.98 (s, 6H), 2.60 (s, 3H).

Example 5: Preparation of CY-15-3
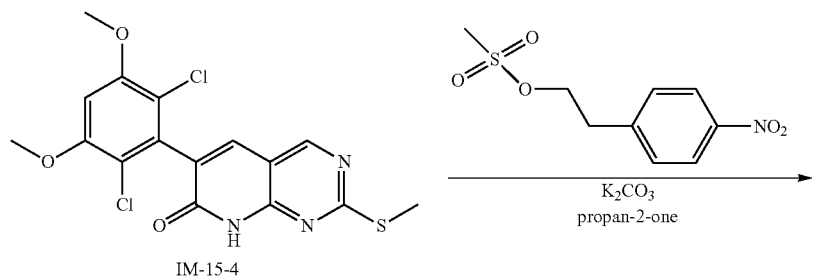
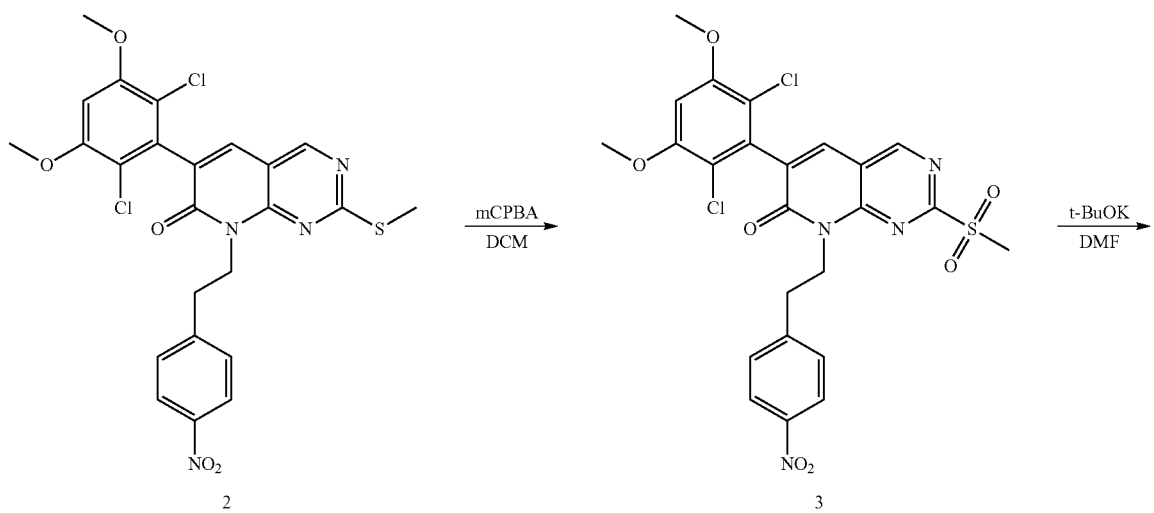
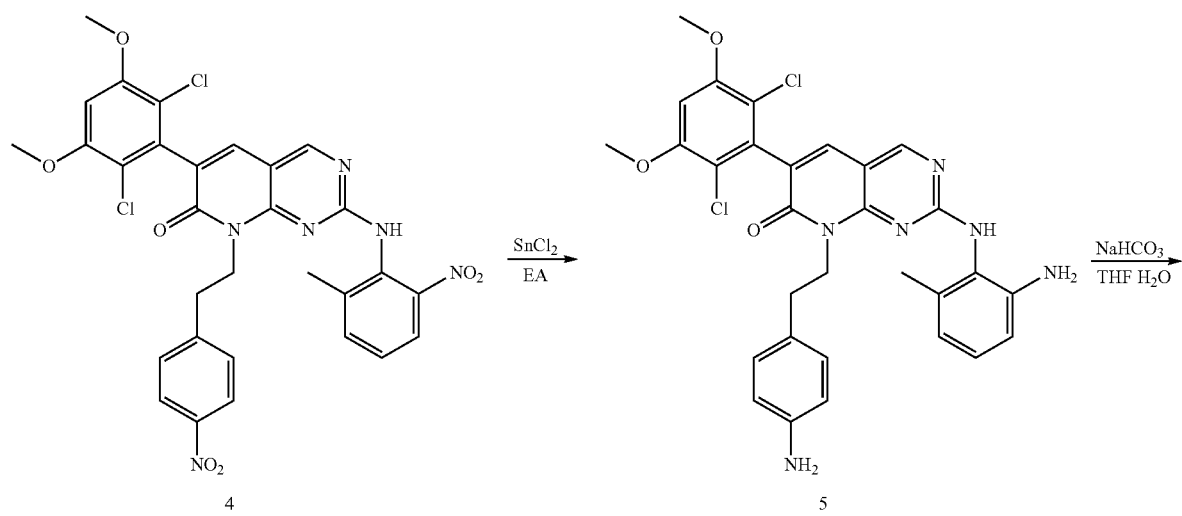

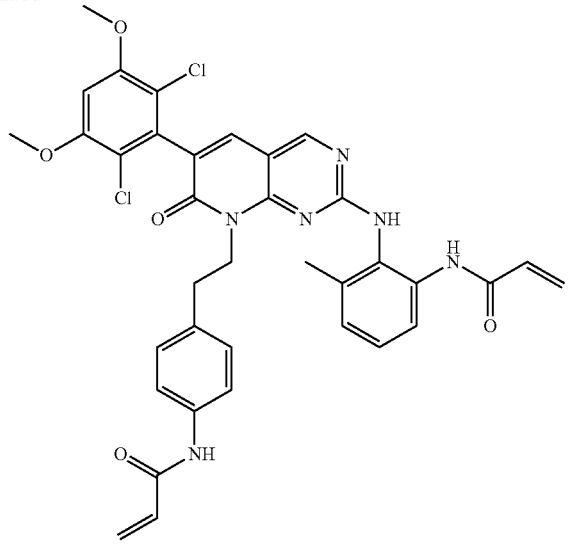

CY-15-3

Synthesis of 6-(2,6-dichloro-3,5-dimethoxyphenyl)-2-(methylthio)-8-(4-nitrophenethyl)pyrido[2,3-d]pyrimidin-7(8H)-one (2)

To a 100 mL sealed tube were added 6-(2,6-dichloro-3,5-dimethoxyphenyl)-2-(methylthio)pyrido[2,3-d]pyrimidin-7(8H)-one (800 mg, 2.0 mmol), acetone (25 mL) and 4-nitrophenethyl methanesulfonate (735 mg, 3.0 mmol). The mixture was heated at 80° C. for 14 h then cooled to rt. The mixture was added with water (100 mL) then filtered and the residue was washed with EtOAc (3×50 mL) and water (3×50 mL). The residue was concentrated to dryness to give the title compound (220 mg, 20%) as yellow solid. MS (ESI): mass calcd. for $C_{24}H_{20}Cl_2N_4O_5S$ 546.05, m/z found 547.1 [M+H]$^+$.

Synthesis of 6-(2,6-dichloro-3,5-dimethoxyphenyl)-2-(methylsulfonyl)-8-(4-nitrophenethyl)pyrido[2,3-d]pyrimidin-7(8H)-one (3)

To a 100 mL round-bottomed flask were added 6-(2,6-dichloro-3,5-dimethoxyphenyl)-2-(methylthio)-8-(4-nitrophenethyl)pyrido[2,3-d]pyrimidin-7(8H)-one (200 mg, 0.37 mmol) and m-CPBA (192 mg, 1.11 mmol) in DCM (20 mL). The mixture was stirred at rt for 50 min. The mixture was washed with NaHCO$_3$ aqueous solution (10 ml) and extracted with DCM (3×50 mL). The combined organic phase was concentrated to dryness. The residue was purified by flash column chromatrography (hexanes/EtOAc, 1:1 to pure EtOAc, v/v) following by trituration with n-hexane and ethyl acetate to give the title compound (150 mg, 71%) as light yellow solid. MS (ESI): mass calcd. for $C_{24}H_{20}Cl_2N_4O_7S$ 578.04, m/z found 578.8 [M+H]+.

6-(2,6-dichloro-3,5-dimethoxyphenyl)-2-(2-methyl-6-nitrophenylamino)-8-(4-nitrophenethyl)pyrido[2,3-d]pyrimidin-7(8H)-one (4)

To a 30 mL flask were added 6-(2,6-dichloro-3,5-dimethoxyphenyl)-2-(methylsulfonyl)-8-(4-nitrophenethyl)pyrido[2,3-d]pyrimidin-7(8H)-one (150 mg, 0.26 mmol), 2-methyl-6-nitroaniline (46 mg, 0.3 mmol), DMF (8.0 mL) and potassium tert-butyloxide (100 mg, 0.9 mmol) in sequence. The reaction mixture was stirred at rt for 10 min then added with water (50 mL). The mixture was extracted with EtOAc (3×20 mL) and organic phase was concentrated. The residue was purified by flash column chromatrography (hexanes/EtOAc, 1:1 to 1:10, v/v) to give the title compound (100 mg, 59%) as yellow solid. MS (ESI): mass calcd. for $C_{30}H_{24}Cl_2N_6O_7$ 650.11, m/z found 651.1 [M+H]$^+$.

Synthesis of 2-(2-amino-6-methylphenylamino)-8-(4-aminophenethyl)-6-(2,6-dichloro-3,5-dimethoxyphenyl)pyrido[2,3-d]pyrimidin-7(8H)-one (5)

To a 100 mL round-bottomed flask were added 6-(2,6-dichloro-3,5-dimethoxyphenyl)-2-(2-methyl-6-nitrophenylamino)-8-(4-nitrophenethyl)pyrido[2,3-d]pyrimidin-7(8H)-one (100 mg, 0.15 mmol), EtOAc (25 mL) and SnCl$_2$.2H$_2$O (290 mg, 1.5 mmol). The mixture was heated at 70° C. for 14 h then cooled to rt. The mixture was added with saturated sodium bicarbonate solution (10 mL) then extracted with EtOAc (3×20 mL). The combined organic phase was concentrated to dryness and the residue was purified by flash column chromatography (CH$_2$Cl$_2$/MeOH, 20:1, v/v) to give the title compound (50 mg, 56%) as yellow solid. MS (ESI): mass calcd. for $C_{30}H_{28}Cl_2N_6O_3$ 590.16, m/z found 591.2 [M+H]$^+$.

Synthesis of N-(4-(2-(2-(2-acrylamido-6-methylphenylamino)-6-(2,6-dichloro-3,5-dimethoxyphenyl)-7-oxopyrido[2,3-d]pyrimidin-8(7H)-yl)ethyl)phenyl)acrylamide (CY-15-3)

To a 100 mL round-bottomed flask were added 2-(2-amino-6-methylphenylamino)-8-(4-aminophenethyl)-6-(2,6-dichloro-3,5-dimethoxyphenyl)pyrido[2,3-d]pyrimidin-7(8H)-one (50 mg, 0.085 mmol), sodium bicarbonate (14 mg, 0.17 mmol), THF (6 mL) and water (1.5 mL). The mixture was stirred at rt for 5 min then added with acryloyl chloride (15 mg, 0.17 mmol). After stirred for another 30 min, the mixture was extracted with ethyl acetate (3×15 mL). The combined organic phase was concentrated to dryness. The residue was purified by flash column chromatography (hexanes/EtOAc, 1:1 to pure EtOAc, v/v) following by trituration with n-hexane and ethyl acetate to give the title compound (25 mg, 42%) as light yellow solid. MS (ESI): mass calcd. for $C_{36}H_{32}Cl_2N_6O_5$ 698.18, m/z found 698.5 [M+H]$^+$. $^1$H NMR (400 MHz, CD$_3$OD) δ 8.71 (s, 1H), 7.68 (s, 1H), 7.44 (s, 1H), 7.31 (s, 1H), 6.90 (s, 1H), 6.74 (s, 1H), 6.57-6.16 (m, 2H), 5.76 (ddd, J=25.7, 9.7, 2.0 Hz, 1H), 4.27 (s, 1H), 3.98 (s, 2H), 2.70 (s, 1H), 2.35 (s, 2H).

Example 6: Preparation of Additional Compounds

The following compounds were prepared according to the methods substantially identical, similar, or analogous to those used in examples 1-5.

| Example | Structure | m/z (MH$^+$) |
|---|---|---|
| 6-1 | 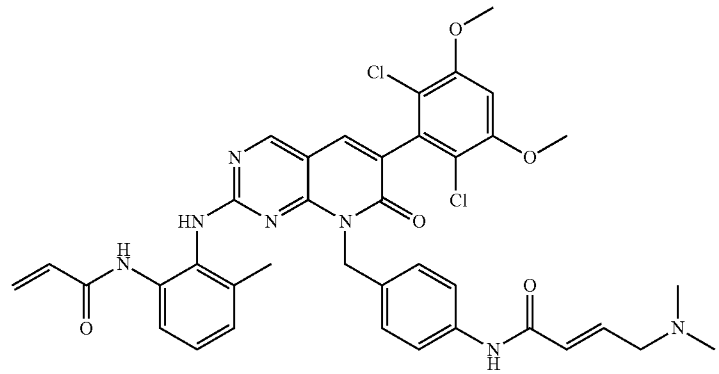 [SMILES: C=CC(=O)Nc1cccc(C)c1Nc1ncc2cc(-c3c(Cl)c(OC)cc(OC)c3Cl)c(=O)n(Cc3ccc(NC(=O)/C=C/CN(C)C)cc3)c2n1] | 742 |
| 6-2 | 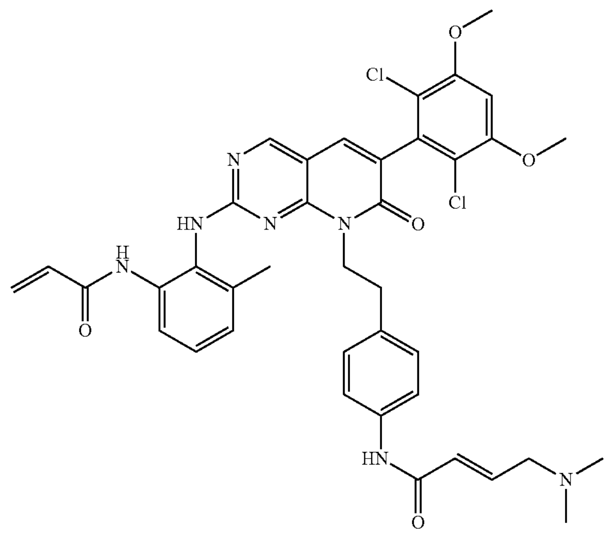 [SMILES: C=CC(=O)Nc1cccc(C)c1Nc1ncc2cc(-c3c(Cl)c(OC)cc(OC)c3Cl)c(=O)n(CCc3ccc(NC(=O)/C=C/CN(C)C)cc3)c2n1] | 756 |

The following compounds are prepared according to the methods substantially identical, similar, or analogous to those used in examples 1-5.

| Example | Structure | m/z (MH$^+$) |
|---|---|---|
| 6-3 | 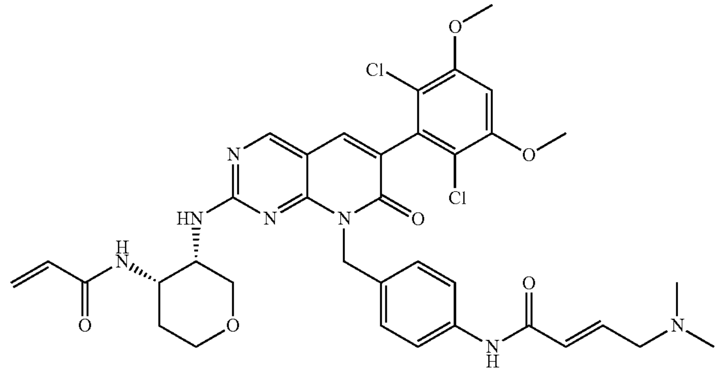 [SMILES: C=CC(=O)N[C@H]1CCOC[C@H]1Nc1ncc2cc(-c3c(Cl)c(OC)cc(OC)c3Cl)c(=O)n(Cc3ccc(NC(=O)/C=C/CN(C)C)cc3)c2n1] | 736 |

| 6-4 | 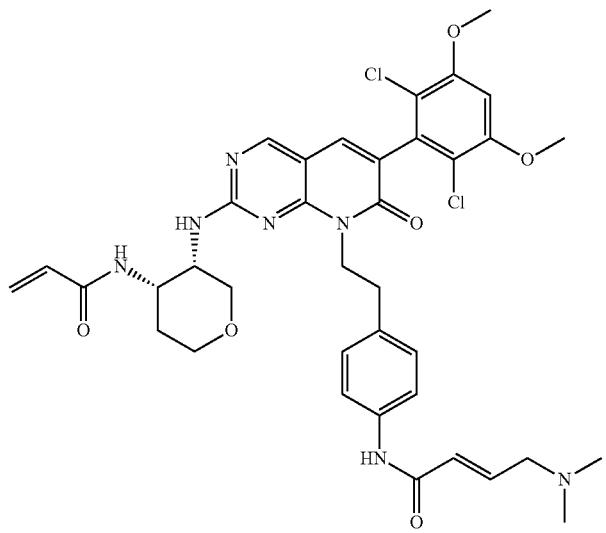 [SMILES: C=CC(=O)N[C@H]1CCOC[C@H]1Nc1ncc2cc(-c3c(Cl)c(OC)cc(OC)c3Cl)c(=O)n(CCc3ccc(NC(=O)/C=C/CN(C)C)cc3)c2n1] | 756 |
|---|---|---|
| 6-5 | 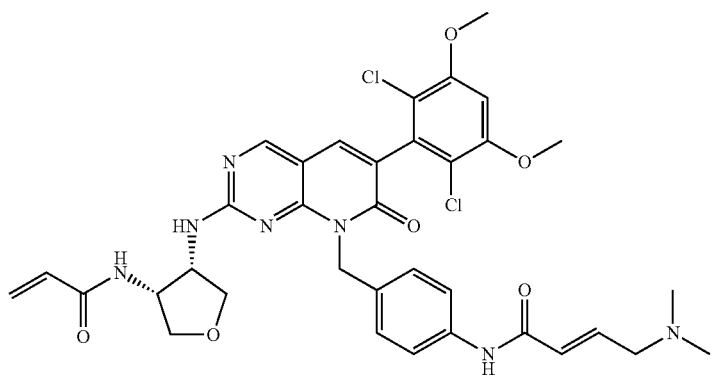 [SMILES: C=CC(=O)N[C@H]1COC[C@H]1Nc1ncc2cc(-c3c(Cl)c(OC)cc(OC)c3Cl)c(=O)n(Cc3ccc(NC(=O)/C=C/CN(C)C)cc3)c2n1] | 722 |
|---|---|---|
| 6-5 | 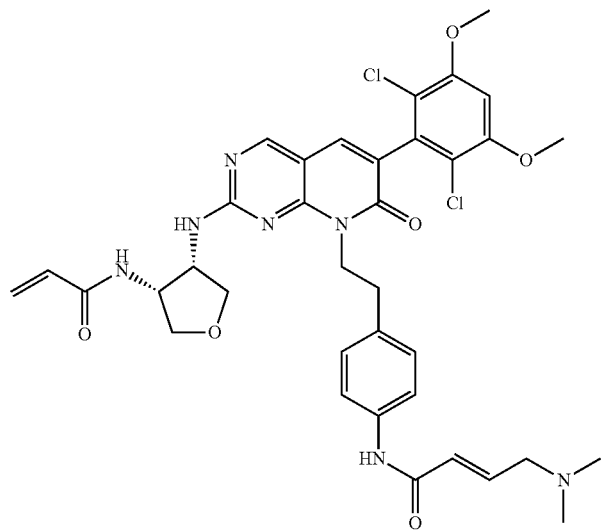 [SMILES: C=CC(=O)N[C@H]1COC[C@H]1Nc1ncc2cc(-c3c(Cl)c(OC)cc(OC)c3Cl)c(=O)n(CCc3ccc(NC(=O)/C=C/CN(C)C)cc3)c2n1] | 736 |
|---|---|---|

Example 7: Preparation of CY-15-4
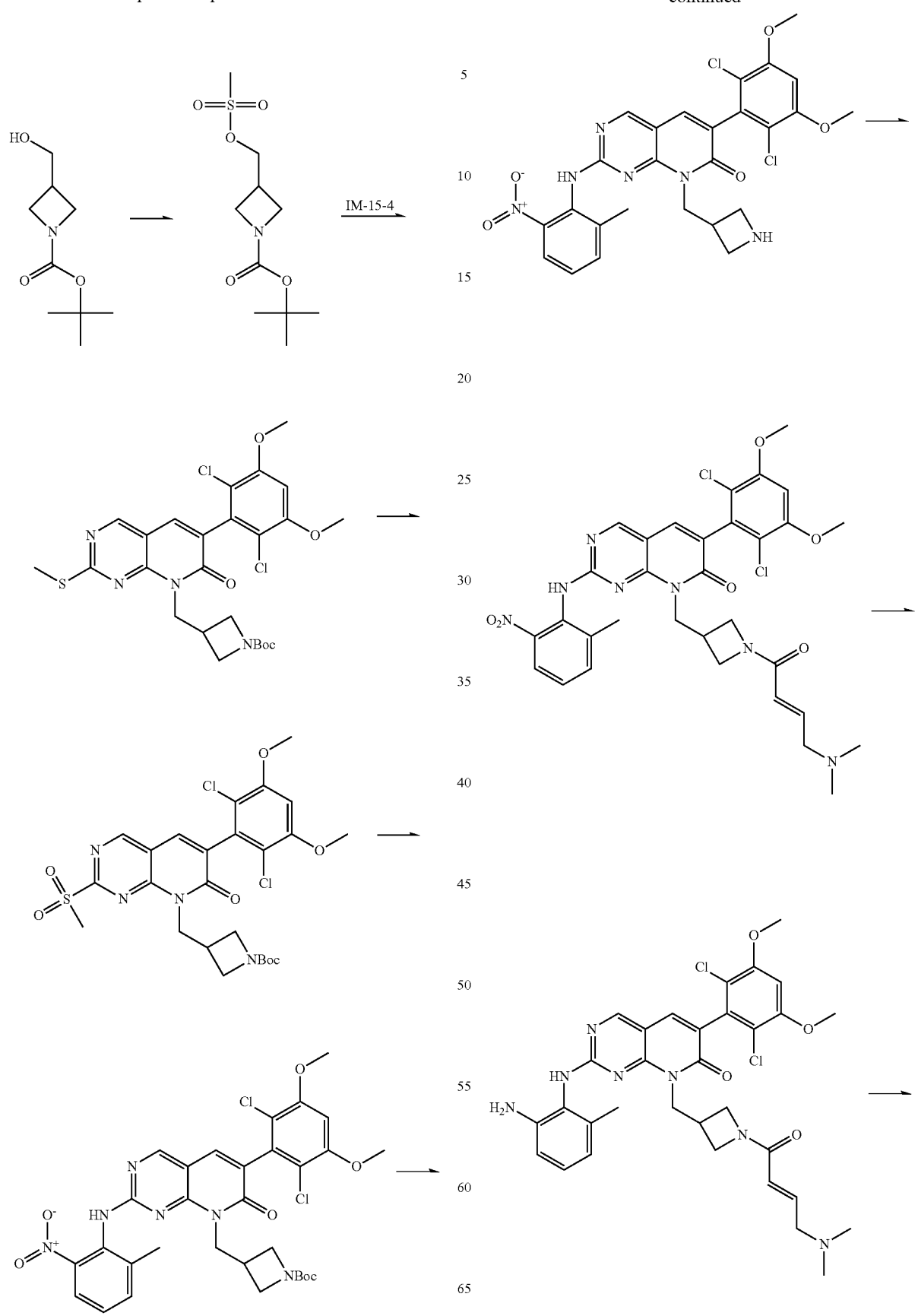

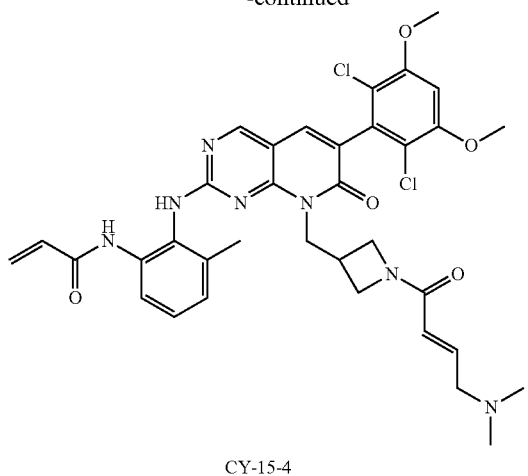

CY-15-4

To a mixture of 1-Boc-3-hydroxymethylazetidine (3.0 g, 16 mmol, 1.0 eq) in MDC (40.0 mL) was added DIPEA (4.14 g, 32 mmol, 2.0 eq) stirred for 15 minutes, followed by addition of mesyl chloride (2.75 g, 24 mmol, 1.5 eq) at 0° C. under $N_2$. The mixture was stirred at 0° C. for 1 hr. TLC (dichloromethane/methanol=9:1, $Rf_{-SM}$=0.30, $Rf$-p=0.60) indicated the starting material was consumed. The reaction was quenched by $NaHCO_3$ aqueous solution, extracted with MDC (30 mL*3). The aqueous phase was separated and the organic phase was washed with brine (60 mL*2), dried with anhydrous $Na_2SO_4$, filtered and concentrated in vacuum to intermediate A (4.0 g, crude), which was obtained as a light yellow solid. LCMS: $(M+H^+)$: 166.10 (Boc fragmented during LCMS).

To a suspension of compound IM-15-4 (1.2 g, 3.0 mmol, 1.0 eq) in acetone (20.0 mL) was added $K_2CO_3$ (0.834 g, 6.0 mmol, 2.0 eq), intermediate-A (1.2 g, 4.5 mmol, 1.5 eq), the mixture was stirred at 80° C. for 18 hrs. TLC (Ethyl acetate/Hexane=5:5, $Rf_{-SM(Int-A)}$=0.71, $Rf_{-P}$=0.4) indicated the starting material was consumed. The organic solvents concentrated in vacuum, residue was extracted with DCM (50 mL*3). The combined organic phase was washed with brine (100 mL*2), dried with anhydrous $Na_2SO_4$, filtered and concentrated in vacuum to intermediate-1 (1.0 g, crude), which was obtained as a light yellow solid. LCMS: $(M+H^+)$: 567.2

To a solution of intermediate 1 (1.0 g, 1.7 mmol, 1.0 eq) in DCM (40.0 mL) was added m-CPBA (1.14 g, 5.2 mmol, 77% purity, 3.0 eq) in several portions at 0° C., the mixture was stirred at 20° C. for 1 hrs. TLC (Ethyl acetate/n-hexane=5:5, $Rf_{-SM}$=0.40, $Rf_{-P}$=0.33) indicated the starting material was consumed. The mixture was quenched by $NaHCO_3$ aqueous solution, and then extracted with DCM (25 mL*3). The combined organic phase was washed with brine (50 mL*2), dried with anhydrous $Na_2SO_4$, filtered and concentrated in vacuum to give intermediate-2 (0.8 g, crude) as a light yellow solid. LCMS: $(M+H^+)$: 621.10 (Int-2+sodium adduct)

To a solution of intermediate-2 (0.8 g, 1.3 mmol, 1.0 eq) and intermediate B (0.213 g, 1.4 mmol, 1.05 eq) in DMF (15 mL) was added t-BuOK (0.228 g, 2.0 mmol, 1.52 eq) at 0° C., the mixture was stirred at 0° C. for 0.5 hr. TLC (Ethyl acetate/n-hexane=0.33, $Rf_{-SM\ (Int-2)}$=0.26, $Rf_{-P}$=0.46) indicated the starting material was consumed. The mixture was quenched with $NH_4Cl$ aqueous solution, extracted with ethyl acetate (50 mL*2). The combined organic phase was washed with brine (100 mL*2), dried with anhydrous $Na_2SO_4$, filtered and concentrated in vacuum. The crude material was purified by column chromatography using neutral silica gel. The product eluted at 65% ethyl acetate in n-hexane to give intermediate-3 (0.9 g), which was obtained as a light yellow solid. LCMS: $(M+H^+)$: 693.27 (Int-3+sodium adduct)

To a solution of Intermediate-3 (0.9 g, 1.3 mmol, 1.0 eq) in MDC (25 mL) was added TFA (0.73 g, 6.7 mmol, 5 eq) at 0° C. and allow to stirred at same temperature for 1 hr. TLC (Chloroform:Methanol=9:1, $Rf_{-SM\ (Int-3)}$=0.66, $Rf_{-P}$=0.13) indicated the starting material was consumed. The mixture was quenched with $NaHCO_3$ aqueous solution, extracted with MDC (25 mL*2). The combined organic phase was washed with brine (100 mL*2), dried with anhydrous $Na_2SO_4$, filtered and concentrated in vacuum to give intermediate-4 (0.65 g, crude) which was obtained as a light yellow solid. LCMS: $(M+H^+)$: 571.22 (Int-4)

To a solution of (E)-4-(dimethylamino)but-2-enoic acid (0.190 g, 1.1 mmol, 1.01 eq) in DMF (10 mL) was added HATU (0.519 g, 1.3 mmol, 1.2 eq), DIPEA (0.442 g, 3.4 mmol, 3.0 eq) at 0° C., to it was added intermediate-4 (0.65 g, 1.1 mmol, 1.0 eq) and allow to stirred at same temperature for 1 hr. TLC (Chloroform:Methanol=9:1, $Rf_{-SM(Int-4)}$=0.13, $Rf_{-P}$=0.3) indicated the starting material was consumed. The reaction mixture was poured into cold water, solid material filtered, dry under vacuum to give intermediate-5 (0.350 g, crude) was obtained as a light yellow solid. LCMS: $(M+H^+)$: 682.30 (Int-5)

To a solution of intermediate-5 (0.35 g, 0.5 mmol, 1.0 eq) in ethanol (5 ml) was added Fe (0.22 g, 4.1 mmol, 8.0 eq), $NH_4Cl$ (0.220 g, 4.1 mmol, 8.0 eq) reaction mixture was heated at 80° C. for 16 hrs. TLC (Chloroform:Methanol=8.5:1.5, Rf-$SM_{(Int-5)}$=0.46, Rf-P=0.31) indicated the starting material was consumed. Ethanol removed under reduced pressure, residue extracted with MDC, filtered with celite, The combined organic phase was washed with brine (100 mL*2), dried with anhydrous $Na_2SO_4$, filtered and concentrated in vacuum to give intermediate-6 (0.22 g, crude) which was obtained as a light yellow solid. LCMS: $(M+H^+)$: 652.37 (Int-6)

To a solution of intermediate-6 (0.22 g, 0.3 mmol, 1 eq) in MDC was added acryloyl chloride (0.03 g, 0.3 mmol, 1.01 eq) at 20° C., allowed to stir at same temperature for 1 hr, TLC (Chloroform:Methanol=8.5:1.5, $Rf_{-SM\ (Int-6)}$=0.31, $Rf_{-P}$=0.48) indicated the starting material was consumed. MDC was removed under vacuum, residue diluted with THF, to it was added DBU (0.103 g, 0.67 mmol, 2 eq) in THF (3 mL) allowed to stir at 20° C. for 2 hrs. (to remove chlorinated adduct of acryloyl chloride). Reaction mixture poured into water and extracted with MDC. The combined organic phase was washed with brine (100 mL*2), dried with anhydrous $Na_2SO_4$, filtered and concentrated in vacuum to give CY-15-4 (0.22 g, crude) was obtained as a light yellow solid, which was purified by preparing HPLC. $^1$H NMR: DMSO 400 MHz δ 9.437 (s, 1H), 9.136 (s, 1H), 8.799 (s, 1H), 7.784-7.754 (d, J=12 Hz, 2H), 7.200-7.181 (d, J=7.6 Hz, 1H), 7.120-7.103 (d, J=6.8, 1H), 6.979 (s, 1H), 6.585-6.517 (m, 2H), 6.240-6.199 (d, J=16.4 Hz, 1H), 5.921-5.885 (d, J=14.4 Hz, 1H), 5.710-5.685 (d, J=10 Hz, 1H), 4.614 (br, 1H), 4.151 (br, 2H), 3.950 (s, 7H), 6.630 (br, 1H), 3.008-2.994 (d, J=5.6, 3H), 2.201 (s, 1H), 2.130 (s, 6H). LCMS: $(M+H^+)$: 706.41.

107
Example 8: Preparation of CY-15-5
108
-continued
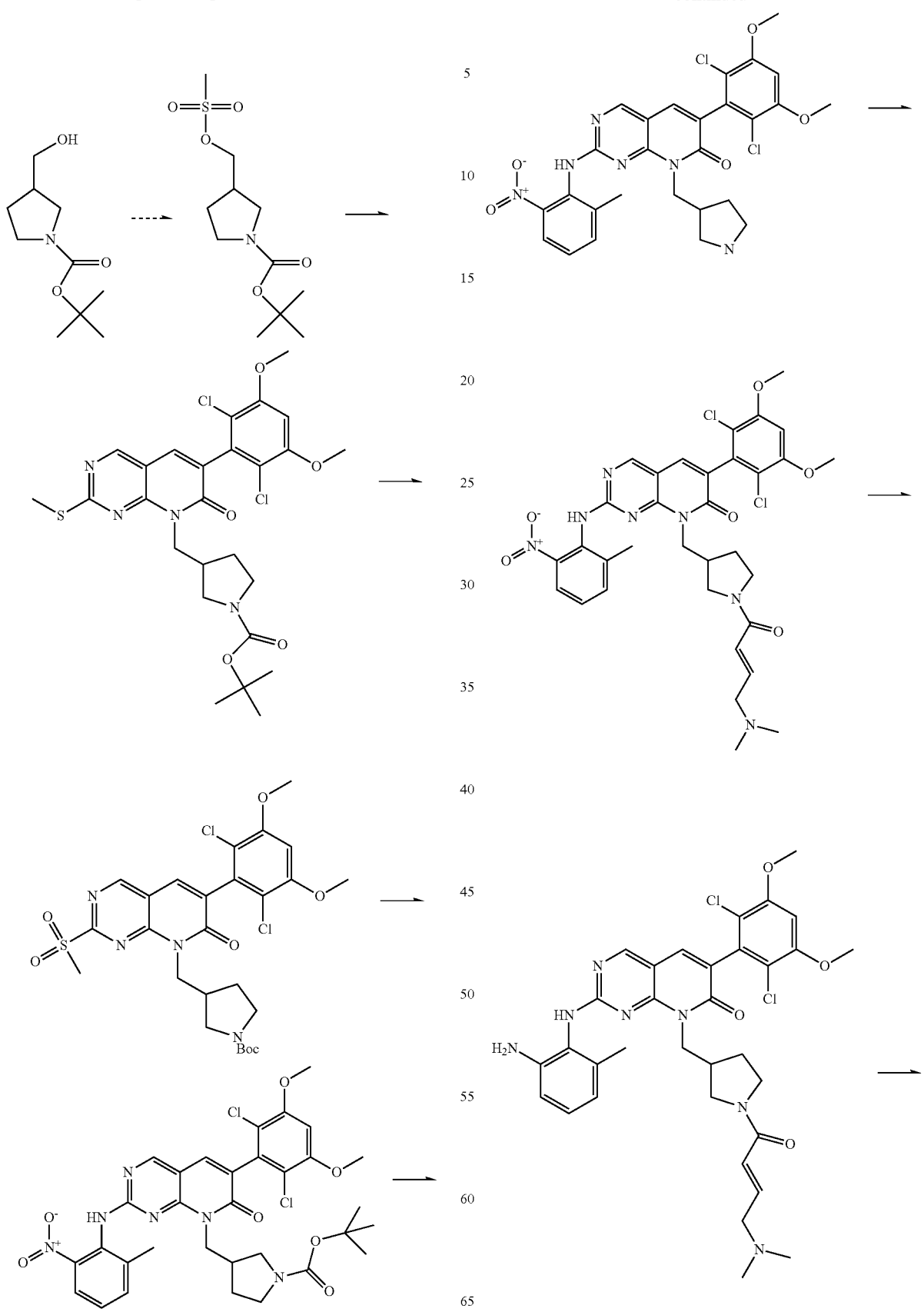

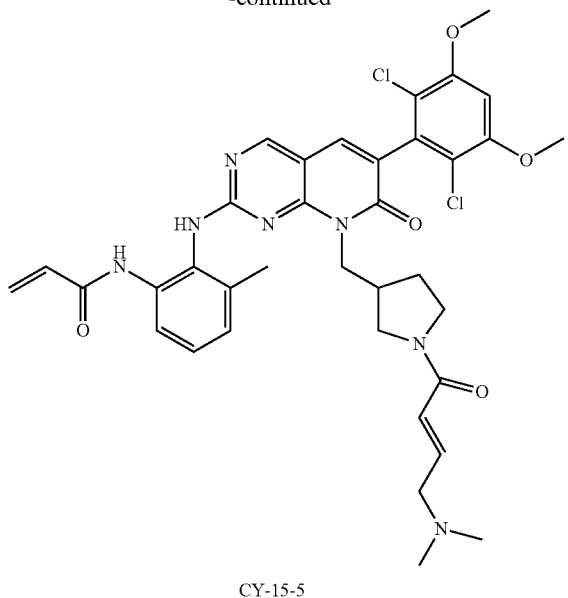

CY-15-5

To a mixture of 1-Boc-3-hydroxymethylpyrrolidine (3.0 g, 14.89 mmol, 1.0 eq) in MDC (40.0 mL) was added DIPEA (3.85 g, 29.79 mmol, 2.0 eq) stirred for 15 mins, followed by addition of mesyl chloride (2.55 g, 22.34 mmol, 1.5 eq) at 0° C. under $N_2$. The mixture was stirred at 0° C. for 1 hr. TLC (dichloromethane/methanol=9:1, $R_{f\text{-}SM}$=0.40, $R_{f\text{-}p}$=0.60) indicated the starting material was consumed. The reaction was quenched by $NaHCO_3$ aqueous solution, extracted with MDC (30 mL*3). The aqueous phase was separated and the organic phase was washed with brine (60 mL*2), dried with anhydrous $Na_2SO_4$, filtered and concentrated in vacuum to compound A (3.9 g, crude), which was obtained as a light yellow solid. LCMS: $(M+H^+)$: 179.98 (Boc fragmented during LCMS)

To a suspension of compound IM-15-4 (1.0 g, 2.5 mmol, 1.0 eq) in acetone (20.0 mL) was added $K_2CO_3$ (0.694 g, 5.0 mmol, 2.0 eq), Intermediate-A (1.054 g, 3.8 mmol, 1.5 eq), the mixture was stirred at 80° C. for 18 hrs. TLC (Ethyl acetate/Hexane=5:5, $R_{f\text{-}SM(Int\text{-}A)}$=0.3, $R_{f\text{-}P}$=0.4) indicated the starting material was consumed. The organic solvents concentrated in vacuum, residue was extracted with DCM (50 mL*3). The combined organic phase was washed with brine (100 mL*2), dried with anhydrous $Na_2SO_4$, filtered and concentrated in vacuum to intermediate-1 (1.0 g, crude) was obtained as a light yellow solid. LCMS: $(M+H^+)$: 603.22 (Intermediate-1 with sodium adduct)

To a solution of intermediate 1 (1.0 g, 1.7 mmol, 1.0 eq) in DCM (40.0 mL) was added m-CPBA (1.16 g, 5.17 mmol, 77% purity, 3.0 eq) in several portions at 0° C., the mixture was stirred at 20° C. for 1 hrs. TLC (Ethyl acetate/n-hexane=5:5, $R_{f\text{-}SM}$=0.40, $R_{f\text{-}P}$=0.2) indicated the starting material was consumed. The mixture was quenched by $NaHCO_3$ aqueous solution, and then extracted with DCM (25 mL*3). The combined organic phase was washed with brine (50 mL*2), dried with anhydrous $Na_2SO_4$, filtered and concentrated in vacuum to give intermediate-2 (0.9 g, crude) which was obtained as a light yellow solid. LCMS: $(M+H^+)$: 635.23 (Int-2+sodium adduct)

To a solution of intermediate-2 (0.9 g, 1.47 mmol, 1.0 eq) and 2-methyl-6-nitro aniline (0.234 g, 2.23 mmol, 1.05 eq) in DMF (15 mL) was added t-BuOK (0.250 g, 2.23 mmol, 1.52 eq) at 0° C., the mixture was stirred at 0° C. for 0.5 hr. TLC (Ethyl acetate/n-hexane 5:5) $Rf\text{-}_{SM\ (Int\text{-}2)}$=0.2, $R_{f\text{-}P}$=0.3) indicated the starting material was consumed. The mixture was quenched with $NH_4Cl$ aqueous solution, extracted with ethyl acetate (150 mL*2). The combined organic phase was washed with brine (100 mL*2), dried with anhydrous $Na_2SO_4$, filtered and concentrated in vacuum. The crude material was purified by column chromatography using neutral silica gel. The product eluted at 55% ethyl acetate in n-hexane to give Intermediate-3 (0.8 g) was obtained as a light yellow solid. LCMS: $(M+H^+)$: 707.34 (Int-3+sodium adduct)

To a solution of Intermediate-3 (0.8 g, 1.16 mmol, 1.0 eq) in MDC (25 mL) was added TFA (0.67 g, 5.8 mmol, 5 eq) at 0° C. and allow to stirred at same temperature for 1 hr. TLC (Chloroform:Methanol=9:1, $Rf\text{-}_{SM\ (Int\text{-}3)}$=0.4, $R_{f\text{-}P}$=0.2) indicated the starting material was consumed. The mixture was quenched with $NaHCO_3$ aqueous solution, extracted with MDC (25 mL*2). The combined organic phase was washed with brine (100 mL*2), dried with anhydrous $Na_2SO_4$, filtered and concentrated in vacuum to give intermediate-4 (0.5 g, crude) was obtained as a light yellow solid. LCMS: $(M+H^+)$: 571.22 (Int-4)

To a solution of (E)-4-(dimethylamino)but-2-enoic acid (0.212 g, 1.28 mmol, 1.01 eq) in DMF (10 mL) was added HATU (0.39 g, 1.3 mmol, 1.2 eq), DIPEA (0.442 g, 3.4 mmol, 3.0 eq) at 0° C., to it was added intermediate-4 (0.65 g, 1.02 mmol, 1.2 eq) and allow to stirred at same temperature for 1 hr. TLC (Chloroform:Methanol=9:1, $Rf\text{-}_{SM(Int\text{-}4)}$=0.2, $R_{f\text{-}P}$=0.3) indicated the starting material was consumed. The reaction mixture was poured into cold water, solid material filtered, dry under vacuum to give intermediate-5 (0.4 g, crude) was obtained as a light yellow solid. LCMS: $(M+H^+)$: 696.20 (Int-5)

To a solution of intermediate-5 (0.25 g, 0.36 mmol, 1.0 eq) in ethanol (5 ml) was added Fe (0.16 g, 2.87 mmol, 8.0 eq), $NH_4Cl$ (0.154 g, 2.87 mmol, 8.0 eq), reaction mixture was heated at 80° C., for 16 hrs. TLC (Chloroform:Methanol=8.5:1.5, $Rf\text{-}SM_{(Int\text{-}5)}$=0.5, Rf-P=0.3) indicated the starting material was consumed. Ethanol removed under reduced pressure, residue extracted with MDC, filtered with celite, The combined organic phase was washed with brine (100 mL*2), dried with anhydrous $Na_2SO_4$, filtered and concentrated in vacuum to give intermediate-6 (0.18 g, crude), which was obtained as a light yellow solid. LCMS: $(M+H^+)$: 666.35 (Int-6)

To a solution of Intermediate-6 (0.18 g, 0.27 mmol, 1 eq) in MDC was added acryloyl chloride (0.024 g, 0.27 mmol, 1.01 eq) at 20° C., allowed to stir at same temperature for 1 hr, TLC (Chloroform:Methanol=8.5:1.5, $Rf\text{-}_{SM(Int\text{-}6)}$=0.31, $R_{f\text{-}P}$=0.48) indicated the starting material was consumed. MDC was removed under vacuum, residue diluted with THF, to it was added DBU (0.082 g, 0.54 mmol, 2 eq) allowed to stir at 20° C. for 2 hrs. Reaction mixture poured into water and extracted with MDC. The combined organic phase was washed with brine (100 mL*2), dried with anhydrous $Na_2SO_4$, filtered and concentrated in vacuum to give NW-15-5 (0.18 g, crude), which was obtained as a light yellow solid, which was purified by prep. HPLC using following method. $^1H$ NMR: DMSO 400 MHz δ 9.459 (s, 1H), 9.095 (s, 1H), 8.807 (s, 1H), 7.789 (s, 2H), 7.240-7.201 (m, 1H), 7.110 (s, 1H), 6.981 (s, 1H), 6.604-6.520 (m, 2H), 6.260-6.127 (m, 2H), 5.677-5.652 (d, J=10 Hz, 1H), 4.408 (s, 1H), 3.951 (s, 7H), 3.323-3.259 (br, 1H), 2.995-2.981 (br, 2H), 2.871-2.859 (br, 1H), 2.332-2.296 (br, 1H), 2.194-2.086 (br, 10H), 1.545-1.530 (br, 1H), 1.289 (s, 2H). LCMS: $(M+H^+)$: 720.

Example 9: Preparation of CY-15-6
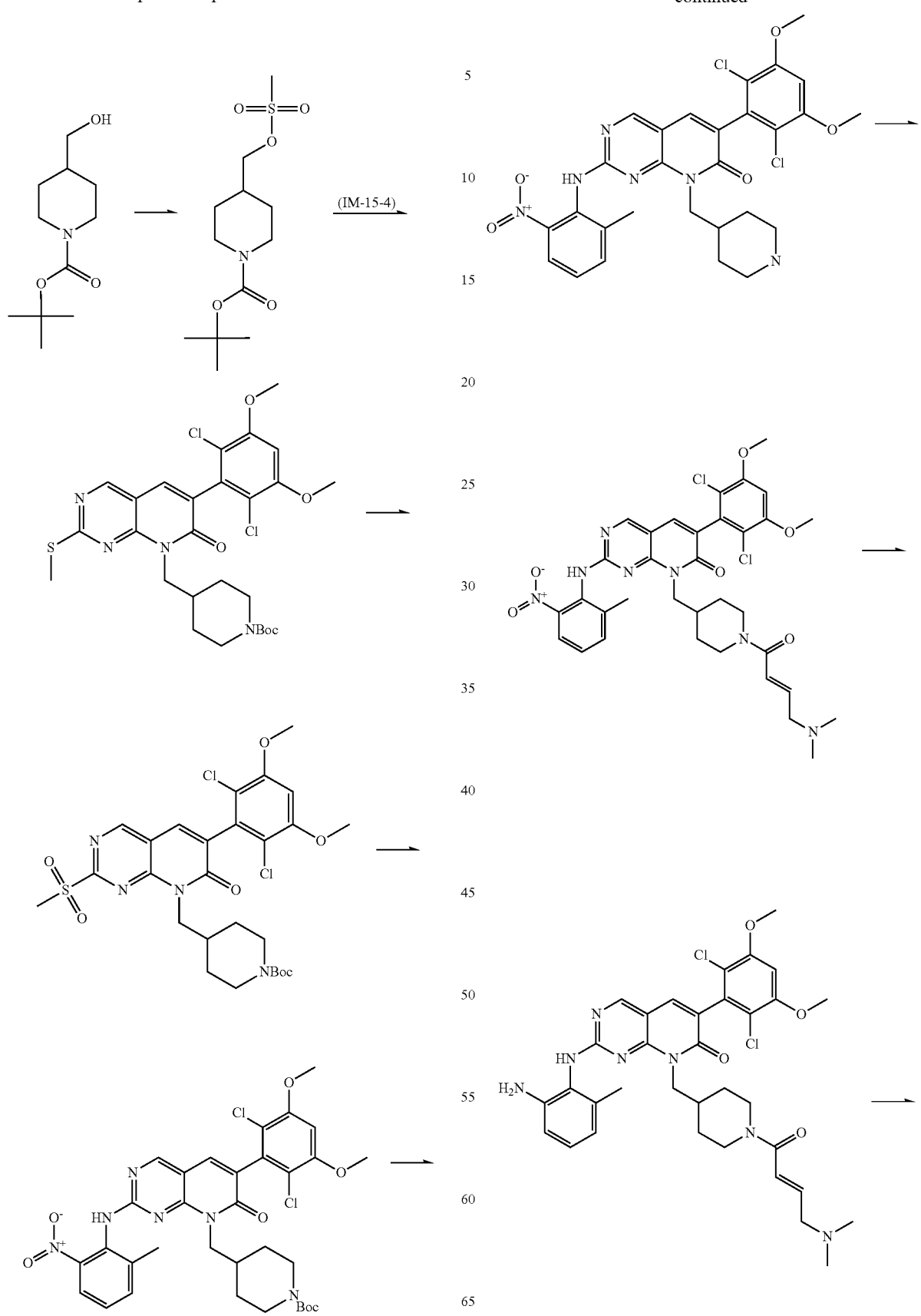

-continued

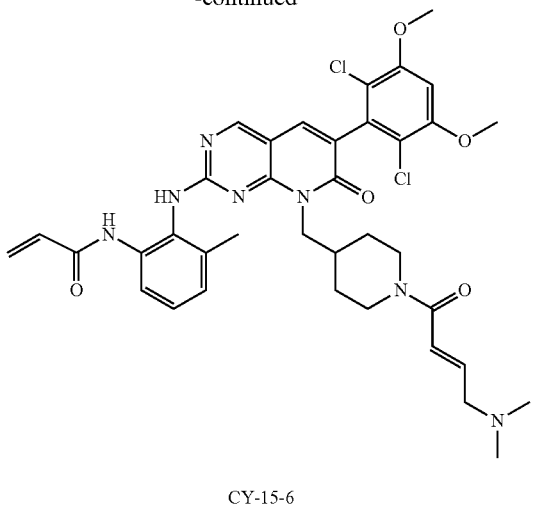

CY-15-6

To a mixture of 1-Boc-3-hydroxymethylpiperidine (3.0 g, 13.9 mmol, 1.0 eq) in MDC (40.0 mL) was added DIPEA (3.6 g, 27.8 mmol, 2.0 eq) and the reaction mixture was stirred for 15 minutes followed by addition of mesyl chloride (2.4 g, 20.8 mmol, 1.5 eq) at 0° C. under $N_2$. The mixture was stirred at same temperature for 1 hr. TLC (chloroform/methanol=9:1, $R_f$-$_{SM}$=0.32, $R_f$-p=0.47) indicated the starting material was consumed. The reaction was quenched by $NaHCO_3$ aqueous solution, extracted with MDC (30 mL*3). The aqueous phase was separated and the organic phase was washed with brine (60 mL*2) dried with anhydrous $Na_2SO_4$, filtered and concentrated in vacuum to compound A (4.0 g, crude) which was obtained as a light yellow solid. LCMS: (M+H$^+$): 194.05 (Boc fragmented during LCMS)

To a suspension of compound IM-15-4 (0.9 g, 2.26 mmol, 1.0 eq) in acetone (30.0 mL) was added $K_2CO_3$ (0.607 g, 4.5 mmol, 2.0 eq), Intermediate-A (0.996 g, 3.4 mmol, 1.5 eq) and the mixture was stirred at 80° C. for 18 hrs. TLC (Ethyl acetate/Hexane=5:5, $R_f$-$_{SM(Int-A)}$=0.58, $R_f$-$_P$=0.41) indicated the starting material was consumed. The organic solvents concentrated in vacuum, residue was extracted with DCM (50 mL*3). The combined organic phase was washed with brine (50 mL*2), dried with anhydrous $Na_2SO_4$, filtered and concentrated in vacuum to Intermediate-1 (1.2 g, crude) which was obtained as a light yellow solid. LCMS: (M+H$^+$): 595.24

To a solution of intermediate 1 (1.2 g, 2.0 mmol, 1.0 eq) in MDC (60.0 mL) was added m-CPBA (1.34 g, 6.0 mmol, 77% purity, 3.0 eq) in several portions at 0° C., the mixture was stirred at 20° C. for 1 hrs. TLC (Ethyl acetate/n-hexane=5:5, $R_f$-$_{SM}$=0.41, $R_f$-$_P$=0.29) indicated the starting material was consumed, the reaction mixture was quenched by $NaHCO_3$ aqueous solution, and then extracted with DCM (25 mL*3). The combined organic phase was washed with brine (50 mL*2), dried with anhydrous $Na_2SO_4$, filtered and concentrated in vacuum to give intermediate-2 (1.15 g, crude), which was obtained as a light yellow solid. LCMS: (M+H$^+$): 649.21 (Int-2+sodium adduct)

To a solution of intermediate-2 (1.15 g, 1.8 mmol, 1.0 eq) and intermediate B (0.293 g, 1.9 mmol, 1.05 eq) in DMF (15 mL) was added t-BuOK (0.307 g, 2.7 mmol, 1.52 eq) at 0° C., the mixture was stirred at 0° C. for 0.5 hr. TLC (Ethyl acetate/n-hexane=5:5, Rf-$_{SM\ (Int-2)}$=0.29, $R_f$-$_P$=0.39) indicated the starting material was consumed. The reaction mixture was poured into water, extracted with ethyl acetate (50 mL*2). The combined organic phase was washed with brine (50 mL*2), dried with anhydrous $Na_2SO_4$, filtered and concentrated in vacuum. The crude material was purified by column chromatography using neutral silica gel. The product eluted at 70% ethyl acetate in n-hexane to give intermediate-3 (0.9 g, 88% purity) was obtained as a light yellow solid. LCMS: (M+H$^+$): 721(Int-3+sodium adduct)

To a solution of intermediate-3 (0.9 g, 1.3 mmol, 1.0 eq) in MDC (15 mL) was added TFA (0.73 g, 6.4 mmol, 5 eq) at 0° C. and allow to stirred at same temperature for 1 hr. TLC (Chloroform:Methanol=9:1, Rf-$_{SM(Int-3)}$=0.63, $R_f$-$_P$=0.17) indicated the starting material was consumed. The mixture was quenched with $NaHCO_3$ aqueous solution, extracted with MDC (25 mL*2). The combined organic phase was washed with brine (50 mL*2), dried with anhydrous $Na_2SO_4$, filtered and concentrated in vacuum to give Intermediate-4 (0.7 g, crude) was obtained as a light yellow solid. LCMS: (M+H$^+$): 599.26 (Int-4)

To a solution of (E)-4-(dimethylamino)but-2-enoic acid (0.156 g, 1.21 mmol, 1.01 eq) in DMF (5 mL) was added HATU (0.533 g, 1.4 mmol, 1.2 eq), DIPEA (0.464 g, 3.6 mmol, 3.0 eq) at 0° C., to it was added intermediate-4 (0.7 g, 1.2 mmol, 1.0 eq) and allow to stirred at same temperature for 1 hr. TLC (Chloroform:Methanol=8:2, Rf-$_{SM\ (Int-4)}$=0.45, $R_f$-$_P$=0.33) indicated the starting material was consumed. The reaction mixture was poured into cold water, solid material filtered, dry under vacuum to give intermediate-5 (0.7 g, crude) was obtained as a light yellow solid. LCMS: (M+H$^+$): 710.34 (Int-5)

To a solution of intermediate-5 (0.7 g, 0.98 mmol, 1.0 eq) in ethanol (7 ml) was added Fe (0.44 g, 7.8 mmol, 8.0 eq), $NH_4Cl$ (0.422 g, 7.8 mmol, 8.0 eq), reaction mixture was heated at 80° C. for 16 hrs. TLC (Chloroform:Methanol=8:2, Rf-SM (Int-5)=0.33, Rf-P=0.22) indicated the starting material was consumed. Ethanol removed under reduced pressure, residue extracted with MDC, filtered with celite, The combined organic phase was washed with brine (50 mL*2), dried with anhydrous $Na_2SO_4$, filtered and concentrated in vacuum to give intermediate-6 (0.6 g, crude) which was obtained as a light yellow solid. LCMS: (M+H$^+$): 680.24 (Int-6)

To a solution of acrylic acid (0.064 g, 0.88 mmol, 1.01 eq) in DMF (8 mL) was added HATU (0.40 g, 1.6 mmol, 1.2 eq), DIPEA (0.34 g, 2.6 mmol, 3.0 eq) at 0° C., to it was added intermediate-6 (0.6 g, 1.0 mmol, 1.0 eq) and allow to stirred at same temperature for 1 hr. TLC (Chloroform:Methanol=8:2, Rf-$_{SM\ (Int-6)}$=0.22, $R_f$-$_P$=0.47) indicated the starting material was consumed. The reaction mixture was poured into cold water, solid material filtered, dry under vacuum to give CY-15-6 (0.6 g, crude) was obtained as a light yellow solid, which was purified by prep. HPLC $^1$H NMR: DMSO 400 MHz δ 9.417 (s, 1H), 9.036 (s, 1H), 8.791 (s, 1H), 7.766-7.824 (d, J=6.8 Hz, 2H), 7.188-7.226 (d, J=7.6 Hz, 1H), 7.105-7.123 (d, J=7.2, 1H), 6.979 (s, 1H), 6.548 (m, 3H), 6.194-6.241 (dd, J=18.4 Hz, 2 Hz, 1H), 5.684-5.711 (d, J=10.8 Hz, 1H), 4.161-4.309 (br, 2H), 3.949 (s, 6H), 3.765-3.744 (d, J=8.4, 3H), 3.483-3.494 (d, J=4.4 Hz, 1H), 3.010 (s, 2H), 2.193 (s, 3H), 2.137 (s, 6H), 1.706 (s, 1H), 1.148 (br, 2H), 0.793-0.854 (br, 2H). LCMS: (M+H$^+$): 734.53

Example 10: Preparation of CY-15-7
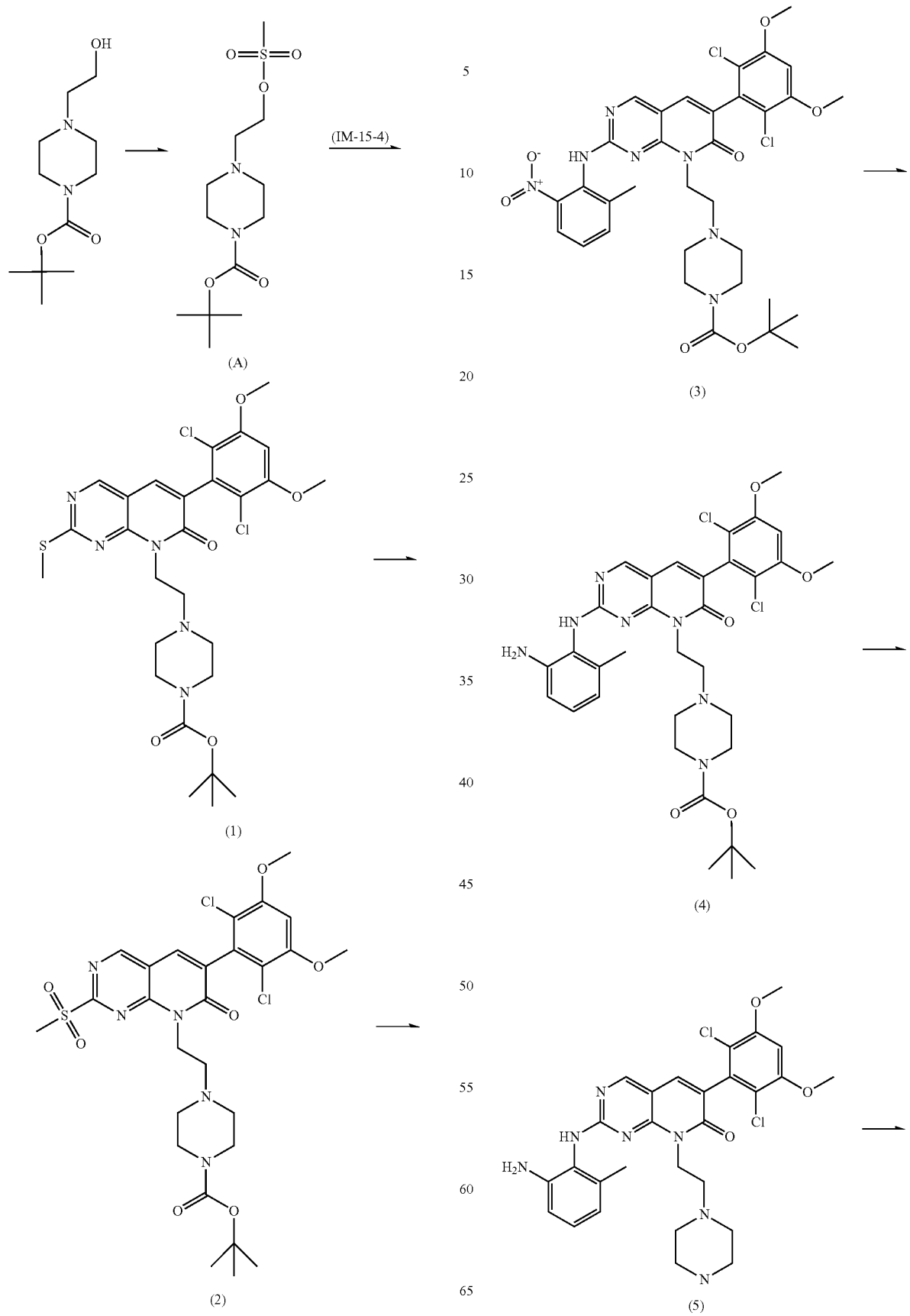

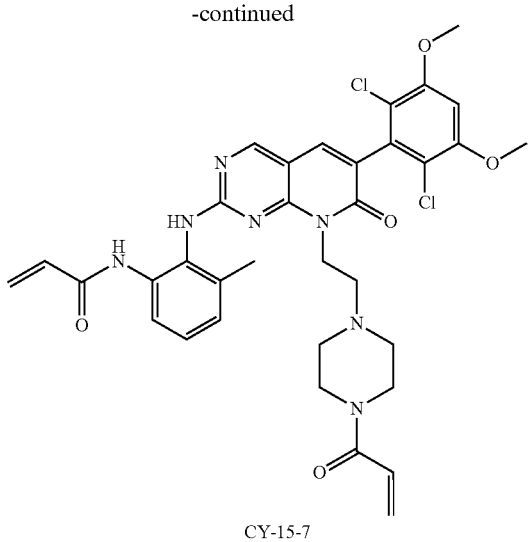

CY-15-7

To a mixture of tert-butyl 4-(2-hydroxyethyl) piperazine-1-carboxylate (2.0 g, 8.6 mmol, 1.0 eq) in MDC (40.0 mL) was added DIPEA (2.24 g, 17.0 mmol, 2.0 eq) stirred for 15 mins, followed by addition of mesyl chloride (1.49 g, 13.0 mmol, 1.5 eq) at 0° C. under $N_2$. The mixture was stirred at 0° C. for 1 hr. TLC (dichloromethane/methanol= 9:1, $R_{f\text{-}SM}$=0.3, $R_{f\text{-}P}$=0.66) indicated the starting material was consumed. The reaction was quenched by NaHCO3 aqueous solution, extracted with MDC (30 mL*3). The aqueous phase was separated and the organic phase was washed with brine (60 mL*2), dried with anhydrous $Na_2SO_4$, filtered and concentrated in vacuum to compound A (2.5 g, crude) was obtained as a light yellow solid.

To a suspension of compound IM-15-4 (0.8 g, 2.0 mmol, 1.0 eq) in acetone (40.0 mL) was added $K_2CO_3$ (0.556 g, 4.0 mmol, 2.0 eq), intermediate-A (0.931 g, 3.0 mmol, 1.5 eq) the mixture was stirred at 80° C. for 18 hrs. TLC (Ethyl acetate/Hexane=5:5, $R_{f\text{-}SM(Int\text{-}A)}$=0.7, $R_{f\text{-}P}$=0.4) indicated the starting material was consumed. The organic solvents concentrated in vacuum, residue was extracted with DCM (50 mL*3). The combined organic phase was washed with brine (100 mL*2), dried with anhydrous $Na_2SO_4$, filtered and concentrated in vacuum to intermediate-1 (0.7 g, crude) was obtained as a light yellow solid. LCMS: (M+H$^+$): 610.15

To a solution of intermediate 1 (0.7 g, 1.1 mmol, 1.0 eq) in acetic acid (8 mL) was added N-chlorosuccinimide (0.613 g, 4.5 mmol, 4.0 eq), triethylamine (0.174 g, 1.7 mmol, 1.5 eq) at 0° C., then mixture was stirred at 20° C. for 1 hrs. TLC (Ethyl acetate/n-hexane=5:5, $R_{f\text{-}SM}$=0.4, $R_{f\text{-}P}$=0.28) indicated the starting material was consumed. The mixture was quenched by NaHCO$_3$ aqueous solution, and then extracted with DCM (25 mL*3). The combined organic phase was washed with brine (50 mL*2), dried with anhydrous $Na_2SO_4$, filtered and concentrated in vacuum to give intermediate-2 (0.65 g, crude) which was obtained as a light yellow solid. LCMS: (M+H$^+$): 642.26 (Int-2)

To a solution of intermediate-2 (0.65 g, 1.0 mmol, 1.0 eq) and intermediate B (0.161 g, 1.0 mmol, 1.05 eq) in DMF (15 mL) was added t-BuOK (0.172 g, 1.5 mmol, 1.52 eq) at 0° C., the mixture was stirred at 0° C. for 0.5 hr. TLC (Ethyl acetate=100%, $R_{f\text{-}SM\,(Int\text{-}2)}$=0.322, $R_{f\text{-}P}$=0.38) indicated the starting material was consumed. The mixture was quenched with NH$_4$Cl aqueous solution, extracted with ethyl acetate (150 mL*2). The combined organic phase was washed with brine (100 mL*2), dried with anhydrous $Na_2SO_4$, filtered and concentrated in vacuum. The crude material was purified by column chromatography using neutral silica gel. The product eluted at 60% ethyl acetate in n-hexane to give Intermediate-3 (0.550 g) which was obtained as a light yellow solid. LCMS: (M+H$^+$): 714.38

To a solution of intermediate-3 (0.55 g, 0.77 mmol, 1.0 eq) in ethanol (7 ml) was added Fe (0.34 g, 6.1 mmol, 8.0 eq), NH$_4$Cl (0.33 g, 6.1 mmol, 8.0 eq), reaction mixture was heated at 80° C., for 16 hrs. TLC (Ethyl acetate, Rf-SM$_{(Int\text{-}3)}$=0.38, Rf-P=0.34) indicated the starting material was consumed. Ethanol removed under reduced pressure, residue extracted with MDC, filtered with celite, The combined organic phase was washed with brine (100 mL*2), dried with anhydrous Na2SO4, filtered and concentrated in vacuum to give intermediate-4 (0.450 g, crude) was obtained as a light yellow solid. LCMS: (M+H$^+$): 684.46 (Int-4)

To a solution of intermediate-4 (0.45 g, 0.65 mmol, 1.0 eq) in MDC was added TFA (0.375 g, 3.2 mmol, 5 eq) at 0° C. and allow to stirred at same temperature for 1 hr. TLC (Chloroform:Methanol=9:1, $Rf\text{-}_{SM\,(Int\text{-}4)}$=0.53, $R_{f\text{-}P}$=0.18) indicated the starting material was consumed. The mixture was quenched with NaHCO$_3$ aqueous solution, extracted with MDC (25 mL*2). The combined organic phase was washed with brine (100 mL*2), dried with anhydrous $Na_2SO_4$, filtered and concentrated in vacuum to give intermediate-5 (0.38 g, crude) was obtained as a light yellow solid. LCMS: (M+H$^+$): 584.42 (Int-5)

To a solution of intermediate-5 (0.38 g, 0.3 mmol, 1 eq) in MDC was added acryloyl chloride (0.129 g, 1.4 mmol, 2.2 eq) at 20° C., allowed to stir at same temperature for 1 hr, TLC (Chloroform:Methanol=9:1, Rf-$_{SM\,(Int\text{-}5)}$=0.17, $R_{f\text{-}P}$=0.43) indicated the starting material was consumed. MDC was removed under vacuum, residue diluted with THF, to it was added DBU (0.2 mL) allowed to stir at 20° C. for 2 hrs. reaction mixture poured into water and extracted with MDC. The combined organic phase was washed with brine (100 mL*2), dried with anhydrous Na2SO4, filtered and concentrated in vacuum to give CY-15-7 (0.240 g, crude) was obtained as a light yellow solid, which was purified by prep-HPLC. LCMS: (M+H$^+$): 692.36 $^1$H NMR: CDCl$_3$ 400 MHz δ 8.575-8.516 (s, 2H), 7.721-7.709 (d, J=4.8, 2H), 7.482 (s, 1H), 7.302-7.264 (t, J=7.6 Hz, 2H), 7.201-7.183 (d, J=7.2 Hz, 1H), 6.628 (s, 1H), 6.533-6.426 (m, 2H), 6.331-6.265 (m, 2H), 5.748-5.709 (m, 2H), 4.396 (br, 2H), 3.954 (s, 6H), 3.501-3.468 (br, 4H), 2.795-2.781 (br, 2H), 2.598 (br, 2H), 2.321 (s, 5H).

Example 11: Preparation of CY-15-8

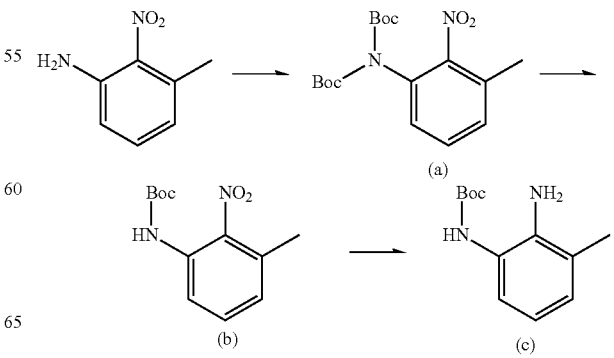

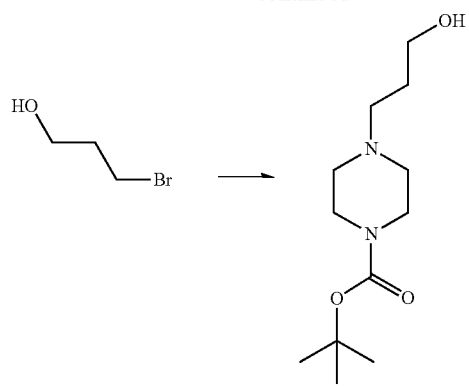

(A)

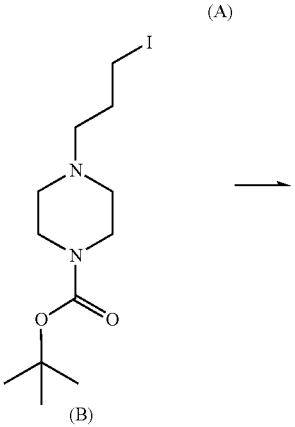

(B)

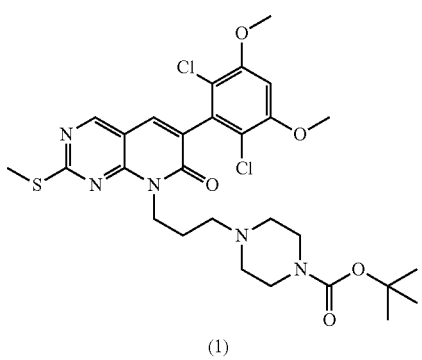

(1)

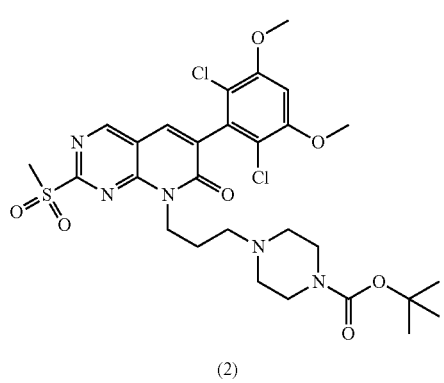

(2)

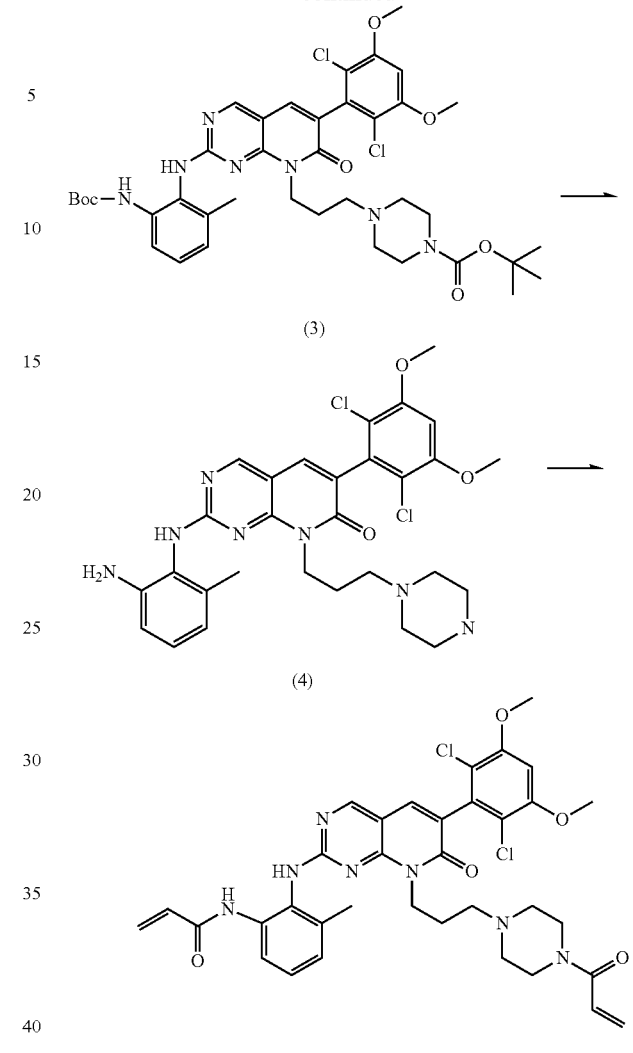

(3)

(4)

CY-15-8

To a mixture of 3-methyl-2-nitro aniline (0.5 g, 3.28 mmol, 1.0 eq) in THF (25 mL) was added Boc anhydride (1.5 g, 6.90 mmol, 2.1 eq), DMAP (0.004 g, 0.32 mmol, 0.01 eq), allowed to stir at 20° C. for 16 hrs. TLC (Ethyl acetate/n-Hexane=1:9, $R_{f\,SM(3\text{-}methyl\text{-}2\text{-}nitro\ aniline)}$=0.392, $R_f$-p=0.321) indicated the starting material was consumed. The reaction was extracted with ethyl acetate (30 mL*3). The aqueous phase was separated and the organic phase was washed with brine (60 mL*2), dried with anhydrous $Na_2SO_4$, filtered and concentrated in vacuum to compound A (1.15 g, crude) was obtained as a white solid.

To a solution of intermediate-a (1.15 g, 3.26 mmol, 1.0 eq) in MDC (25 mL) was added trifluoroacetic acid (0.74 g, 6.53 mmol, 2.1 eq) at 0° C., and allowed to stir at same temperature for 2 hrs. TLC (Ethyl acetate/n-Hexane=1:9, $R_{f\,SM(a)}$=0.33, $R_f$p=0.56) indicated the starting material was consumed. The reaction was neutralized with $NaHCO_3$, extracted with MDC (30 mL*3). The aqueous phase was separated and the organic phase was washed with brine (60 mL*2), dried with anhydrous $Na_2SO_4$, filtered and concentrated in vacuum to compound b (0.82 g, crude) was obtained as a white solid.

To a suspension of palladium on charcoal (0.08 g, 10% w/w) in methanol under $N_2$ was added intermediate-b (0.82 g, 3.25 mmol, 1 eq), purged with H$_2$ gas for 2 hrs. TLC (Ethylacetate/n-Hexane=1:9, R$_f$-SM(a)=0.53, R$_f$-p=0.36) indicated the starting material was consumed. The reaction was filtered with celite, filtrate removed under vacuum, residue triturated with n-hexane, which was obtained intermediate-c (0.6 g) which was obtained as a white solid, confirmed by 1H NMR. $^1$H NMR: CDCl$_3$ 400 MHz δ 8.273 (s, 1H), 7.028-7.008 (d, J=8 Hz, 1H), 6.779-6.761 (d, J=7.2 Hz, 1H), 6.478-6.440 (t, J=7.6 Hz, 1H), 4.538 (br, 2H) 2.079 (s, 3H), 1.455 (s, 9H).

To a mixture of 1-Boc-piperazine (1.0 g, 3.59 mmol, 1.0 eq), 3-bromopropan-1-ol (1.34 g, 3.59 mmol, 1 eq) in acetonitrile (25.0 mL) was added K$_2$CO$_3$ (1.9 g, 6.1 mmol, 1.7 eq) stirred at 80° C. for 16 hrs, TLC (dichloromethane/methanol=9:1, R$_f$-SM(N-boc piperazine)=0.3, R$_f$-p=0.39) indicated the starting material was consumed. The reaction was extracted with ethyl acetate (30 mL*3). The aqueous phase was separated and the organic phase was washed with brine (60 mL*2), dried with anhydrous Na$_2$SO$_4$, filtered and concentrated in vacuum to compound A (1.3.0 g, crude) was obtained as a white solid. LCMS: (M+H$^+$): 245.11

To a solution of Intermediate-A (1.3 g, 5.32 mmol, 1.0 eq) was added Imidazole (0.72 g, 10.65 mmol, 2 eq), triphenylphosphine (2.79 g, 10.65 mmol, 2.0 eq), allow to stir at room temperature for 15 minutes, followed by addition of iodine (2.02 g, 7.98 mmol, 1.5 eq) portion wise, reaction mixture allowed to stir at room temperature for 5 hrs. TLC (Ethyl acetate=100%, R$_f$-SM(A)=0.17, R$_f$-p(B)=0.70) indicated the starting material was consumed. The reaction extracted with MDC (30 mL*3). The aqueous phase was separated and the organic phase was washed with brine (60 mL*2), dried with anhydrous Na$_2$SO$_4$, filtered and concentrated in vacuum to compound B (1.0 g, crude), which was purified by column chromatography, product eluted at 50% ethyl acetate in n-hexane. After purification intermediate B (0.65 g) was obtained as a white solid. LCMS: mass not supported, used as such in next step.

To a suspension of compound IM-15-4 (0.6 g, 1.51 mmol, 1.0 eq) in acetone (30.0 mL) was added K$_2$CO$_3$ (0.229 g, 1.66 mmol, 1.1 eq), intermediate-B (0.641 g, 1.8 mmol, 1.2 eq), the mixture was stirred at 80° C. for 6 hrs. TLC (Ethyl acetate=100%, R$_f$-SM(IM-15-4)=0.68, R$_f$-P=0.53) indicated the starting material was consumed. The organic solvents concentrated in vacuum, residue was extracted with DCM (50 mL*3). The combined organic phase was washed with brine (100 mL*2), dried with anhydrous Na$_2$SO$_4$, filtered and concentrated in vacuum to intermediate-1 (0.96 g, crude) was obtained as a light yellow solid. LCMS: (M+H$^+$): 624.26

To a solution of intermediate 1 (0.6 g, 0.96 mmol, 1.0 eq) in acetic acid (8 mL) was added N-chlorosuccinimide (0.514 g, 3.83 mmol, 4.0 eq), triethylamine (0.146 g, 1.4 mmol, 1.5 eq) at 0° C., then mixture was stirred at 20° C. for 1 hrs. TLC (Ethyl acetate=100%, R$_f$-SM=0.571, R$_f$-P=0.542) indicated the starting material was consumed. The mixture was quenched by NaHCO$_3$ aqueous solution, and then extracted with DCM (25 mL*3). The combined organic phase was washed with brine (50 mL*2), dried with anhydrous Na$_2$SO$_4$, filtered and concentrated in vacuum to give intermediate-2 (0.55 g, crude) as a light yellow solid. LCMS: (M+H$^+$): 672.23 (Int-2 with sodium adduct)

To a solution of intermediate-2 (0.55 g, 0.83 mmol, 1.0 eq) and intermediate C (0.194 g, 0.88 mmol, 1.05 eq) in DMF (15 mL) was added t-BuOK (0.139 g, 1.24 mmol, 1.52 eq) at 0° C., the mixture was stirred at 0° C. for 0.5 hr. TLC (Ethyl acetate=100%, Rf-$_{SM\ (Int-2)}$=0.53, R$_f$-P=0.59) indicated the starting material was consumed. The mixture was quenched with NH$_4$Cl aqueous solution, extracted with ethyl acetate (150 mL*2). The combined organic phase was washed with brine (100 mL*2), dried with anhydrous Na$_2$SO$_4$, filtered and concentrated in vacuum. The crude material was purified by column chromatography using neutral silica gel. The product eluted at 60% ethyl acetate in n-hexane to give intermediate-3 (0.47 g) was obtained as a light yellow solid. LCMS: (M+H$^+$): 798.6 (Int-3)

To a solution of intermediate-3 (0.47 g, 0.58 mmol, 1.0 eq) in MDC was added TFA (0.336 g, 2.9 mmol, 5 eq) at 0° C. and allow to stirred at same temperature for 1 hr. TLC (Chloroform:Methanol=9:1, Rf-$_{SM\ (Int-3)}$=0.64, R$_f$-P=0.15) indicated the starting material was consumed. The mixture was quenched with NaHCO$_3$ aqueous solution, extracted with MDC (25 mL*2). The combined organic phase was washed with brine (100 mL*2), dried with anhydrous Na$_2$SO$_4$, filtered and concentrated in vacuum to give intermediate-4 (0.16 g) was obtained as a light yellow solid.

To a solution of intermediate-4 (0.16 g, 0.26 mmol, 1 eq) in MDC (5 mL) was added acryloyl chloride (0.053 g, 0.58 mmol, 2.2 eq) at 20° C., allowed to stir at same temperature for 1 hr, TLC (Chloroform:Methanol=9:1, Rf-$_{SM\ (Int-4)}$=0.15, R$_f$-P=0.69) indicated the starting material was consumed. MDC was removed under vacuum, residue diluted with THF, to it was added DBU (0.040 g, 0.54 mmol, 2 eq) allowed to stir at 20° C. for 2 hrs. Reaction mixture poured into water and extracted with MDC. The combined organic phase was washed with brine (100 mL*2), dried with anhydrous Na$_2$SO$_4$, filtered and concentrated in vacuum to give CY-15-8 (0.110 g, crude) was obtained as a light yellow solid, which was purified by prep. HPLC. $^1$H NMR: CDCl$_3$ 400 MHz δ 8.566 (s, 1H), 8.106 (s, 1H), 7.727-7.748 (d, J=8.4, 1H), 7.499-7.468 (m, 1H), 7.296-7.257 (m, 1H), 7.204-7.185 (m, 1H), 7.130-7.111 (d, J=7.6 Hz, 1H), 6.629 (s, 1H), 6.565-6.279 (m, 4H), 5.836-5.717 (m, 2H), 4.416-4.383 (t, J=6.4, 1H), 3.956 (s, 6H), 3.661-3.602 (br, 3H), 2.497-2.480 (br, 5H), 2.375-2.192 (m, 4H), 2.029-1.898 (m, 1H), 1.701 (s, 1H), 1.269 (s, 1H), 1.233-1.217 (d, J=6.4 Hz, 1H). LCMS: (M+H$^+$): 706.46

Example 12: Preparation of Additional Compounds

The compounds below were prepared by methods substantially identical, similar, or analogous to those disclosed in examples 7-11.

| Example | Structure | m/z (MH+) |
|---------|-----------|-----------|
| 12-1 | 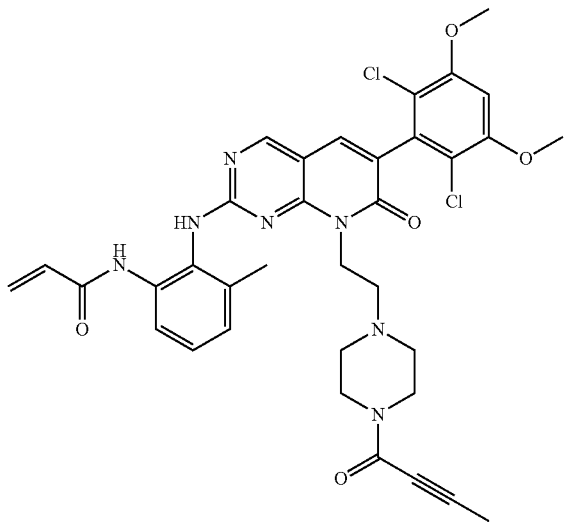 [SMILES: C=CC(=O)Nc1cccc(C)c1Nc1ncc2cc(-c3c(Cl)c(OC)cc(OC)c3Cl)c(=O)n(CCN3CCN(C(=O)C#CC)CC3)c2n1] | 704 |
| 12-2 | 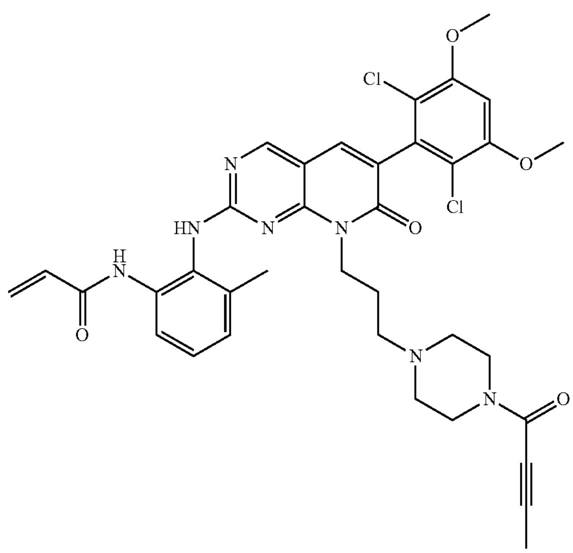 [SMILES: C=CC(=O)Nc1cccc(C)c1Nc1ncc2cc(-c3c(Cl)c(OC)cc(OC)c3Cl)c(=O)n(CCCN3CCN(C(=O)C#CC)CC3)c2n1] | 718 |
| 12-3 | 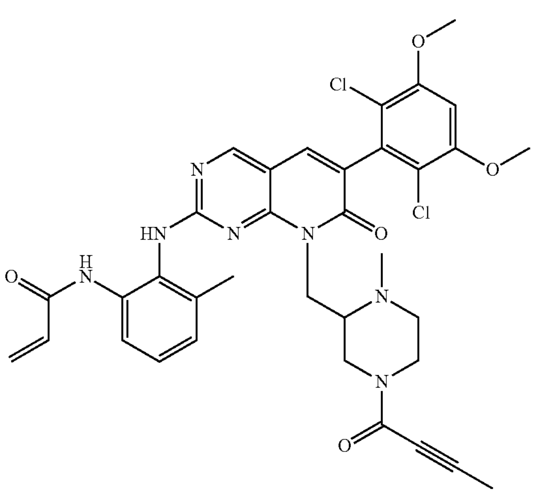 [SMILES: C=CC(=O)Nc1cccc(C)c1Nc1ncc2cc(-c3c(Cl)c(OC)cc(OC)c3Cl)c(=O)n(CC3CN(C(=O)C#CC)CCN3C)c2n1] | 704 |

The compounds below are prepared by methods substantially identical, similar, or analogous to those disclosed in examples 7-11.
| | | |
|---|---|---|
| 12-4 | 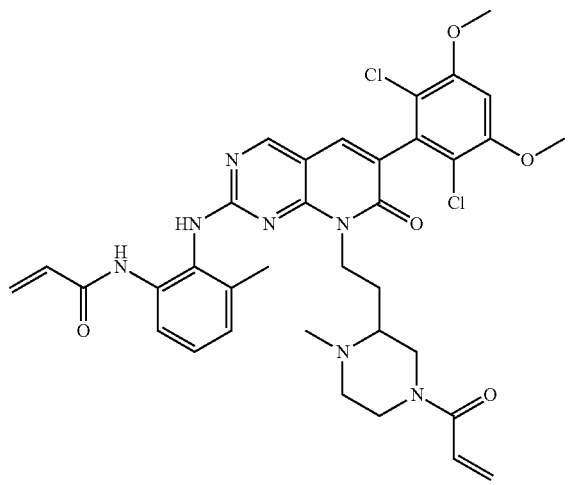 [SMILES: C=CC(=O)Nc1cccc(C)c1Nc1ncc2cc(-c3c(Cl)c(OC)cc(OC)c3Cl)c(=O)n(CCC3CN(C(=O)C=C)CCN3C)c2n1] | 706 |
| 12-5 | 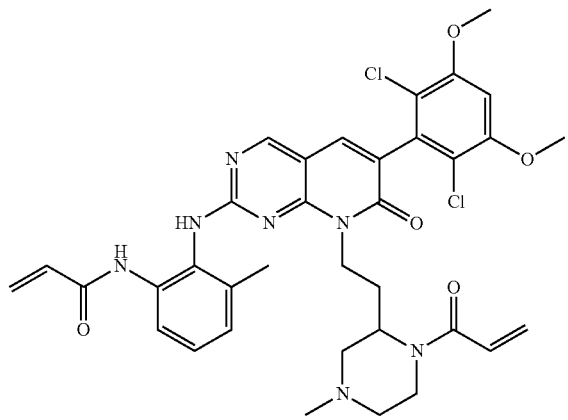 [SMILES: C=CC(=O)Nc1cccc(C)c1Nc1ncc2cc(-c3c(Cl)c(OC)cc(OC)c3Cl)c(=O)n(CCC3CN(C)CCN3C(=O)C=C)c2n1] | 706 |
| 12-6 | 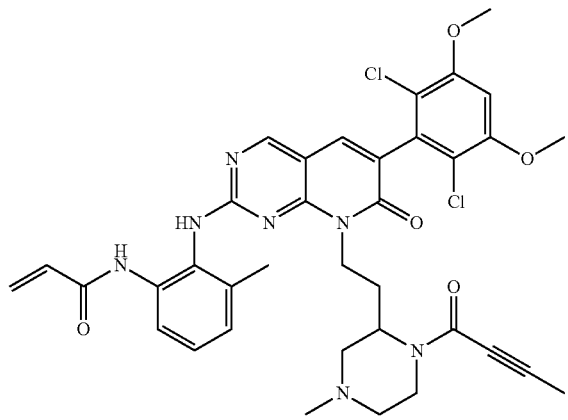 [SMILES: C=CC(=O)Nc1cccc(C)c1Nc1ncc2cc(-c3c(Cl)c(OC)cc(OC)c3Cl)c(=O)n(CCC3CN(C)CCN3C(=O)C#CC)c2n1] | 718 |

| | |
|---|---|
| 12-7 | 718 |
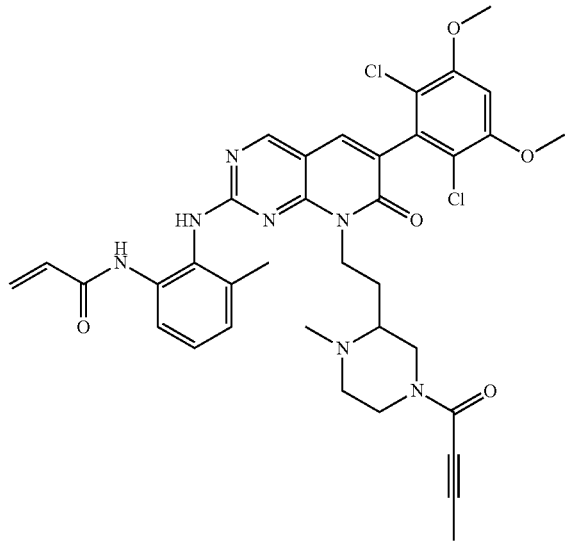 [SMILES: C=CC(=O)Nc1cccc(C)c1Nc1ncc2cc(-c3c(Cl)c(OC)cc(OC)c3Cl)c(=O)n(CCC3CN(C(=O)C#CC)CCN3C)c2n1]
| | |
|---|---|
| 12-8 | 685 |
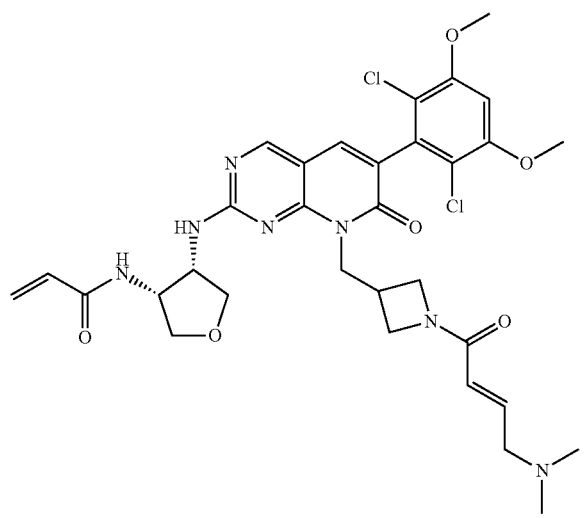 [SMILES: C=CC(=O)N[C@H]1COC[C@H]1Nc1ncc2cc(-c3c(Cl)c(OC)cc(OC)c3Cl)c(=O)n(CC3CN(C(=O)/C=C/CN(C)C)C3)c2n1]
| | |
|---|---|
| 12-9 | 700 |
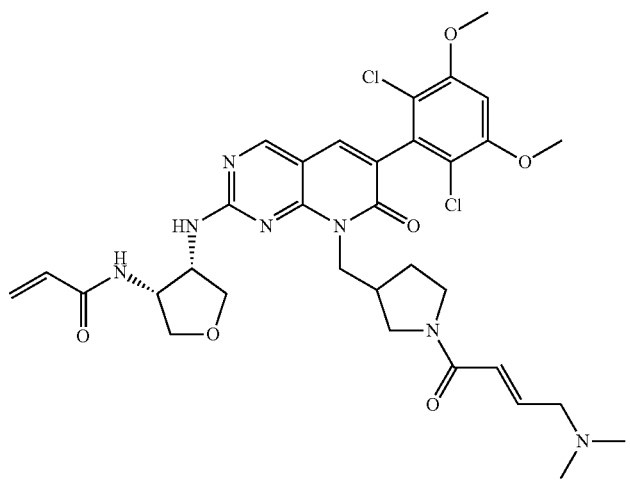 [SMILES: C=CC(=O)N[C@H]1COC[C@H]1Nc1ncc2cc(-c3c(Cl)c(OC)cc(OC)c3Cl)c(=O)n(CC3CCN(C(=O)/C=C/CN(C)C)C3)c2n1]

| | | |
|---|---|---|
| 12-10 | 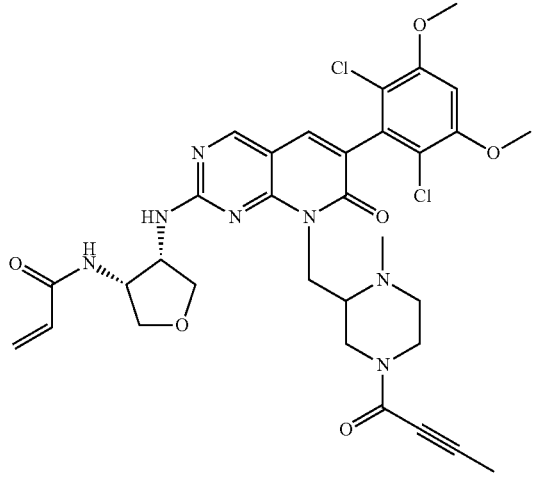 [SMILES: C=CC(=O)N[C@H]1COC[C@H]1Nc1ncc2cc(-c3c(Cl)c(OC)cc(OC)c3Cl)c(=O)n(CC3CN(C(=O)C#CC)CCN3C)c2n1] | 684 |
| 12-11 | 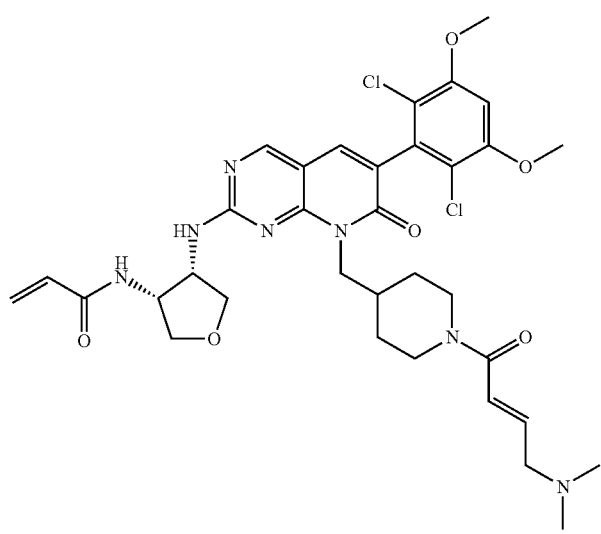 [SMILES: C=CC(=O)N[C@H]1COC[C@H]1Nc1ncc2cc(-c3c(Cl)c(OC)cc(OC)c3Cl)c(=O)n(CC3CCN(C(=O)/C=C/CN(C)C)CC3)c2n1] | 714 |
| 12-12 | 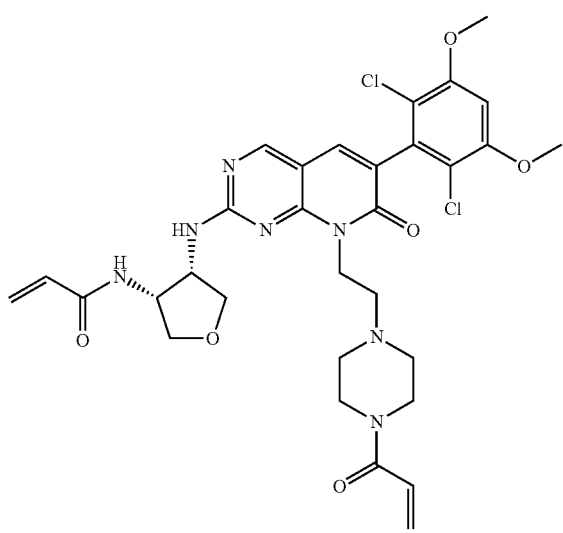 [SMILES: C=CC(=O)N[C@H]1COC[C@H]1Nc1ncc2cc(-c3c(Cl)c(OC)cc(OC)c3Cl)c(=O)n(CCN3CCN(C(=O)C=C)CC3)c2n1] | 672 |

12-13 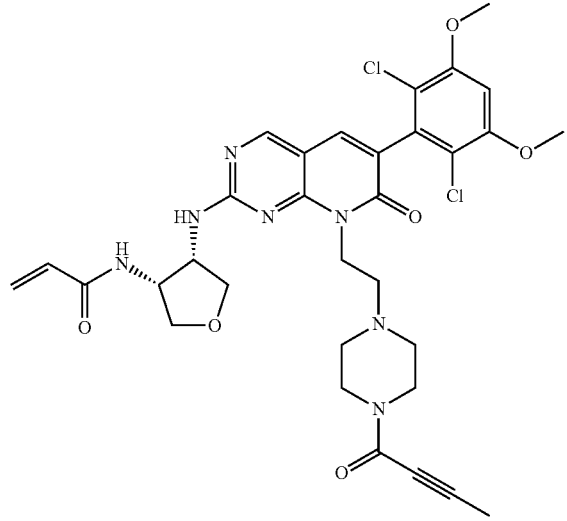 [SMILES: C=CC(=O)N[C@H]1COC[C@H]1Nc1ncc2cc(-c3c(Cl)c(OC)cc(OC)c3Cl)c(=O)n(CCN3CCN(C(=O)C#CC)CC3)c2n1] 684
12-14 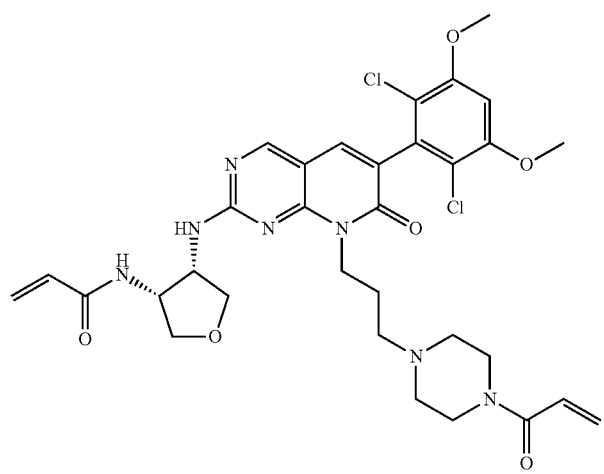 [SMILES: C=CC(=O)N[C@H]1COC[C@H]1Nc1ncc2cc(-c3c(Cl)c(OC)cc(OC)c3Cl)c(=O)n(CCCN3CCN(C(=O)C=C)CC3)c2n1] 686
12-15 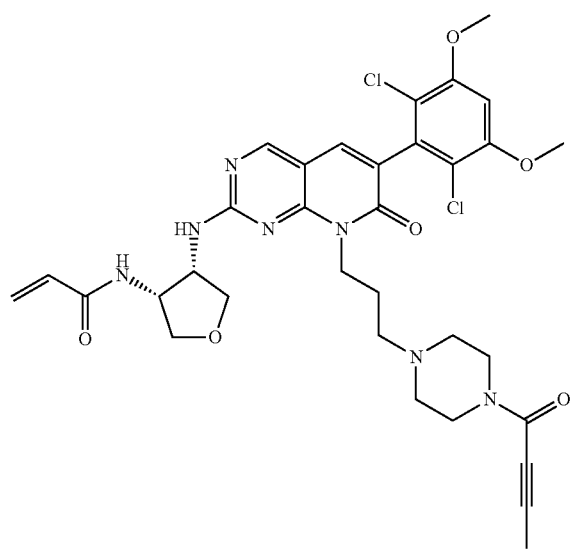 [SMILES: C=CC(=O)N[C@H]1COC[C@H]1Nc1ncc2cc(-c3c(Cl)c(OC)cc(OC)c3Cl)c(=O)n(CCCN3CCN(C(=O)C#CC)CC3)c2n1] 698

12-16 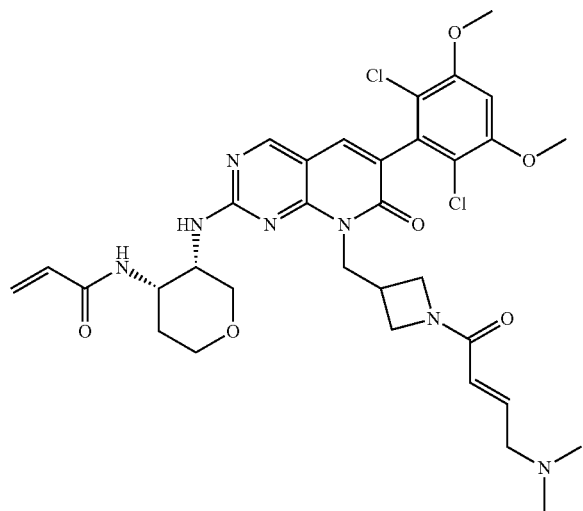 [SMILES: C=CC(=O)N[C@H]1CCOC[C@H]1Nc1ncc2cc(-c3c(Cl)c(OC)cc(OC)c3Cl)c(=O)n(CC3CN(C(=O)/C=C/CN(C)C)C3)c2n1] 700
12-17 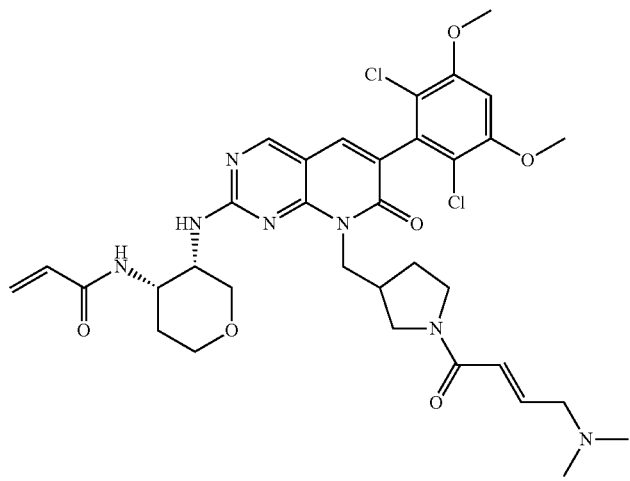 [SMILES: C=CC(=O)N[C@H]1CCOC[C@H]1Nc1ncc2cc(-c3c(Cl)c(OC)cc(OC)c3Cl)c(=O)n(CC3CCN(C(=O)/C=C/CN(C)C)C3)c2n1] 714
12-18 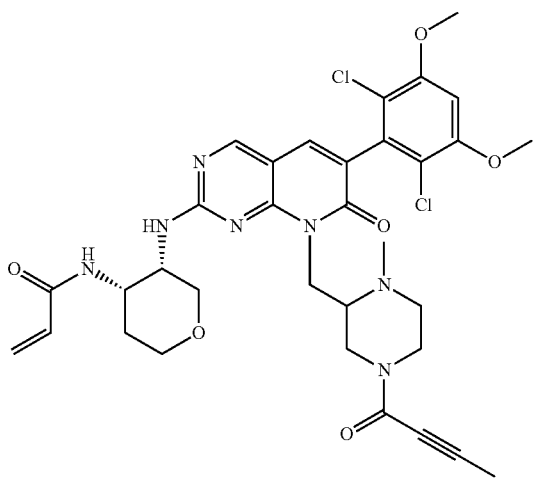 [SMILES: C=CC(=O)N[C@H]1CCOC[C@H]1Nc1ncc2cc(-c3c(Cl)c(OC)cc(OC)c3Cl)c(=O)n(CC3CN(C(=O)C#CC)CCN3C)c2n1] 698

12-19 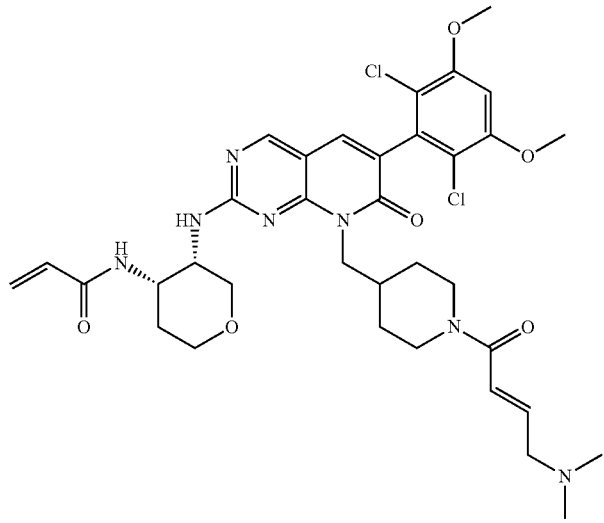 [SMILES: C=CC(=O)N[C@H]1CCOC[C@H]1Nc1ncc2cc(-c3c(Cl)c(OC)cc(OC)c3Cl)c(=O)n(CC3CCN(C(=O)/C=C/CN(C)C)CC3)c2n1] 728
12-20 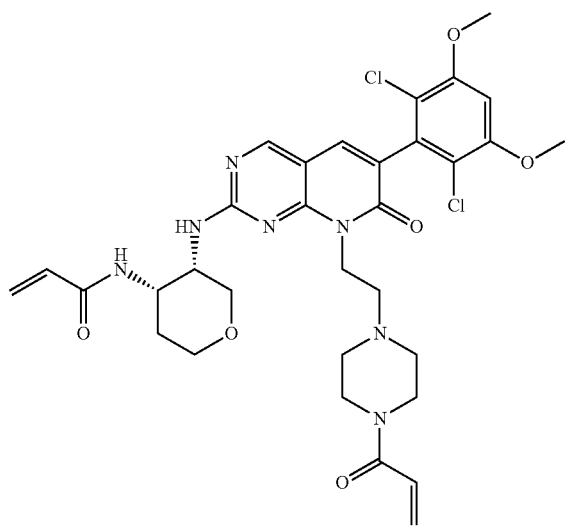 [SMILES: C=CC(=O)N[C@H]1CCOC[C@H]1Nc1ncc2cc(-c3c(Cl)c(OC)cc(OC)c3Cl)c(=O)n(CCN3CCN(C(=O)C=C)CC3)c2n1] 686
12-21 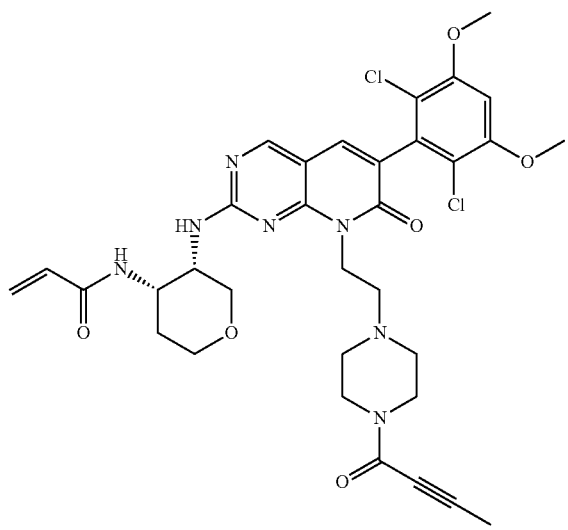 [SMILES: C=CC(=O)N[C@H]1CCOC[C@H]1Nc1ncc2cc(-c3c(Cl)c(OC)cc(OC)c3Cl)c(=O)n(CCN3CCN(C(=O)C#CC)CC3)c2n1] 698

12-22 700
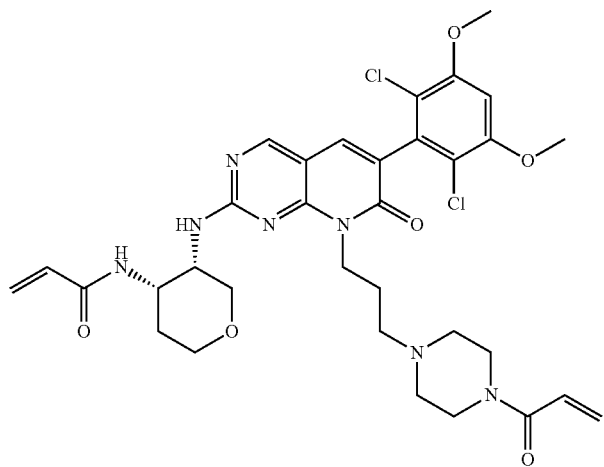 [SMILES: C=CC(=O)N[C@H]1CCOC[C@H]1Nc1ncc2cc(-c3c(Cl)c(OC)cc(OC)c3Cl)c(=O)n(CCCN3CCN(C(=O)C=C)CC3)c2n1]
12-23 712
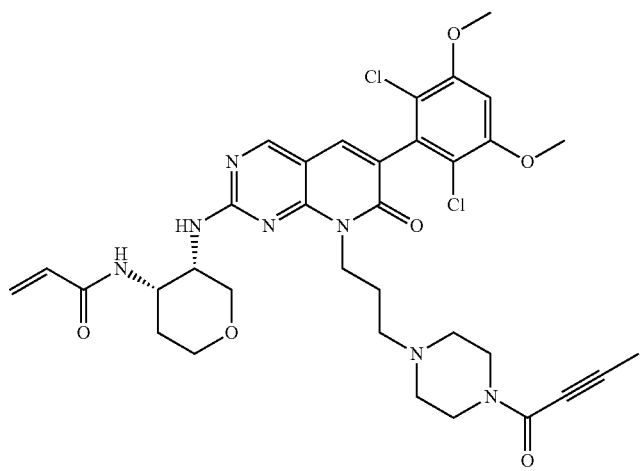 [SMILES: C=CC(=O)N[C@H]1CCOC[C@H]1Nc1ncc2cc(-c3c(Cl)c(OC)cc(OC)c3Cl)c(=O)n(CCCN3CCN(C(=O)C#CC)CC3)c2n1]
12-24 700
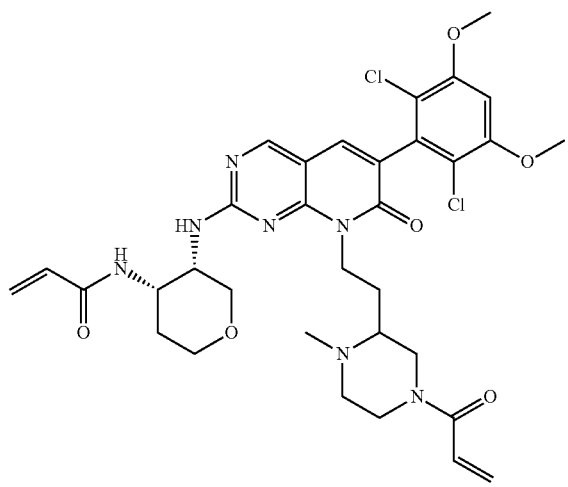 [SMILES: C=CC(=O)N[C@H]1CCOC[C@H]1Nc1ncc2cc(-c3c(Cl)c(OC)cc(OC)c3Cl)c(=O)n(CCC3CN(C(=O)C=C)CCN3C)c2n1]

12-25 712

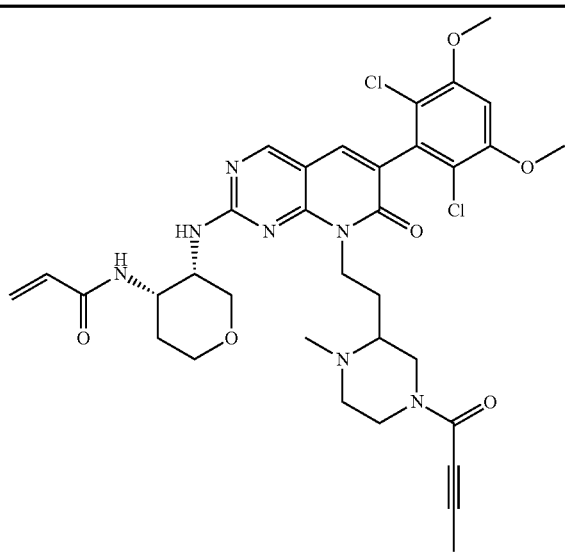

12-26 700

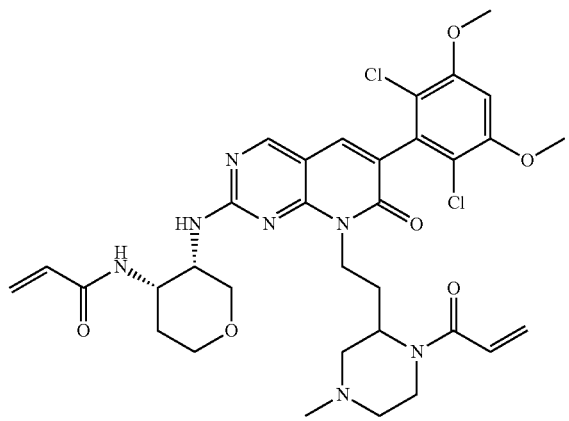 [SMILES: C=CC(=O)N[C@H]1CCOC[C@H]1Nc1ncc2cc(-c3c(Cl)c(OC)cc(OC)c3Cl)c(=O)n(CCC3CN(C)CCN3C(=O)C=C)c2n1]

12-27 712

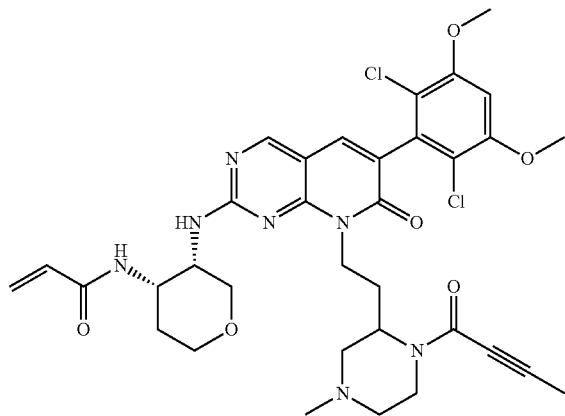 [SMILES: C=CC(=O)N[C@H]1CCOC[C@H]1Nc1ncc2cc(-c3c(Cl)c(OC)cc(OC)c3Cl)c(=O)n(CCC3CN(C)CCN3C(=O)C#CC)c2n1]

Biological Example 1: Inhibition of Enzymatic Activity

In order to assess the activity of chemical compounds against the relevant kinase of interest, the Caliper LifeSciences electrophoretic mobility shift technology platform is utilized. Fluorescently labeled substrate peptide is incubated in the presence dosed levels of compounds, a set concentration of kinase and of ATP, so that a reflective proportion of the peptide is phosphorylated. At the end of the reaction, the mix of phosphorylated (product) and non-phosphorylated (substrate) peptides are passed through the microfluidic system of the Caliper LabChip® EZ Reader II, under an applied potential difference. The presence of the phosphate group on the product peptide provides a difference in mass and charge between the product peptide and the substrate peptide, resulting in a separation of the substrate and product pools in the sample. As the pools pass the LEDS within the instrument, these pools are detected and resolved as separate peaks. The ratio between these peaks therefore reflects the activity of the chemical matter at that concentration in that well, under those conditions.

FGFR-1/2/3 wild type assay at Km: In each well of a 384-well plate, 0.1 ng/ul of wild type FGFR-1/2/3 (Carna Biosciences, Inc.) was incubated in a total of 12.5 ul of buffer (100 mM HEPES pH 7.5, 0.015% Brij 35, 10 mM $MgCl_2$, ImM DTT) with 1 uM CSKtide (5-FAMKKKKEEI-YFFFG-$NH_2$) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −700, downstream voltage −3000, post sample sip 35 s).

FGFR-4 wild type assay at Km: In each well of a 384-well plate, 0.5 ng/ul of wild type FGFR-4 (Carna Biosciences, Inc.) was incubated in a total of 12.5 ul of buffer (100 mM HEPES pH 7.5, 0.015% Brij 35, 10 mM $MgCl_2$, ImM DTT) with 1 uM CSKtide (5-FAM-KKKKEEIYFFFG-$NH_2$) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper LabChip® EZ Reader II (protocol settings: −1.9 psi, upstream voltage −700, downstream voltage −3000, post sample sip 35 s).

Such assays, carried out with a range of doses of test compounds, allow the determination of an approximate IC50 value. Although the inhibitory properties of the compounds of the present invention vary with structural change as expected, the activity generally exhibited by these agents is in the range of IC50=0.1-1000 nM. The following table lists the IC50 values of certain compounds of the invention.

| Compound | FGFR-1 | FGFR-2 | FGFR-3 | FGFR-4 |
|---|---|---|---|---|
| CY-15-2 | >1000 nM | >1000 nM | >1000 nM | <50 nM |
| CY-15-3 | >1000 nM | >1000 nM | >1000 nM | <50 nM |
| CY-15-4 | | | | <50 nM |
| CY-15-5 | | | | <50 nM |
| CY-15-6 | | | | <50 nM |
| CY-15-7 | | | | <50 nM |
| CY-15-8 | | | | <50 nM |

Biological Example 2: In Vitro Irreversible Kinetics Study

Covalent kinase inhibitors have several characteristics that functionally differentiate themselves from their reversible counterparts. Generally, (1) covalent kinase inhibitors have electrophilic substituents that react covalently with nucleophilic centers on their target kinase; (2) covalent kinase inhibitors exhibit two-step inhibitory kinetics marked by a fast reversible binding event, followed by a slow covalent (irreversible) binding event, which causes the overall kinetics of target inactivation to be slow relative to noncovalent inhibitors; and (3) once covalently bound, covalent kinase inhibitors are impervious to washout of the inhibitors and are no longer ATP-competitive. The scanKINETIC™ assay is used to determine whether the compound is an irreversible inhibitor or reversible inhibitor. Four sets of dose-response curve study Arms (A, B, C, D) comprise a scanKINETIC experiment. Arm A addresses association and dissociation kinetics; Arm B addresses dissociation kinetics; Arm C (in concert with Arm A) addresses association kinetics; and Arm D addresses dissociation kinetics & serves as a control for reagent dilution.

In Arm A, compound and kinase are combined and equilibrated for six hours ($t_1+t_2$). In Arm B, compound and kinase are combined and equilibrated for 1 hour ($t_1$), and the samples are then diluted (30-fold) in reaction buffer (described above) and equilibrated for 5 hours ($t_2$). In Arm C, compound and kinase are combined and equilibrated for 1 hour ($t_1$). In Arm D, compound and kinase are combined and immediately diluted 30-fold in reaction buffer. The reaction is then allowed to equilibrate for 6 hours ($t_1+t_2$). Post-equilibration, each study arm sample is combined briefly with liganded affinity beads. All reactions are subsequently washed, eluted, read-out by qPCR, and the data are fit to the Hill equation to calculate apparent $K_d$ values, as described above. Curve fitting intentionally ignores test compound dilution in Arms B&D. For irreversible inhibitors, the Kd values for Arm A&B are equivalent, since for Arm B, the inhibitor fails to dissociate after the reaction dilution step.

Biological Example 3: In Vitro Cellular Assay

Induction of apoptosis with an inhibitor of FGFR4 is assessed in Hep3B cell. Hep3B is a liver cell line that has a FGFR-4 aberrant signaling pathway (FGF19 amplification). First Hep3B cells were seeded at 20 k/well in 96-well white plates in 200 ul of DMEM/5% FBS overnight. The next day compound was added at a final DMSO concentration of 0.1% and incubated for 6 hours. Caspase activity was measured according to manufacture instruction (Caspase-Glo3/7 Assay (Promega)). Briefly, 100 ul of Caspase-Glo3/7 reagent was added to each well and incubated for 1 hour in the dark. Luminescence was measured using En Vision. The average Caspase activity of 2 replicates was plotted with three parameter dose-response (inhibition) curve fit using Prism GraphPad software, which was used to determine the IC50 values.

The antiproliferative activity of compounds are assessed in the patient-derived liver cancer cell line LIXC012 (Shanghai ChemPartner Co., LTD) by PerkinElmer ATPlite™ Luminescence Assay System. LIXC012 cell line has a FGFR-4 aberrant signaling pathway (FGF19-overexpressing). Briefly, the various test cancer cell lines are plated at a density of about $1\times10^4$ cells per well in Costar 96-well plates, and are incubated with different concentrations of compounds for about 72 hours in medium supplemented with 5% FBS. One lyophilized substrate solution vial is then reconstituted by adding 5 mL of substrate buffer solution, and is agitated gently until the solution is homogeneous. About 50 μL of mammalian cell lysis solution is added to 100 μL of cell suspension per well of a microplate, and the plate is shaken for about five minutes in an orbital shaker at ~700 rpm. This procedure is used to lyse the cells and to stabilize the ATP. Next, 50 μL substrate solution is added to the wells and microplate is shaken for five minutes in an orbital shaker at ~700 rpm. Finally, the luminescence is measured by a PerkinElmer TopCount® Microplate Scintillation Counter. Such assays, carried out with a range of doses of test compounds, allow the determination of the cellular anti-antiproliferative $IC_{50}$ of the compounds of the present invention. The following table lists the IC50 values of certain compounds of the invention in the FGF19-overexpressing Patient-Derived liver cancer cell line LIXC012.

These findings are the demonstration of a therapeutic strategy that targets a subset of patients with HCC with FGFR-4 aberrant signaling pathway.

|  | LIXC012 (uM) |
| --- | --- |
| CY-15-2 | 0.49 |
| CY-15-3 | 0.66 |
| BLU9931 (reference drug) | 0.28 |

Biological Example 4: In Vivo Xenograft Studies

Aberrant signaling through the fibroblast growth factor 19 (FGF19)/fibroblast growth factor receptor 4 (FGFR 4) signaling complex has been shown to cause hepatocellular carcinoma (HCC) in mice and has been implicated to play a similar role in humans. Approximately one third of patients with HCC whose tumors express FGF19 together with FGFR4 and its coreceptor klotho (KLB) could potentially respond to treatment with an FGFR4 inhibitor.

The compounds with potent inhibition of proliferation in LIXC012 cells in vitro are further evaluated in the Hep3B xenograft model and LIXC012 PDX xenograft model. Briefly, athymic nude mice (CD-1 nu/nu) or SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 mm$^3$, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant.

What is claimed is:

1. A compound of Formula (II), or a pharmaceutically acceptable salt, solvate, stereoisomer, tautomer, or an isotopic form thereof:

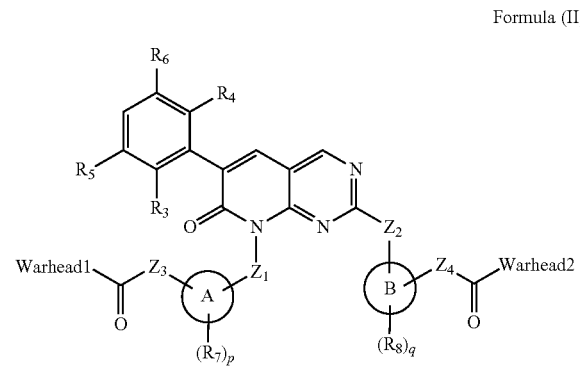

Formula (II)

wherein:
each of A, and B is heterocycloalkyl or aryl;
$Z_1$ is alkyl, alkenyl, or alkynyl;
$Z_2$ is N(H), O, S, S(O$_2$);
$Z_3$ is N(R$_a$) if the atom which $Z_3$ connects to ring A is a carbon atom; or $Z_3$ is a direct bond if ring A is a heterocycloalkyl and the atom which $Z_3$ connects to ring A is a nitrogen atom;
$Z_4$ is N(R$_a$) if the atom which $Z_4$ connects to ring B is a carbon atom; or $Z_4$ is direct bond if ring B is a heterocycloalkyl and the atom which $Z_4$ connects to ring B is a nitrogen atom;
Warhead1 is

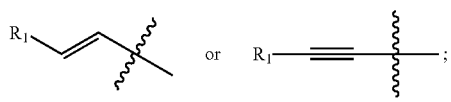

Warhead2 is

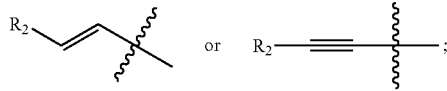

each of p, q, independently, is 0, 1, 2, 3, or 4;
each of $R_1$, $R_2$, $R_7$, and $R_8$, independently, is H, alkyl, alkenyl, alkynyl, cycloalkyl, cycloalkenyl, heterocycloalkyl, heterocycloalkenyl, aryl, heteroaryl, halo, nitro, oxo, cyano, OR$_a$, SR$_a$, alkyl-R$_a$, alkyl-NR$_b$R$_c$, NR$_b$R$_c$, C(O)R$_a$, S(O)R$_a$, SO$_2$R$_a$, P(O)R$_b$R$_c$, C(O)N(R$_b$)R$_c$, N(R$_b$)C(O)R$_c$, C(O)OR$_a$, OC(O)R$_a$, SO$_2$N(R$_b$)R$_c$, or N(R$_b$)SO$_2$R$_c$, in which each R$_a$, independently, is alkyl; each of R$_b$ and R$_c$, independently, is H, alkyl, alkenyl, alkynyl, cycloalkyl, cycloalkenyl, heterocycloalkyl, heterocycloalkenyl, aryl, heteroaryl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, dialkylamino, or alkylamino;
each of $R_3$ and $R_4$, independently, is H or halo;
each of $R_5$ and $R_6$, independently, is H or OR$_a$.

2. The compound according to claim 1, or a pharmaceutically acceptable salt, solvate, tautomer, stereoisomer, or an isotopic form thereof, wherein $Z_1$ is alkyl.

3. The compound according to claim 2, or a pharmaceutically acceptable salt, solvate, tautomer, stereoisomer, or an isotopic form thereof, wherein the compound is represented by Formula (III)

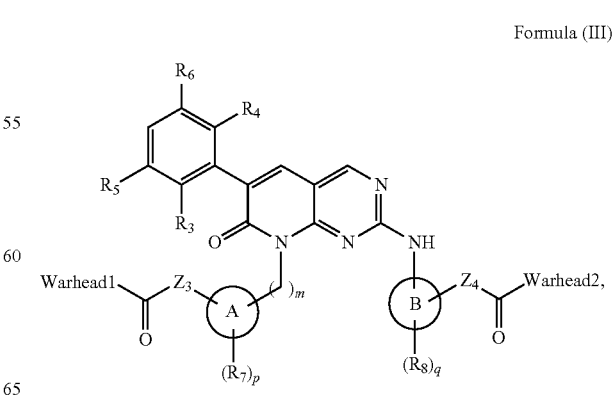

Formula (III)

wherein m is 1, 2, 3, or 4.

4. The compound according to claim 1, or a pharmaceutically acceptable salt, solvate, tautomer, stereoisomer, or an isotopic form thereof; wherein each of $R_3$ and $R_4$ is independently halo; each of $R_5$ and $R_6$ is independently alkoxy; and each of Warhead1 and Warhead2 is independently

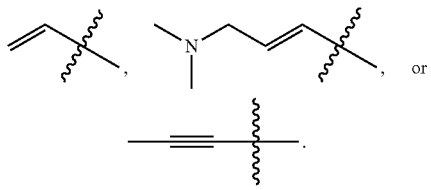

5. The compound according to claim 2, or a pharmaceutically acceptable salt, solvate, tautomer, stereoisomer, or an isotopic form thereof; wherein each of $R_3$ and $R_4$ is independently halo; each of $R_5$ and $R_6$ is independently alkoxy; and each of Warhead1 and Warhead2 is independently

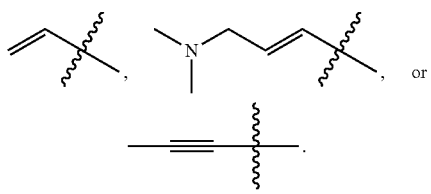

6. The compound according to claim 3, or a pharmaceutically acceptable salt, solvate, tautomer, stereoisomer, or an isotopic form thereof; wherein each of $R_3$ and $R_4$ is independently halo; each of $R_5$ and $R_6$ is independently alkoxy; and each of Warhead1 and Warhead2 is independently

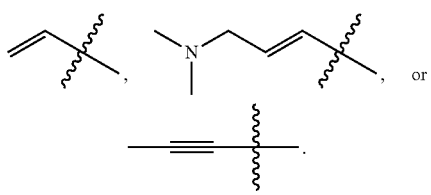

7. The compound according to claim 1, or a pharmaceutically acceptable salt, solvate, tautomer, stereoisomer, or an isotopic form thereof, wherein the compound is

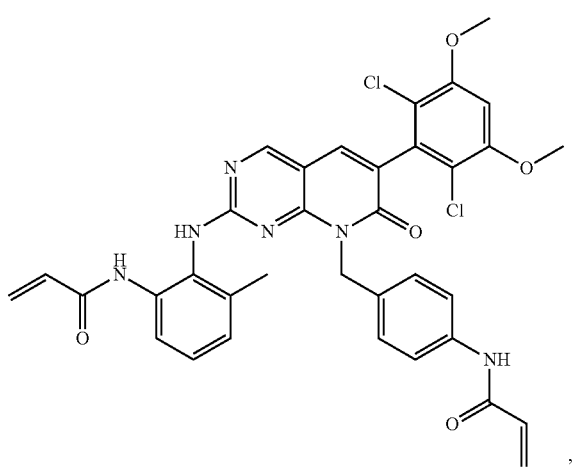

-continued

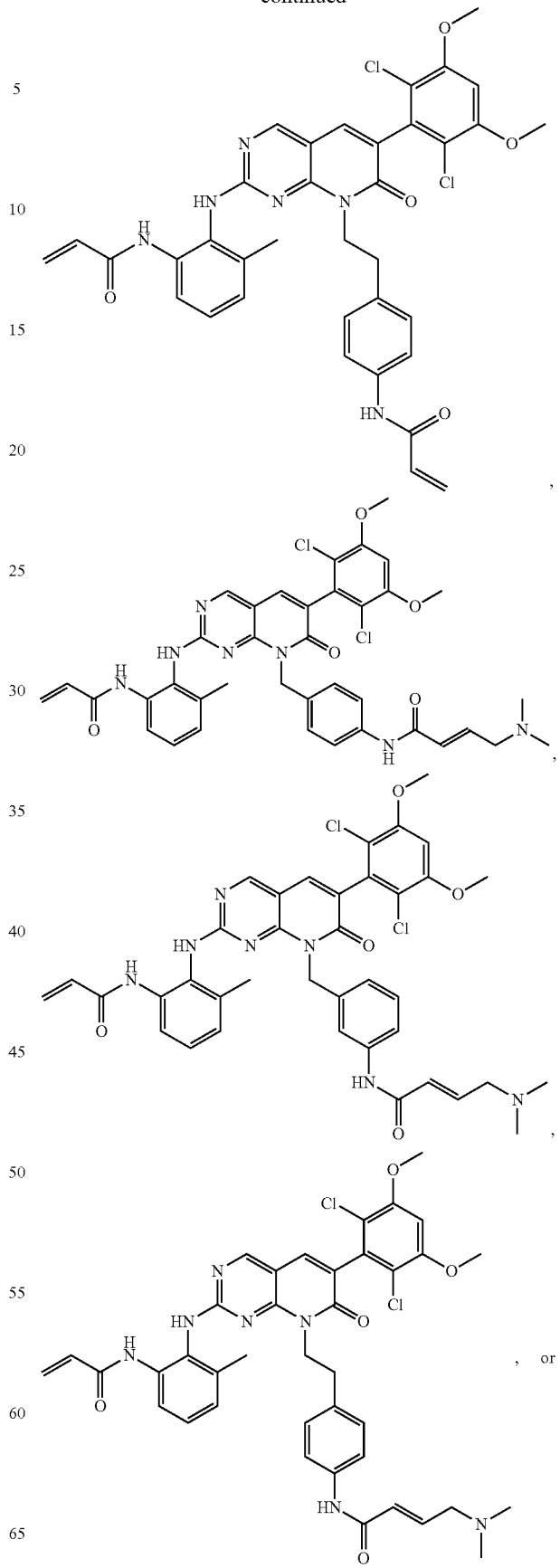

147
-continued
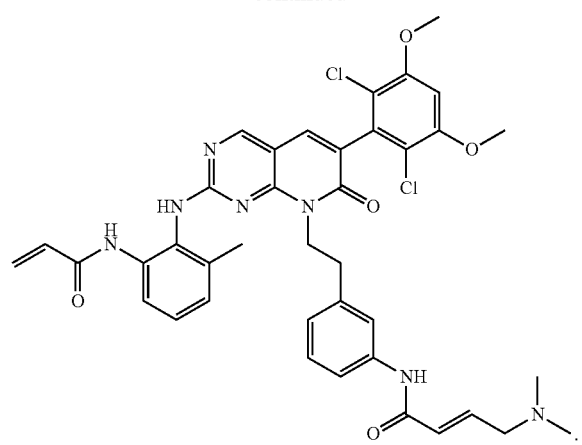
8. The compound according to claim 1, or a pharmaceutically acceptable salt, solvate, tautomer, stereoisomer, or an isotopic form thereof, wherein the compound is
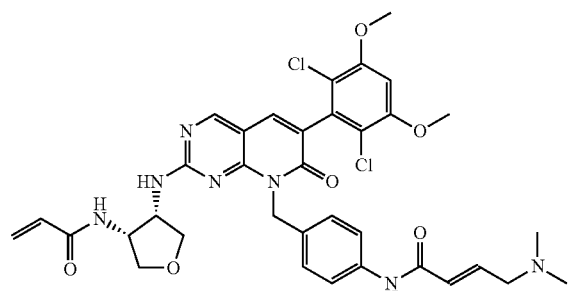
,
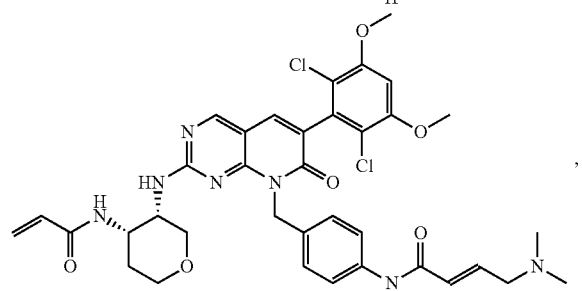
,
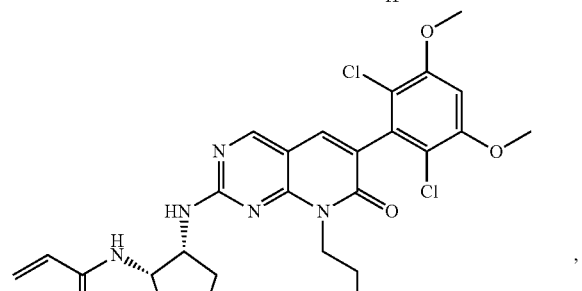
,
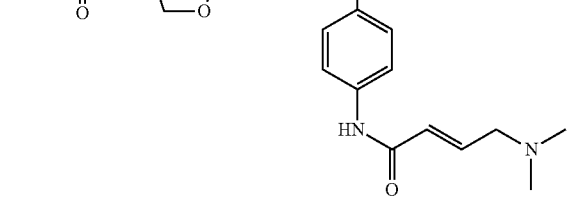
,
148
-continued
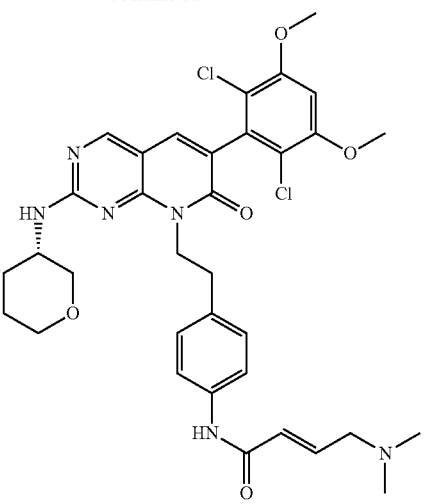
,
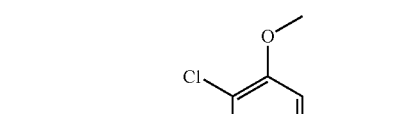
,
, or 149
-continued
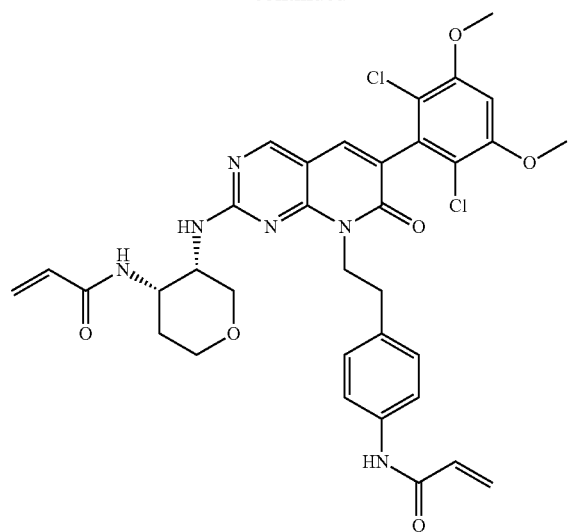
9. The compound according to claim 1, or a pharmaceutically acceptable salt, solvate, tautomer, stereoisomer, or an isotopic form thereof, wherein the compound is
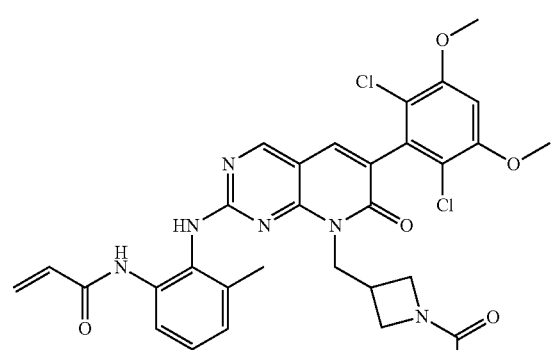
,
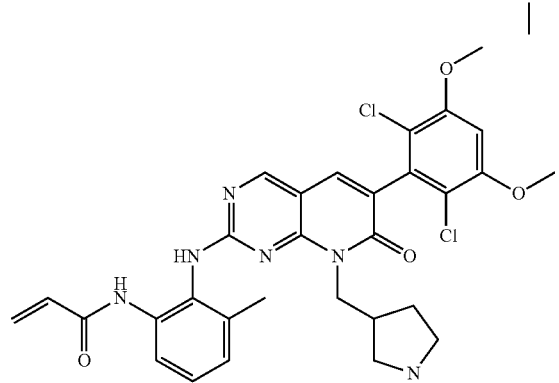
,
150
-continued
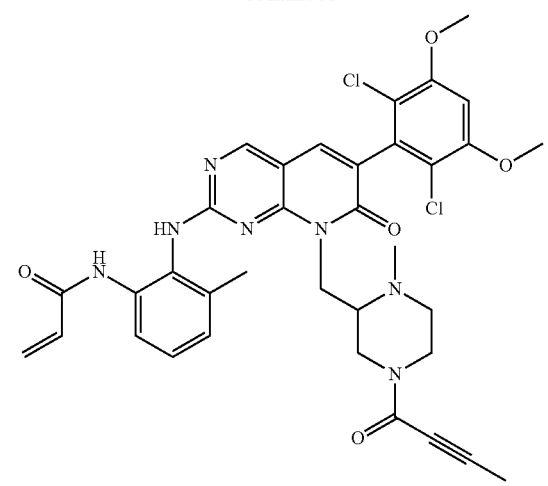
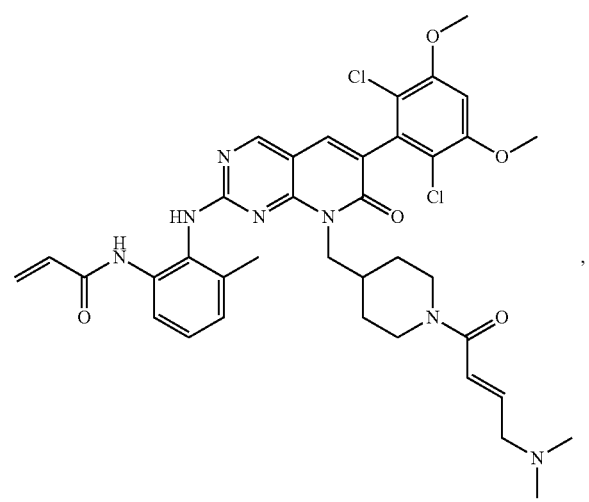
,
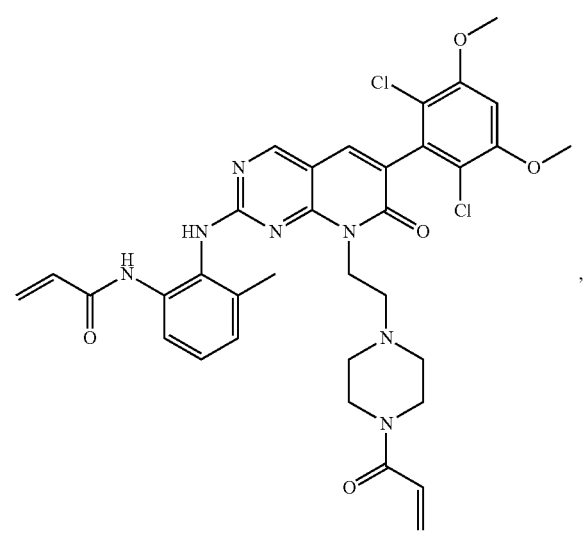
, 151
-continued
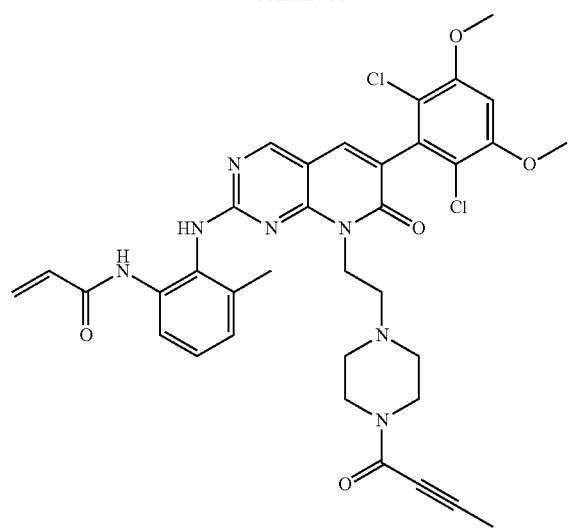
,
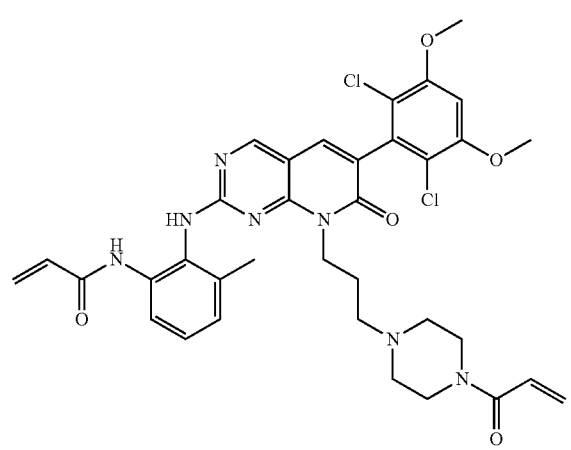
,
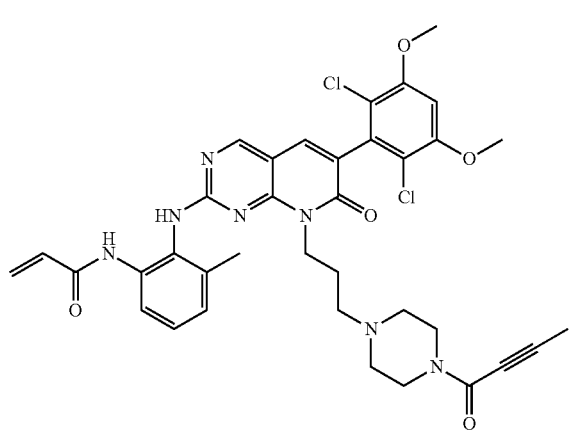
,
152
-continued
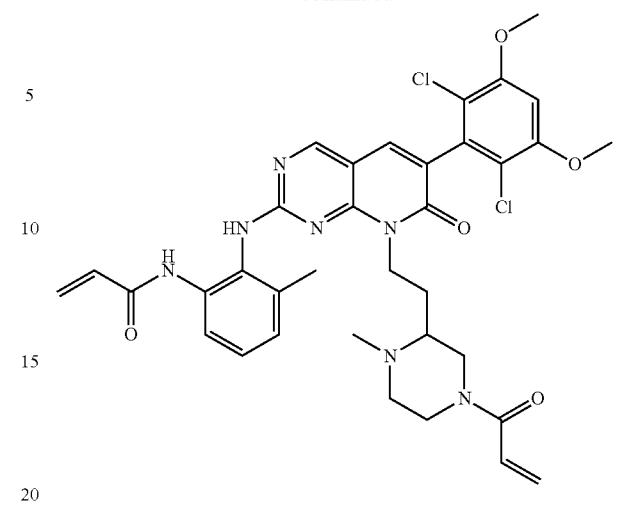
,
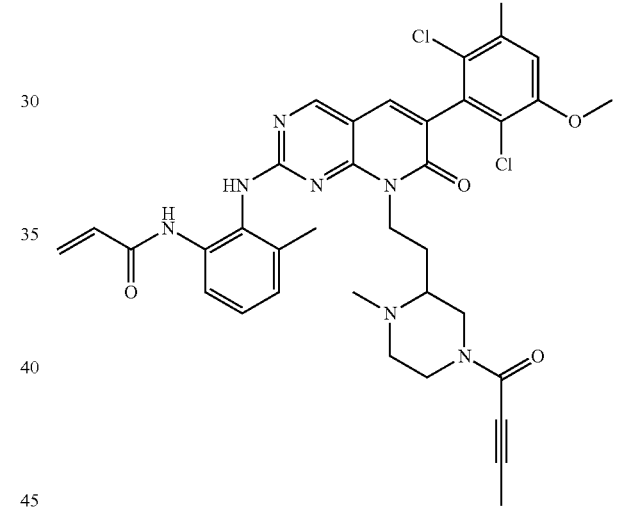
,
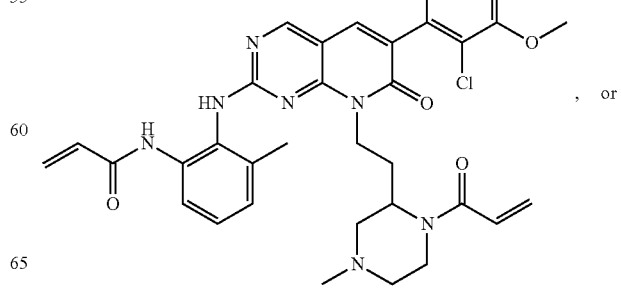
, or

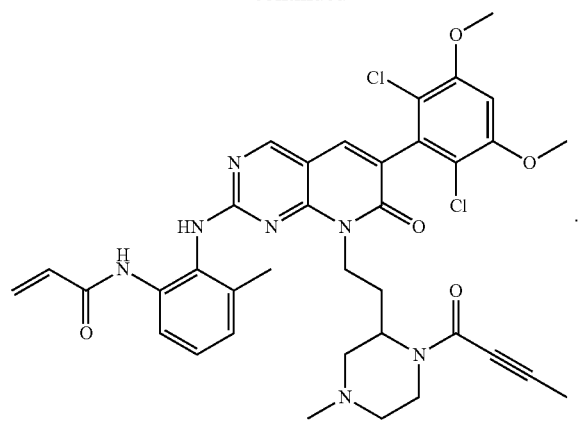
10. The compound according to claim 1, or a pharmaceutically acceptable salt, solvate, tautomer, stereoisomer, or an isotopic form thereof, wherein the compound is
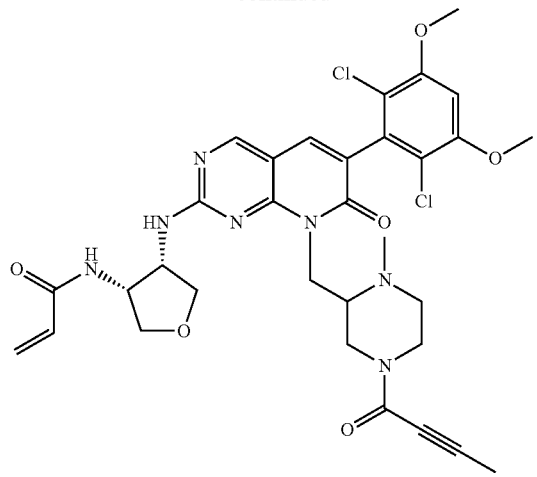
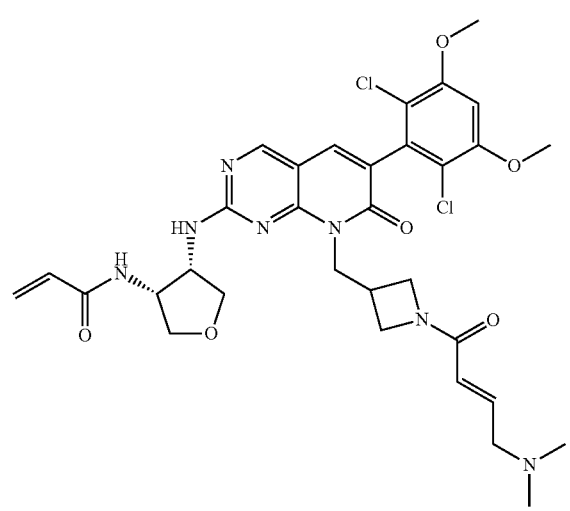
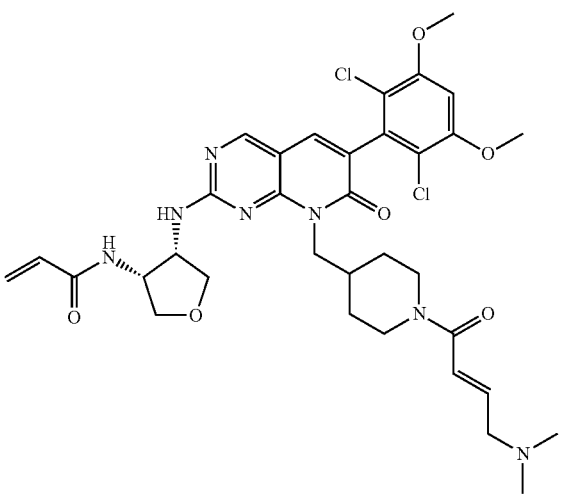
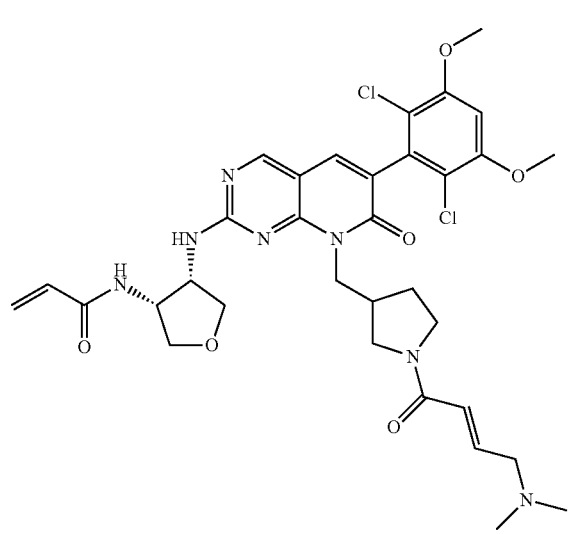
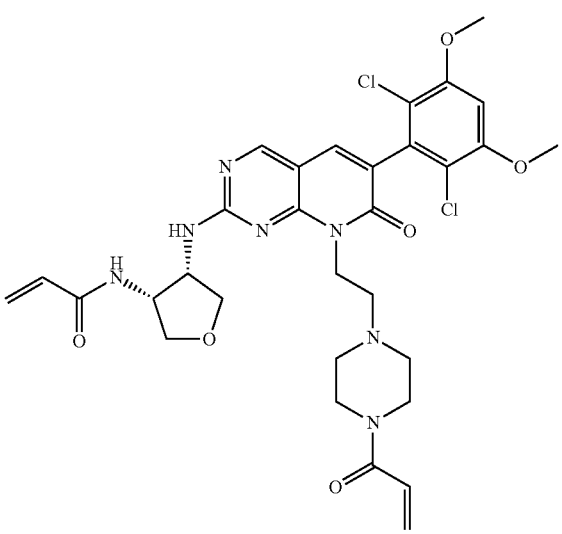

155
-continued
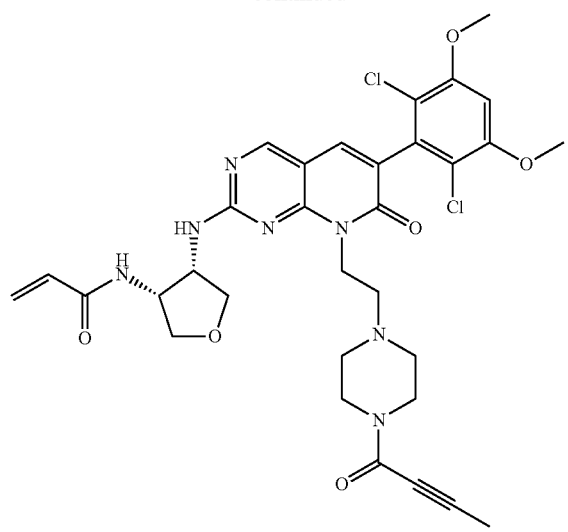
,
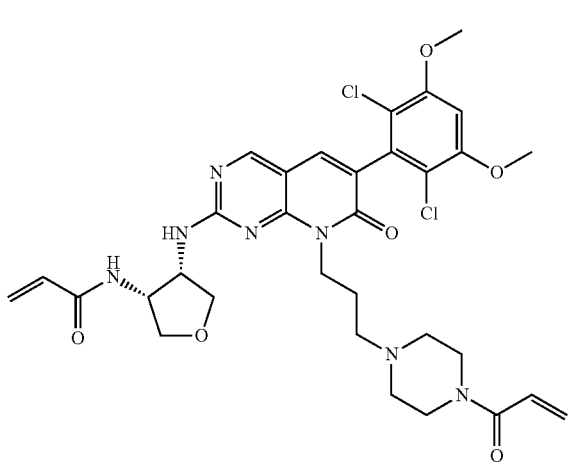
,
156
-continued
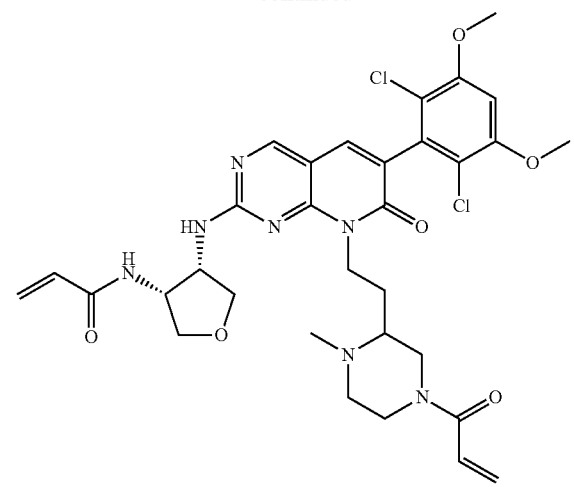
,
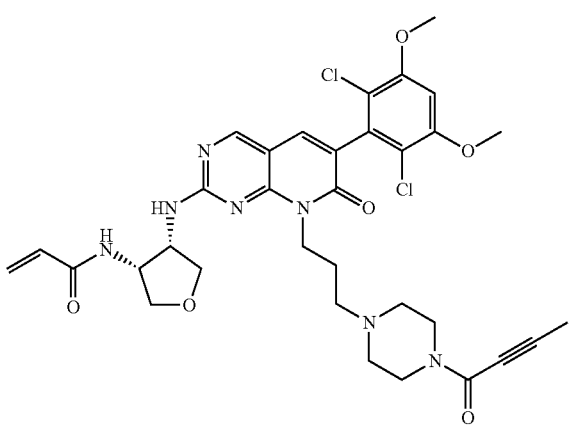
, or 157
-continued
158
-continued
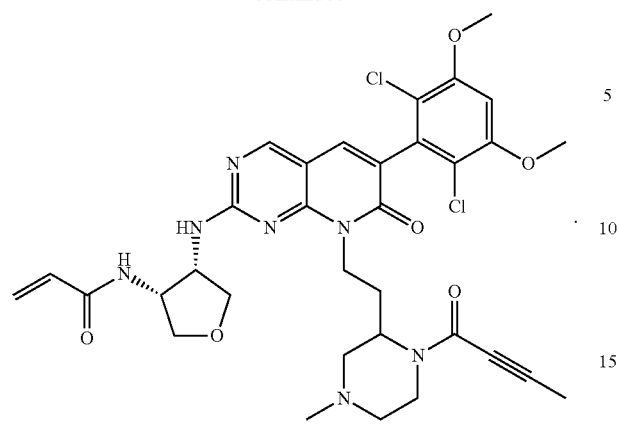
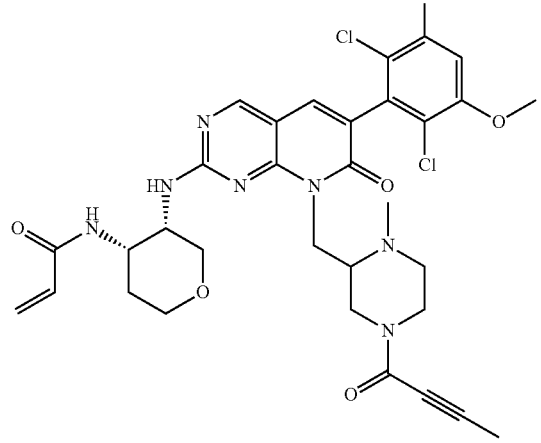
11. The compound according to claim 1, or a pharmaceutically acceptable salt, solvate, tautomer, stereoisomer, or an isotopic form thereof, wherein the compound is
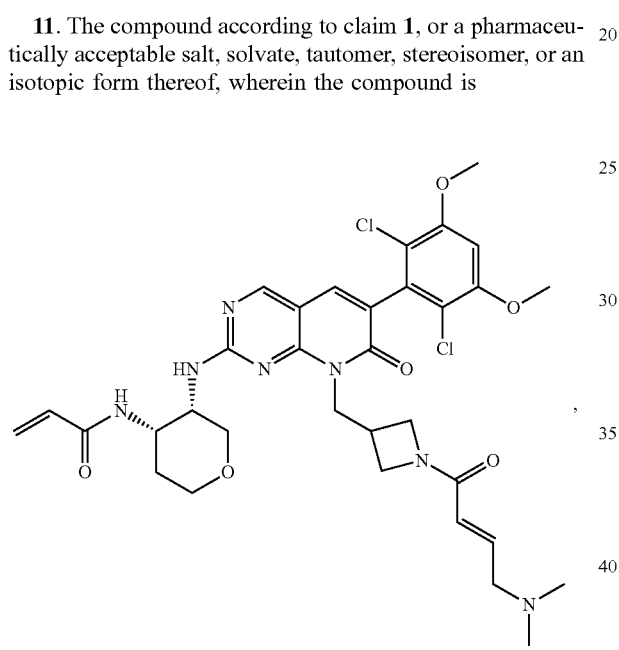
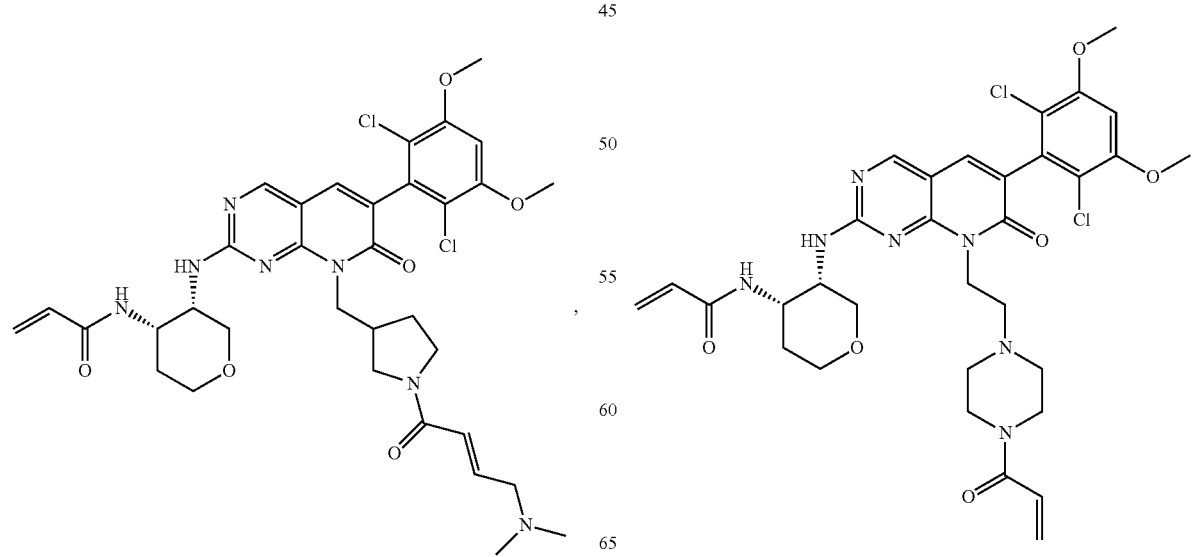

159
-continued
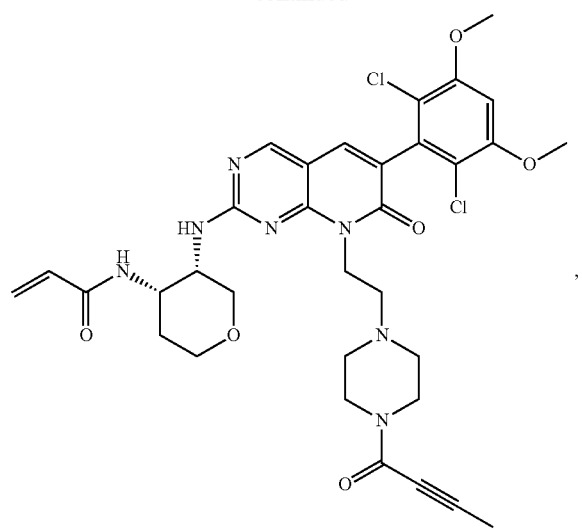
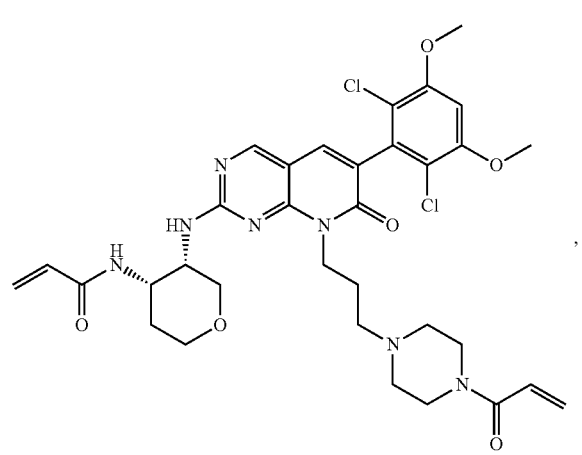
160
-continued
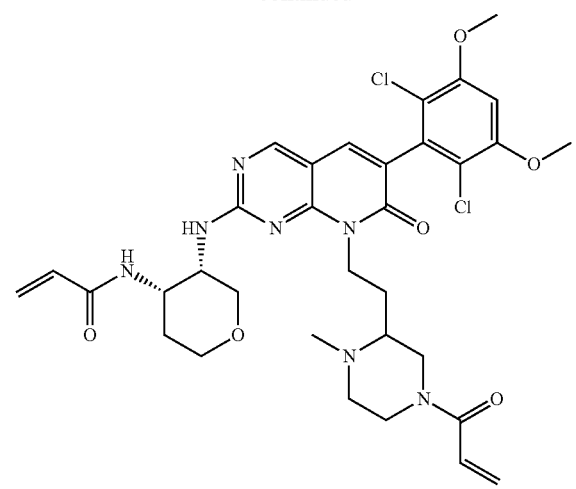
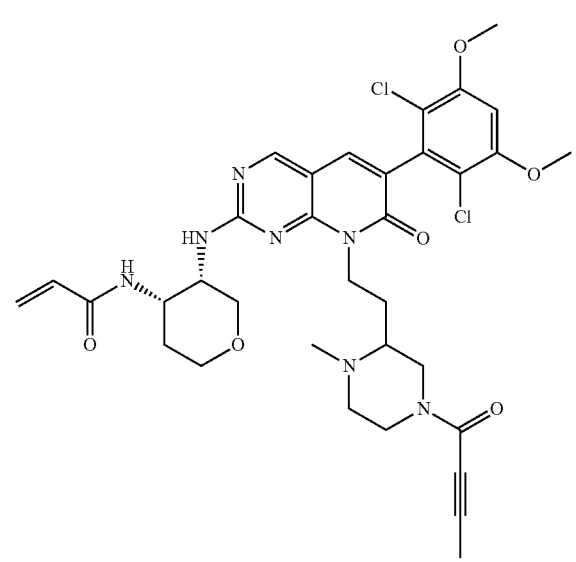
, or
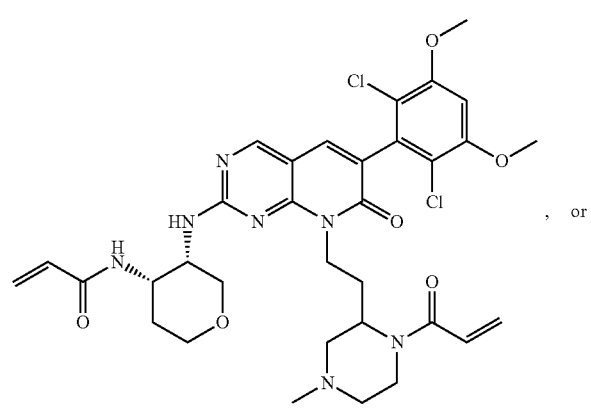

-continued

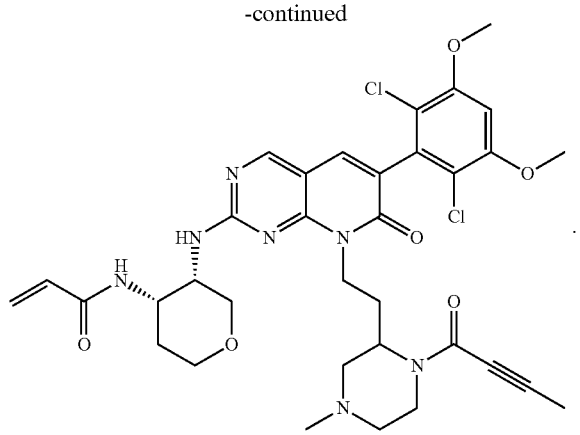

12. A pharmaceutical composition comprising a compound of Formula (I) as defined in claim 1, or a pharmaceutically acceptable salt, solvate, tautomer, stereoisomer, or an isotopic form thereof, and a pharmaceutically acceptable diluent or carrier.

13. A pharmaceutical composition comprising a compound of Formula (I) as defined in claim 7, or a pharmaceutically acceptable salt, solvate, tautomer, stereoisomer, or an isotopic form thereof, and a pharmaceutically acceptable diluent or carrier.

14. A pharmaceutical composition comprising a compound of Formula (I) as defined in claim 8, or a pharmaceutically acceptable salt, solvate, tautomer, stereoisomer, or an isotopic form thereof, and a pharmaceutically acceptable diluent or carrier.

15. A pharmaceutical composition comprising a compound of Formula (I) as defined in claim 9, or a pharmaceutically acceptable salt, solvate, tautomer, stereoisomer, or an isotopic form thereof, and a pharmaceutically acceptable diluent or carrier.

16. A pharmaceutical composition comprising a compound of Formula (I) as defined in claim 10, or a pharmaceutically acceptable salt, solvate, tautomer, stereoisomer, or an isotopic form thereof, and a pharmaceutically acceptable diluent or carrier.

17. A pharmaceutical composition comprising a compound of Formula (I) as defined in claim 11, or a pharmaceutically acceptable salt, solvate, tautomer, stereoisomer, or an isotopic form thereof, and a pharmaceutically acceptable diluent or carrier.

18. A method of treating a neoplastic disease, comprising administering to a subject in need thereof an effective amount of a compound of Formula (I) as defined in claim 1, or a pharmaceutically acceptable salt, solvate, tautomer, stereoisomer, or an isotopic form thereof, wherein said neoplastic disease is liver cancer, breast cancer, lung cancer, ovarian cancer, or a sarcoma.

19. A method of treating a neoplastic disease, comprising administering to a subject in need thereof an effective amount of a compound of Formula (I) as defined in claim 1, or a pharmaceutically acceptable salt, solvate, tautomer, stereoisomer, or an isotopic form thereof, wherein said neoplastic disease is hepatocellular carcinoma.

* * * * *